United States Patent
Jensen et al.

(10) Patent No.: US 9,884,058 B2
(45) Date of Patent: Feb. 6, 2018

(54) USE OF HSP70 AS A REGULATOR OF ENZYMATIC ACTIVITY

(71) Applicant: Orphazyme ApS, København N (DK)

(72) Inventors: Thomas Kirkegaard Jensen, Frederiksberg C (DK); Marja H. Jaattela, København Ø (DK)

(73) Assignee: Orphazyme ApS, København N (DK)

( * ) Notice: Subject to any disclaimer, the term of this patent is extended or adjusted under 35 U.S.C. 154(b) by 0 days.

(21) Appl. No.: 15/048,483

(22) Filed: Feb. 19, 2016

(65) Prior Publication Data

US 2016/0263096 A1    Sep. 15, 2016

Related U.S. Application Data

(60) Division of application No. 13/969,944, filed on Aug. 19, 2013, now Pat. No. 9,289,472, which is a continuation of application No. 13/001,316, filed as application No. PCT/DK2009/050151 on Jun. 26, 2009, now Pat. No. 8,540,985.

(30) Foreign Application Priority Data

Jun. 26, 2008 (DK) ................................ 2008 00885

(51) Int. Cl.
| | |
|---|---|
| A61K 45/06 | (2006.01) |
| A61K 31/445 | (2006.01) |
| A61K 31/4545 | (2006.01) |
| A61K 38/16 | (2006.01) |
| A61K 38/17 | (2006.01) |
| A61K 38/43 | (2006.01) |
| A61K 38/46 | (2006.01) |
| A61K 38/47 | (2006.01) |
| A61K 31/56 | (2006.01) |

(52) U.S. Cl.
CPC ........ *A61K 31/4545* (2013.01); *A61K 31/445* (2013.01); *A61K 31/56* (2013.01); *A61K 38/16* (2013.01); *A61K 38/17* (2013.01); *A61K 38/1709* (2013.01); *A61K 38/43* (2013.01); *A61K 38/46* (2013.01); *A61K 38/47* (2013.01); *A61K 45/06* (2013.01); *C12Y 306/01003* (2013.01)

(58) Field of Classification Search
None
See application file for complete search history.

(56) References Cited

U.S. PATENT DOCUMENTS

| | | |
|---|---|---|
| 5,348,945 A | 9/1994 | Berberian et al. |
| 5,830,464 A | 11/1998 | Srivastava |
| 5,948,646 A | 9/1999 | Srivastava |
| 5,985,270 A | 11/1999 | Srivastava |
| 6,007,821 A | 12/1999 | Srivastava et al. |
| 6,139,841 A | 10/2000 | Srivastava |
| 6,187,312 B1 | 2/2001 | Srivastava |
| 6,375,953 B1 | 4/2002 | Srivastava et al. |
| 6,384,029 B1 | 5/2002 | Jednakovits et al. |
| 6,403,095 B1 | 6/2002 | Srivastava et al. |
| 6,475,490 B1 | 11/2002 | Srivastava et al. |
| 6,649,628 B1 | 11/2003 | Kurthy et al. |
| 6,653,326 B1 | 11/2003 | Vigh et al. |
| 6,855,802 B1 | 2/2005 | Triebel et al. |
| 7,070,785 B2 | 7/2006 | Lehner et al. |
| 7,125,843 B2 | 10/2006 | DeFrees et al. |
| 7,126,002 B2 | 10/2006 | Urogdi et al. |
| 7,148,239 B2 | 12/2006 | Vigh et al. |
| 7,326,574 B2 | 2/2008 | Boux et al. |
| 7,361,655 B2 | 4/2008 | Csakai et al. |
| 7,384,936 B2 | 6/2008 | Csakai et al. |
| 7,396,681 B1 | 7/2008 | Multhoff |
| 7,517,948 B2 | 4/2009 | Multhoff |
| 7,550,457 B2 | 6/2009 | Csakai et al. |
| 7,691,849 B2 | 4/2010 | Csakai et al. |
| 7,745,465 B2 | 6/2010 | Vigh et al. |
| 7,750,050 B2 | 7/2010 | Schuchman et al. |
| 2001/0034042 A1 | 10/2001 | Srivastava |
| 2002/0006410 A1 | 1/2002 | Lukacs et al. |
| 2002/0035072 A1 | 3/2002 | Fan et al. |
| 2002/0037290 A1 | 3/2002 | Armen |
| 2002/0039583 A1 | 4/2002 | Subjeck et al. |
| 2002/0095135 A1 | 7/2002 | Meeker et al. |
| 2002/0119163 A1 | 8/2002 | Srikumaran |
| 2002/0127219 A1 | 9/2002 | Okkels et al. |
| 2002/0127718 A1 | 9/2002 | Kuppner et al. |

(Continued)

FOREIGN PATENT DOCUMENTS

| | | |
|---|---|---|
| EP | 0751957 | 9/1995 |
| EP | 2145896 | 1/2010 |

(Continued)

OTHER PUBLICATIONS

Balogh et al.; The hyperfluidization of mammalian cell membranes acts as a signal to initiate the heat shock protein response. FEBS Journal 272 (2005) 6077-6086.

Botzler et al.; Synergistic effects of heat and ET-18-OCH3 on membrane expression of hsp70 and lysis of leukemic K562 cells. Experimental Hematology 27 (1999) 470-478.

Brunk et al.: Lysosomal involvement in apoptosis. Redox Rep. 2001; 6(2):91-7.

Brunk et al.: Photo-oxidative disruption of lysosomal membranes causes apoptosis of cultured human fibroblasts. Free Radical Biology & Medicine, vol. 23, No. 4, pp. 616-626, 1997.

Chung et al.; HSP72 protects against obesity-induced insulin resistance. PNAS Feb. 5, 2008 vol. 105, No. 5, 1739-1744.

(Continued)

*Primary Examiner* — David W Berke-Schlessel
(74) *Attorney, Agent, or Firm* — Dinsmore & Shohl LLP

(57) ABSTRACT

The present invention concerns a method for modulating the enzymatic activity of an enzyme, wherein said enzyme interacts with BMP, said method comprising the step of administering or inducing Hsp70, or a functional fragment or variant thereof, in a form suitable for allowing interaction between BMP and Hsp70, or said functional fragment or variant thereof, and thereby modulating the enzymatic activity of an enzyme interacting with BMP.

13 Claims, 16 Drawing Sheets

(56) References Cited

U.S. PATENT DOCUMENTS

| | | |
|---|---|---|
| 2002/0156250 A1 | 10/2002 | Wallen et al. |
| 2002/0172682 A1 | 11/2002 | Srivastava |
| 2002/0192230 A1 | 12/2002 | Srivastava |
| 2003/0012794 A1 | 1/2003 | Srivastava et al. |
| 2003/0035808 A1 | 2/2003 | Srivastava |
| 2003/0073094 A1 | 4/2003 | Young et al. |
| 2003/0129196 A1 | 7/2003 | Srivastava |
| 2003/0203846 A1 | 10/2003 | Srivastava et al. |
| 2003/0216315 A1 | 11/2003 | Nicchitta et al. |
| 2003/0236300 A1 | 12/2003 | Caplan et al. |
| 2004/0022796 A1 | 2/2004 | Srivastava |
| 2004/0047876 A1 | 3/2004 | Srivastava |
| 2005/0048608 A1 | 3/2005 | Chan et al. |
| 2005/0112640 A1 | 5/2005 | Davidson et al. |
| 2005/0153906 A1 | 7/2005 | Bedwell et al. |
| 2005/0202044 A1 | 9/2005 | Mizzen et al. |
| 2005/0267020 A1 | 12/2005 | Faure et al. |
| 2006/0089302 A1 | 4/2006 | Abulafia-Lapid et al. |
| 2006/0093612 A1 | 5/2006 | Srivastava |
| 2006/0264609 A1 | 11/2006 | Lehner et al. |
| 2006/0270833 A1 | 11/2006 | Henot et al. |
| 2007/0231337 A1 | 10/2007 | Multhoff |
| 2008/0009516 A1 | 1/2008 | Wustman |
| 2008/0014191 A1 | 1/2008 | Balch et al. |
| 2008/0019915 A1 | 1/2008 | Hadida-Ruah et al. |
| 2008/0026012 A1 | 1/2008 | Podack et al. |
| 2008/0039400 A1 | 2/2008 | Van Eden et al. |
| 2008/0132450 A1 | 6/2008 | Lee et al. |
| 2008/0161258 A1 | 7/2008 | Henning et al. |
| 2008/0305084 A1 | 12/2008 | Podsakoff et al. |
| 2009/0163500 A1 | 6/2009 | Lingwood et al. |
| 2009/0203605 A1 | 8/2009 | Segatori et al. |
| 2009/0208524 A1 | 8/2009 | Srivastava et al. |
| 2009/0298857 A1 | 12/2009 | Chiosis et al. |
| 2009/0318343 A1 | 12/2009 | Garigapati et al. |
| 2010/0004277 A1 | 1/2010 | Bulawa et al. |
| 2010/0087490 A1 | 4/2010 | Young |
| 2010/0130730 A1 | 5/2010 | Garigapati et al. |
| 2010/0168016 A1 | 7/2010 | Ackerman et al. |
| 2010/0196279 A1 | 8/2010 | Lockhart |
| 2010/0221225 A1 | 9/2010 | Byrne et al. |
| 2010/0266571 A1 | 10/2010 | Lockhart et al. |
| 2010/0317690 A1 | 12/2010 | Kawamura et al. |
| 2010/0329985 A1 | 12/2010 | Van Eden et al. |
| 2011/0027254 A1 | 2/2011 | Daniel et al. |
| 2011/0028403 A1 | 2/2011 | Le Poole et al. |
| 2011/0081428 A1 | 4/2011 | Lithgow et al. |
| 2011/0105560 A1 | 5/2011 | Wustman |
| 2011/0110938 A1 | 5/2011 | Chiu et al. |
| 2011/0123512 A1 | 5/2011 | Prahlad et al. |
| 2012/0115908 A1 | 5/2012 | Greensmith et al. |

FOREIGN PATENT DOCUMENTS

| | | |
|---|---|---|
| EP | 2318032 | 4/2012 |
| EP | 2484371 | 8/2012 |
| EP | 2659904 | 11/2013 |
| WO | WO-200117554 | 3/2001 |
| WO | WO-200134184 | 5/2001 |
| WO | WO-200152877 | 7/2001 |
| WO | WO-200152890 | 7/2001 |
| WO | WO-200234777 | 5/2002 |
| WO | WO-2003049692 | 6/2003 |
| WO | WO-2003/061684 | 7/2003 |
| WO | WO-2003086452 | 10/2003 |
| WO | WO-2005120558 | 12/2005 |
| WO | WO-2007041285 | 4/2007 |
| WO | WO-2007/150064 | 12/2007 |
| WO | WO-2008021210 | 2/2008 |
| WO | WO-2008112525 | 9/2008 |
| WO | WO-2008117026 | 10/2008 |
| WO | WO-2009095452 | 8/2009 |
| WO | WO-2009100037 | 8/2009 |
| WO | WO-2009137721 | 11/2009 |
| WO | WO-2009137796 | 11/2009 |
| WO | WO-2009141627 | 11/2009 |
| WO | WO-201015816 | 2/2010 |
| WO | WO-201022461 | 3/2010 |
| WO | WO-2010053655 | 5/2010 |
| WO | WO-2010086418 | 8/2010 |
| WO | WO-2010092112 | 8/2010 |
| WO | WO-2010102988 | 9/2010 |
| WO | WO-2010116141 | 10/2010 |
| WO | WO-2010148253 | 12/2010 |
| WO | WO-2011019763 | 2/2011 |
| WO | WO-2011075686 | 6/2011 |

OTHER PUBLICATIONS

Daugaard et al., "The heat shock protein 70 family: Highly homologous proteins with overlapping and distinct functions," FEBS Letters, Elsevier, Amsterdam, vol. 581, No. 19, Jul. 31, 2007, pp. 3702-3710.

Ferlinz et al.; Stimulation of lysosomal sphingomyelin degradation by sphingolipid activator proteins. Chemistry and Physics of Lipids 102 (1999) 35-43.

Fleshner & Johnson: Endogenous extra-cellular heat shock protein 72: Releasing signal(s) and function. Int. J. Hyperthermia, Aug. 2005; 21(5):457-471.

Gehrmann et al.; Differential Up-Regulation of Cytosolic and Membrane-Bound Heat Shock Protein 70 in Tumor Cells by Anti-Inflammatory Drugs. Clinical Cancer Research vol. 10, 3354-3364, May 15, 2004.

Gehrmann et al.; Effects of Antineoplastic Agents on Cytoplasmic and Membrane-Bound Heat Shock Protein 70 (Hsp70) Levels. Biol. Chem., vol. 383, pp. 1715-1725, Nov. 2002.

Gehrmann et al.; The therapeutic implications of clinically applied modifiers of heat shock protein 70 (Hsp70) expression by tumor cells. Cell Stress and Chaperones (2008) 13: 1-10.

Harada et al.: Heat shock proteins and the antitumor T cell response. Biotherapy 10: 229-235, 1998.

Kalmar & Greensmith; Activation of the heath shock response in a primary cellular model of motoneuron neurodegeneration—evidence for neuroprotective and neurotoxic effects. Cellular & Molecular Biology Letters vol. 14 (2009) pp. 319-335.

Kalmar et al.; Late stage treatment with arimoclomol delays disease progression and prevents protein aggregation in the SOC1G93A mouse model of ALS. Journal of Neurochemistry 2008, 107, 339-350.

Kalmar et al.; Upregulation of Heat Shock Proteins Rescues Motoneurons from Axotomy-Induced Cell Death in Neonatal Rats. Experimental Neurology 176, 87-97 (2002).

Kieran et al., Treatment with arimoclomol, a coinducer of heat shock proteins, delays disease progression in ALS mice, Nature Medicine, 10(4): 402-45, Apr. 2004.

Kirkegaard et al., Hsp70 stabilizes lysosomes and reverts Niemann-Pick disease-associated lysosomal pathology, Nature Letters, 463: 549-554, Jan. 28, 2010.

Kirkegaard-Sorensen et al., Interaction between Hsp70 and bis(monoacylglycero)phosphate stabilizes lysosomes and promotes cell survival, APMIS, 116(5): 436-437, May 2009.

Kirkegaard-Sorenson; Hsp70 binding to BMP—A novel mechanism for cellular protection. Dep. of Apoptosis, Danish Cancer Society, Feb. 2008. PhD Thesis. University of Copenhagen, Faculty of Health Sciences.

Kobayashi et al.: A lipid associated with the antiphospholipid syndrome regulates endosome structure and function. Nature Letters, 392:193-97, Mar. 12, 1998.

Kolzer et al.: Interactions of acid sphingomyelinase and lipid bilayers in the presence of the tricyclic antidepressant desipramine. FEBS Letters 559 (2004) 96-98.

Ng et al., Predicting deleterious amino acid substitutions. Genome Res. 2001 11: 863-874.

Nylandsted et al.: Heat shock protein 70 promotes cell survival by inhibiting lysosomal membrane permeabilization. J. Exp. Med. vol. 200, No. 4, Aug. 16, 2004 425-435.

Ohtsuka et al.; Inducers and co-inducers of molecular chaperones. Int. J. Hyperthermia, Dec. 2005; 21(8): 703-711.

(56) References Cited

OTHER PUBLICATIONS

Sambrook et al., Molecular Cloning, A Laboratory Manual, Cold Spring Harbor, Laboratory Press (1998), 1.101-1.104.
Tavaria et al.: A hitchhiker's guide to the human Hsp70 family. Mini-review. Cell stress & Chaperones (1996) 1 (1), 23-28.
Tidwell et al.: Administration of Hsp70 in vivo inhibits motor and sensory neuron degeneration. Cell Stress & Chaperones (2004) 9(1), 88-98.
Tytell & Hooper; Heat Shock proteins: new keys to the development of cytoprotective therapies. Expert Opin Ther Targets, Apr. 2001;5(2):267-87.
Tytell: Release of heat shock proteins (Hsps) and the effects of extracellular Hsps on neural cells and tissues. Int J Hypothermia, Aug. 2005; 21(5): 445-455.
Torok et al.; Heat shock protein coinducers with no effect on protein denaturation specifically modulate the membrane lipid phase. PNAS Mar. 18, 2003, vol. 100, No. 6, 3131-3136.
Vigh et al., Bimoclomol: A nontoxic, hydroxylamine derivative with stress protein-inducing activity and cytoprotective effects, Nature Medicine, 3(10): 1150-54, Oct. 1997.
Vigh et al.; Can the stress protein response be controlled by membrane-lipid therapy? Trends in Biochemical Sciences vol. 32 No. 8 (2007).
Wei et al.: Inhibition of proliferation and induction of apoptosis by abrogation of heat-shock protein (HSP) 70 expression in tumor cells. Cancer Immunol. Immunother. (1995) 40:73-78.
Yu et al.: Retinal uptake of intravitreally injected Hsc/Hsp70 and its effects on susceptibility to light damage. Molecular Vision 2001; 7:48-56.
Zhu, Y. et al. "Dexmethasone-mediated up-regulation of the mannose receptor improves the delivery of recombinant glucocerebrosidase to Gaucher macrophages," The Journal of Pharmacology and Experimental Therapeutics, 308(2): 705-711, Feb. 2004.
Communication Pursuant to Article 94(3) EPC for Application No. 09768858.4 dated Jul. 26, 2011.
Du, W. et al., Cell Growth Inhibition by Farnseyltransferase Inhibitors is Mediated by Gain of Geranylgeranylated RhoB, Molecular and Cellular Biology, 19(3): 1831-40, Mar. 1999.
Prendergast, G. et al., Farnesyltransferase Inhibition Causes Morphological Reversion of ras-Transformed Cells by a Complex Mechanism that Involves Regulation of the Actin Cytoskeleton, Molecular and Cellular Biology, 14(6): 4193-4202, Jun. 1994.
Balabanov, S. et al., Quantitative proteomics analysis of BMS-214662 effects on CD34 positive cells from chronic myeloid leukaemia patients, Proteomics, 13: 153-68, 2013.
Mazieres, J. et al., Perspectives on farnesyl transferase inhibitors in cancer therapy, Cancer Letters, 206: 159-67, 2004.
Porcu, G. et al., A yeast-based genomic strategy highlights the cell protein networks altered by FTase inhibitor peptidomimetics, Molecular Cancer, 9: 197, 2010.
Horvath, I. et al., Membrane-associated stress proteins: More than simply chaperones, Biochimica et Biophysica Acta, 1778: 1653-64, 2008.
Simons, K. et al., Jamming the Endosomal System: Lipid Rafts and Lysosomal Storage Diseases, Trends in Cell Biology, 10: 459-62, 2000.
Hu, W. et al., Proteomic identification of heat shock protein 70 as a candidate target for enhancing apoptosis induced by farnesyl transferase inhibitor, Proteomics, 3: 1904-11: 2003.

Jaatela, M. et al., Emerging Role of Heat Shock Proteins in Biology and Medicine, Annals of Medicine, 24: 249-58, 1992.
Goni, F. et al., Sphingomyelinases: enzymology and membrane activity, Federation of European Biochemical Societies, 531: 38-46, 2002.
Roth, A. et al., Interaction between Hsp70 and bis(monoacylglycero)phosphate stabilizes lysosomes and promotes cell survival, APMIS, 116: 437, 2008.
Yenari, M. et al., The neuroprotective potential of heat shock protein 70 (HSP70), Molecular Medicine Today, 5: 525-31, 1999.
Keeling et al., Gentamicin-mediated suppression of Hurler syndrome stop mutations restores a low level of alpha-L-iduronidase activity and reduces lysosomal glycosaminoglycan accumulation, Human Molecular Genetics, 10: 291-99, 2001.
Meikle et al., Effect of lysosomal storage on bis(monoacylglycero)phosphate, Biochem J., 411: 71-78, 2008.
Voellmy et al., Isolation and functional analysis of a human 70,000-dalton heat shock protein gene segment, Proc. Natl. Acad. Sci. USA, 82: 4949-53, 1985.
Wu, et al., Structure and expression of the human gene ancoding major heat shock protein HSP70, Mol. Cell. Biol., 5(2): 330-41, 1985.
Winchester, B. et al., The molecular basis of lysosomal storage disease, Biochemical Society Transactions, 28: 150-54, 2000.
Kalmar et al. The effect of treatment with BRX-220, a co-inducer of heat shock proteins, on sensory fibors of the rat following peripheral nerve injury, Exp. Neurol., 184: 636-647, 2003.
Rakonczay et al., Nontoxic heat shock protein coinducer BRX-220 protects against acute pancreatitis in rats, Free Radical Biology and Medicine, 32(12): 1283-1292, 2002.
Au, Q. et al., High-content image-based screening for small-molecule chaperone amplifiers in heat shock, Journal of Biomolecular Screening, 13(19): 953-959, 2008.
Bruening, W. et al., Up-regulation of protein chaperones preserves viability of cells expressing toxic Cu/Zn-superoxide dismutase mutants associated with amyotrophic lateral sclerosis, Journal of Neurochemistry, 72: 693-99, 1999.
Horváth, I. et al., Cell biology: Stability in times of stress, Nature, 463(7280): 436-438, 2010.
Polakowski, J. et al., Bimoclomol elevates heat shock protein 70 and cytoprotects rat neonatal cardiomyocytes, European Journal of Pharmacology, 435: 73-77, 2002.
Hallows, J. et al., p35/p25 Is Not Essential for Tau and Cytoskeletal Pathology or Neuronal Loss in Niemann-Pick Type C Disease, The Journal of Neuroscience, 26: 2738-2744, 2006.
Parfitt, D. et al., The heat-shock response co-inducer arimoclomol protects against retinal degeneration in rhodopsin retinitis pigmentosa, Cell Death and Disease, 5: 1-10, 2014.
Patterson, M. et al., Miglustat for treatment of Niemann-Pick C disease: a randomised controlled study, Lancet Neurology, 6: 765-772, 2007.
Kabakov, A. et al., Pharmacological attenuation of apoptosis in reoxygenated endothelial cells, Cellular and Molecular Life Sciences, 61: 3076-86, 2004.
Cohen, F. et al., Therapeutic approaches to protein-misfolding diseases, Nature, 426:905-909, 2003.
Freeman, B. et al., The human cytosolic molecular chaperones hsp90 (hsc70) and hdj-1 have distinct roles in recognition of a non-native protein and protein refolding, The European Molecular Biology Journal, 15: 2969-79, 1996.

USE OF HSP70 AS A REGULATOR OF ENZYMATIC ACTIVITY

REFERENCE TO RELATED APPLICATIONS

This application is a divisional of U.S. patent application Ser. No. 13/969,944, filed Aug. 19, 2013, which is a continuation of U.S. patent application Ser. No. 13/001,316, filed Dec. 23, 2010, now U.S. Pat. No. 8,540,985, which is a U.S. national phase of PCT/DK2009/050151, filed Jun. 26, 2009, which is a non-provisional application of DK patent application PA 2008 00885, filed Jun. 26, 2008. The entire content of each application is incorporated herein by reference.

FIELD OF THE INVENTION

The present invention relates to the field of modulation of enzyme activity by exploiting the interaction between the molecular chaperone Hsp70 and the lysosomal phospholipid Bis(monoacylglycero)phosphate (BMP, also known under the nome LBPA). The Hsp70-BMP interaction modulates the activity of BMP-interacting enzymes of the lysosomal compartment, and the present invention thus provides a means for reversing the pathology of lysosomal storage diseases.

BACKGROUND OF THE INVENTION

The molecular chaperones are found in all compartments of a cell where conformational rearrangements of proteins occur, and although protein synthesis is the major source of unfolded peptides in the cell, a challenge to the cell by high temperature or other stimuli that might render proteins structurally labile, and hence prone to unfolding and aggregation, is met with a specific cellular response involving the production of protective proteins. This response is a phenomenon observed in every cell type ranging from prokaryotes to eukaryotes and is referred to as the heat-shock- or stress-response. The proteins induced by this response are known as the heat shock proteins (HSPs), of which there exist several families.

A primary example of a family of chaperones is the Hsp70 proteins. This family has recently been implicated in other aspects of cellular homeostasis besides serving as a chaperone—most markedly through its anti-apoptotic features, its functions in immunity, and the apparent dependence of cancer cells on the upregulation of Hsp70. Furthermore, Hsp70 can serve a role in safeguarding lysosomal integrity. However, the molecular mechanism therefore has remained unclear.

The lysosomal storage diseases are a rare group of diseases, characterized by the accumulation of substances in the lysosomal compartment and resulting destabilization hereof, with a resulting devastating effect for affected individuals. Substances accumulate in the lysosomal compartment due to deficiencies in the enzymes involved in their catabolism.

To this date, no treatment is available for most lysosomal storage diseases. The underlying cause of this group of diseases is the inability of specific lysosomal enzymes to catabolize efficiently specific lysosomal substances such as lipids. Therefore the use of enzyme replacement therapy (ERT), by providing to a patient the recombinant enzyme, has been employed for a subset of these diseases, including Gaucher and Fabry disease. However, ERT is a very expensive form of therapy which may limit its use in some areas, and also is effective only towards the specific type of disease to which the recombinant enzyme has been produced. The present invention is aimed at providing new means for treating the lysosomal storage disorders.

SUMMARY OF THE INVENTION

In the present invention, the molecular basis for the contribution of Hsp70 to lysosomal membrane stability is disclosed by providing an understanding of the molecular basis for the association between Hsp70 and cellular membranes—in particular plasma—and lysosomal membranes.

It is known from the literature that Hsp70 can serve a role in safeguarding lysosomal integrity. However, the molecular mechanism has remained unclear. In addition, the question as to whether this attribute is specific for the major stress-inducible Hsp70 (HspA1A/A1B—named Hsp70 throughout this study) or whether other Hsp70 family members could have the same characteristic, had not been addressed either.

These unanswered questions prompted one of the major aims of this invention, which was to investigate the molecular basis for the lysosome-protective effect of Hsp70. To this end, a method for the production of recombinant Hsp70 and mutants hereof was set up, as was a subcellular fractionation protocol based on iodixanol gradient ultracentrifugation. An assay for the direct assessment of lysososomal membrane integrity was established based on photooxidation-induced permeabilization of lysosomes, which allowed a real-time microscopic approach to evaluate the effect of Hsp70 and other components with regard to their ability to either sensitize or protect the lysosomal membranes. The interaction of recombinant Hsp70 and mutants with various lipids was investigated in different in vitro systems including measurements of liposome 90° light scattering, tryptophan fluorescence shifts and surface plasmon resonance (BIAcore). The creation of a conceptual model for the Hsp70-BMP interaction was aided by in silico electrostatic surface modeling of Hsp70. In order to verify the in vivo relevance of the lipid interaction witnessed in the in vitro systems, the BMP-Hsp70 interaction was targeted with regard to both components. To further show the feasibility of exploiting this mechanism, the mode of cell death induced by administration of cisplatin was characterized, and lysosomal Hsp70 was targeted in this cell death system both in cancer as well as in non-transformed cell lines.

In order to address the molecular basis for Hsp70's contribution to lysosomal membrane stability, the inventors sought to establish a system which would eliminate the influence of cytosolic Hsp70, i.e. targeting Hsp70 directly to the lysosomes was needed. Electron microscopy pictures by Nylandsted et al. showed that Hsp70 could be present inside the lysosomes, and it was thus decided to establish a method for the production of recombinant human Hsp70 (rHsp70) and hopefully exploit the endocytic machinery as a delivery pathway of the rHsp70 directly to the lysosomes. The present inventors would hereby bypass the need for adding lysosomal sorting signals to Hsp70, potentially disrupting function and avoiding complications that might arise due to overexpression. An endocytic approach would furthermore allow a titration of the amounts of rHsp70 and in a longer perspective open possibilities for studying the mechanism for uptake of extracellular Hsp70.

Having established the method for production of Hsp70, it was then tagged with the fluorophore Alexa Fluor 488 (Hsp70-AF488) in order to validate its endocytosis. Confocal imaging revealed that rHsp70 could indeed be targeted to lysosomes in this way. In order to assess the impact on lysosomal membrane stability, the inventors next set up a method for quantifying lysosomal membrane permeabilization at the level of single lysosomes and utilized this method to evaluate the effect of endocytosed rHsp70. These methods formed the basis for Examples 1 and 2, in which the inventors show that Hsp70 enhances cell survival by stabilizing lysosomes through a pH-dependent high affinity binding to the endo-lysosomal anionic phospholipid bis(monoacyl-glycero)phosphate (BMP). The positively charged ATPase domain of Hsp70 is responsible for the binding but the substrate-binding domain is also required for effective stabilization of lysosomes. Interestingly, this interaction, and the protection it offers, is dependent on tryptophan 90, which is located in the positively charged wedge of the ATPase domain. Importantly, the cytoprotective effect could be obtained by endocytic delivery of rHsp70 and specifically reverted by extracellular administration of BMP antibodies or Hsp70 inhibitors.

In addition to this, the inventors also sought to couple the mechanism for Hsp70's protection of lysosomal membranes to the events of tumorigenesis and programmed cell death. The inventors thus characterized the cell death program initiated by the administration of a common chemotherapeutic agent, cisplatin and found it to be independent of caspases, but characterized by lysosomal release of proteases. Transgenic as well as endocytosed Hsp70 is capable of enhancing cell survival in the face of cisplatin-challenge by stabilizing the lysosomal membranes. Interestingly, the inventors show that either targeting lysosomal Hsp70 itself or its lysosomal interaction partner bis(monoacyl-glycero) phosphate (BMP), sensitize transformed, but not non-transformed, prostate cell lines to cisplatin which provides experimental evidence for exploiting the BMP-Hsp70 interaction as a pharmacological target for cancer therapy.

Interestingly Hsp70-2, although sharing 86% amino acid homology with Hsp70, was not capable of protecting the lysosomal membranes directly. However, the depletion of Hsp70-2 also results in lysosomal membrane permeabilization and ensuing programmed cell death. This effect does not depend on a direct interaction between Hsp70-2 and the lysosomal compartment, but is rather orchestrated via the down-regulation of Lens Epithelium Derived Growth Factor (LEDGF), in response to Hsp70-2 depletion.

The methods and results of this investigation are addressed in more detail in the Examples section.

Having elucidated herein the molecular basis of the cytoprotective effect of Hsp70 via an interaction with lysosomal BMP to promote lysosomal stabilization, these findings provide the basis for the therapeutic targeting of lysosomal storage diseases.

It has now been demonstrated that surprisingly, providing recombinant Hsp70 to cells efficiently reverts the pathology of lysosomal storage diseases, as shown herein for Niemann-Pick disease and Farber disease. Further, providing the Hsp70 inducer benzyl alcohol to cells efficiently reverts the pathology of lysosomal storage diseases, as shown herein for Niemann-Pick disease.

The present invention thus provides a method for treating lysosomal storage diseases by increasing directly or indirectly the intracellular concentration and/or activity of Hsp70 in individuals in need thereof, by providing Hsp70, or a functional fragment or variant thereof, or by providing a Hsp70 inducer or co-inducer.

The present invention relates in one aspect to a bioactive agent capable of increasing the intracellular concentration and/or activity of Hsp70 for use as a medicament or for use in the treatment of a lysosomal storage disorder.

In one embodiment, said bioactive agent is Hsp70, or a functional fragment or variant thereof.

In another embodiment, said bioactive agent is an Hsp70 inducer or co-inducer.

It is also an aspect of the present invention to provide a method for treatment of a lysosomal storage disease comprising administration of the bioactive agent according to the present invention to an individual in need thereof.

In one embodiment, said treatment is prophylactic, curative or ameliorating.

In one embodiment, said lysosomal storage disease is selected from the group consisting of Niemann-Pick disease, Farber disease, Krabbe disease, Fabry disease, Gaucher disease, Sialidosis, Metachromatic leukodystrophy and saposin-deficiency.

In another embodiment, said lysosomal storage disease is characterised as having residual enzymatic activity of the defective enzyme involved in the disease pathology.

The present invention also relates to a method of treatment of a lysosomal storage disease comprising administration of the bioactive agent according to the present invention in combination with at least one other treatment modality.

A further aspect of the present invention is to provide a method for modulating the enzymatic activity of an enzyme, wherein said enzyme interacts with BMP (bis(monoacyl-glycero)phosphate), said method comprising the steps of
 i) administering the bioactive agent according to the present invention,
 ii) allowing interaction between BMP and Hsp70, and
 iii) modulating the enzymatic activity of an enzyme interacting with BMP.

In another aspect, the present invention relates to Hsp70, or a functional fragment or variant thereof, for use as a medicament.

In one aspect, the present invention concerns a method for modulating the enzymatic activity of an enzyme, wherein said enzyme interacts with BMP, said method comprising the step of administering Hsp70, or a functional fragment or variant thereof, in a form suitable for allowing interaction between BMP and Hsp70, or said functional fragment or variant thereof, and thereby modulating the enzymatic activity of an enzyme interacting with BMP.

Preferably, Hsp70 or said functional fragment or variant thereof forms a covalent or non-covalent complex with BMP.

Preferably, BMP interacts with a saposin.

Preferably, said saposin is selected from the group consisting of saposin A, saposin B, saposin C, and saposin D.

Preferably, said enzyme is selected from the group consisting of sphingomyelinase, acidic sphingomyelinase, sialidase, alpha-galactosidase, beta-galactosidase, beta-galactosylceramidase, glucosylceramidase, and acid ceramidase.

Preferably said modulation of the enzymatic activity is an up-regulation of the enzymatic activity of said enzyme.

In another aspect, the present invention concerns Hsp70, or a functional fragment or variant thereof, for use as a medicament. Preferably, said Hsp70, or a functional fragment or variant thereof, may be used in the treatment, alleviation, or prophylaxis of a lysosomal storage disorder, such as the disorders Niemann-Pick, Gaucher, Farber, Krabbe, Fabry, and Sialidosis.

In another aspect, the invention concerns a method for increasing the uptake of a compound, said method comprising the step of administering said compound together with Hsp70 or a functional fragment or variant thereof. In one embodiment, said Hsp70 or a functional fragment or variant thereof is covalently bound to said compound. In another embodiment, said Hsp70 or a functional fragment or variant thereof is non-covalently bound to said compound.

An embodiment of the invention concerns a method for up-regulation of an enzymatic activity of an enzyme associated with a lysosomal storage disorder, such as Niemann-Pick, Gaucher, Farber, Krabbe, Fabry, and Sialidosis. Preferably, said lysosomal storage disorder is Niemann-Pick.

Since the lysosomal storage disorders are caused by insufficient enzymatic activity, it is the aim of the invention to increase the enzymatic activity in order to alleviate or cure the disorder.

Hsp70 has been shown to interact with BMP. Since BMP acts as a co-factor for various other proteins, the interaction between Hsp70 and BMP may modulate the function of these various other proteins. For instance, BMP acts as a co-factor for aSMase. Thus, the interaction between Hsp70 and BMP may increase the activity of aSMase. Since Niemann-Pick disorder is associated with a decreased aSMase activity, Hsp70 may alleviate or cure Niemann-Pick disorder by increasing the activity of aSMase. Similarly, BMP acts as a co-factor for the saposin A, saposin, B, saposin C, and saposin D. These saposin proteins are implicated in other lysosomal storage disorders, and therefore Hsp70 may alleviate or cure other lysosomal storage disorders by increasing the activity of a saposin or of an enzyme associated with said saposin.

In an embodiment of the invention, Hsp70 is administered together with enzyme replacement therapy in the treatment of a lysosomal storage disorder. In this manner, the amount of enzyme necessary may be significantly reduced due to the enzyme-activating effect of Hsp70.

In another embodiment, Hsp70 is used to facilitate uptake of enzymes in enzyme replacement therapy, thereby increasing the amount of enzyme having been taken up by the relevant cells.

DEFINITIONS AND ABBREVIATIONS aSMase/ASM Acidic sphingomyelinase
ADD70: AIF-derived decoy for Hsp70
AIF: Apoptosis inducing factor
AO: Acridine Orange
Apaf-1: Apoptotic protease activating factor-1
Bag-1: Bcl-2 associated athanogene-1
Bcl-2: B-cell lymphoma/leukaemia 2
Bid: BH3 interacting domain death agonist
BMP: Bis(monoacylglycero)phosphate
CARD: Caspase recruitment domain
Caspase: Cysteine aspartate-specific protease
CHIP: Carboxy terminus of Hsp70-binding protein
CytC: Cytochrome C
DD: Death domain
DED: Death effector domain
dsRNA: double-stranded RNA
eHsp70: extracellular Hsp70
ER: Endoplasmic reticulum
ERT Enzyme replacement therapy
FADD: Fas-associated death-domain containing protein
HIP: Hsp70 interacting protein
HRP: Horse radish peroxidase
HS: Heat shock/stress
HSE: Heat shock element
HSF: Heat shock factor
Hsp: Heat shock protein
HspBP1: Heat ahock protein Binding Protein 1
IAP: Inhibitor of apoptosis protein
iMEF immortalized Murine Embryonic Fibroblasts JNK: c-jun NH2-terminal kinase
LAMP-1/-2: Lysosome-associated membrane protein-1/-2
LBPA: Lysobisphosphatidic acid
LEDGF: Lens epithelium derived growth factor
LMP: Lysosomal membrane permeabilization
MIC-1: Macrophage inhibitory cytokine 1
MOMP: Mitochondrial outer membrane permeabilization
MPR Mannose 6-phosphate receptor
MTT: 3-(4,5-Dimethyl-2-thiazolyl)-2,5-diphenyl-2H-tetrazolium bromide
NPD Niemann-Pick disease
NPDA Niemann-Pick disease, type A
NPDB Niemann-Pick disease, type B
NPDC Niemann-Pick disease, type C
NPDD Niemann-Pick disease, type D
PCD: Programmed cell death
PKC: Protein kinase C
POPC: Palmitoyl-oleoyl-phosphatidylcholine
POPS: Palmitoyl-oleoyl-phosphatidylserine
RNAi: RNA interference
ROS: Reactive oxygen species
SD: Standard deviation
siRNA: Short interfering RNA
Smac/Diablo: Second mitochondrial-derived activator of caspases
tBid: Truncated Bid
TNF: Tumour necrosis factor
TNFR: TNF-receptor
TRADD: TNFR associated death domain protein
TRAF: TNFR associated factor Lysosomal storage disorder (LSD): The terms "lysosomal storage disorder" and "lysosomal storage disease" are used as synonyms.

Functional fragment of Hsp70: The term "functional fragment of Hsp70" is to be construed as meaning any fragment of Hsp70 having the desired function. In relation to modulation of enzymatic activity, a functional fragment is a fragment capable of modulating the enzymatic activity. In relation to increasing the uptake of a substance, a functional fragment of Hsp70 is a fragment capable of increasing the uptake of said substance. It is appreciated that the exact quantitative effect of the functional fragment may be different from the effect of the full-length molecule. In some instances, the functional fragment may indeed be more effective than the full-length molecule. Furthermore, the use of fragments instead of full-length molecules may be advantageous in view of the smaller size of the fragments.

Functional variant of Hsp70: The term "functional variant of Hsp70" is to be construed as meaning any variant of Hsp70 having the desired function. In relation to modulation of enzymatic activity, a functional variant is a variant capable of modulating the enzymatic activity. In relation to increasing the uptake of a substance, a functional variant of Hsp70 is a fragment capable of increasing the uptake of said substance. It is appreciated that the exact quantitative effect of the functional variant may be different from the effect of the full-length molecule. In some instances, the functional variant may indeed be more effective than the full-length molecule.

A "Bioactive agent" (i. e., biologically active substance/agent) is any agent, drug, compound, composition of matter or mixture which provides some pharmacologic, often beneficial, effect that can be demonstrated in vivo or in vitro. As used herein, this term further includes any physiologically or pharmacologically active substance that produces a localized or systemic effect in an individual. Further examples of bioactive agents include, but are not limited to, agents comprising or consisting of an oligosaccharide, agents comprising or consisting of a polysaccharide, agents comprising or consisting of an optionally glycosylated peptide, agents comprising or consisting of an optionally glycosylated polypeptide, agents comprising or consisting of a nucleic acid, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites. It may be used either prophylactically, therapeutically, in connection with treatment of an individual, such as a human or any other animal. As used herein, a bioactive agent is a substance capable of increasing the intracellular concentration and/or activity of Hsp70.

The terms "drug" or "medicament" as used herein includes biologically, physiologically, or pharmacologically active substances that act locally or systemically in the human or animal body.

The terms "treating", "treatment" and "therapy" as used herein refer equally to curative therapy, prophylactic or preventative therapy and ameliorating or palliative therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

"Pharmacologically effective amount", "pharmaceutically effective amount" or "physiologically effective amount of a "bioactive agent" is the amount of an active agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered. The precise amount will depend upon numerous factors, e.g., the active agent, the activity of the composition, the delivery device employed, the physical characteristics of the composition, intended patient use (i.e. the number of doses administered per day), patient considerations, and the like, and can readily be determined by one skilled in the art, based upon the information provided herein. An "effective amount" of a bioactive agent can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 100%.

"Co-administering" or "co-administration" of bioactive agent(s), or bioactive agents and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 72 hours, such as 48 hours, for example less than 24 hours, such as less than 12 hours, for example less than 6 hours, such as less than 3 hours. However, these terms also mean that the bioactive agent and a therapeutic composition can be administered together.

The term "Individual" refers to vertebrates, in particular a member of a mammalian species, preferably primates including humans. In a preferred embodiment, an individual as used herein is a human being, male or female, of any age.

An "individual in need thereof" refers to an individual who may benefit from the present invention. In one embodiment, said individual in need thereof is a diseased individual, wherein said disease is a lysosomal storage disease.

The term "natural nucleotide" or "nucleotide" refers to any of the four deoxyribonucleotides, dA, dG, dT, and dC (constituents of DNA), and the four ribonucleotides, A, G, U, and C (constituents of RNA), as found in nature. Each natural nucleotide comprises or essentially consists of a sugar moiety (ribose or deoxyribose), a phosphate moiety, and a natural/standard base moiety. Natural nucleotides bind to complementary nucleotides according to well-known rules of base pairing (Watson and Crick), where adenine (A)

pairs with thymine (T) or uracil (U); and where guanine (G) pairs with cytosine (C), wherein corresponding base-pairs are part of complementary, anti-parallel nucleotide strands. The base pairing results in a specific hybridization between predetermined and complementary nucleotides. The base pairing is the basis by which enzymes are able to catalyze the synthesis of an oligonucleotide complementary to the template oligonucleotide. In this synthesis, building blocks (normally the triphosphates of ribo or deoxyribo derivatives of A, T, U, C, or G) are directed by a template oligonucleotide to form a complementary oligonucleotide with the correct, complementary sequence. The recognition of an oligonucleotide sequence by its complementary sequence is mediated by corresponding and interacting bases forming base pairs. In nature, the specific interactions leading to base pairing are governed by the size of the bases and the pattern of hydrogen bond donors and acceptors of the bases. A large purine base (A or G) pairs with a small pyrimidine base (T, U or C). Additionally, base pair recognition between bases is influenced by hydrogen bonds formed between the bases. In the geometry of the Watson-Crick base pair, a six membered ring (a pyrimidine in natural oligonucleotides) is juxtaposed to a ring system composed of a fused, six membered ring and a five membered ring (a purine in natural oligonucleotides), with a middle hydrogen bond linking two ring atoms, and hydrogen bonds on either side joining functional groups appended to each of the rings, with donor groups paired with acceptor groups.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g. alpha-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes e.g. so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues preferably joined exclusively by peptide bonds, whether produced naturally or synthetically. A polypeptide produced by expression of a non-host DNA molecule is a "heterologous" peptide or polypeptide. The term "polypeptide" as used herein covers proteins, peptides and polypeptides, wherein said proteins, peptides or polypeptides may or may not have been post-translationally modified. Post-translational modification may for example be phosphorylation, methylation and glycosylation.

The term "expression" refers to the biosynthesis of a gene or a gene product.

To "hybridize" means annealing nucleic acid strands from different sources; that is, to form base pairs between complementary regions of two strands of DNA that were not originally paired. The term "hybridization under stringent conditions" is defined according to Sambrook et al., Molecular Cloning, A Laboratory Manual, Cold Spring Harbor, Laboratory Press (1989), 1.101-1.104. Preferably, hybridization under stringent conditions means that after washing for 1 h with 1 times SSC and 0.1% SDS at 50 degree C., preferably at 55 degree C., more preferably at 62 degree C. and most preferably at 68 degree C., particularly for 1 h in 0.2 times SSC and 0.1% SDS at 50 degree C., preferably at 55 degree C., more preferably at 62 degree C. and most preferably at 68 degree C., a positive hybridization signal is observed.

A stretch of "Complete homology" is defined as a match of pairing nucleotides along the sequence of the interacting nucleotides; in natural occurring RNA the pairing of A with U and G with C.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. If a promoter is an inducible promoter, then the rate of transcription increases in response to an inducing agent. In contrast, the rate of transcription is not regulated by an inducing agent if the promoter is a constitutive promoter. Repressible promoters are also known.

A "regulatory element" is a nucleotide sequence that modulates the activity of a promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

A "cloning vector" is a nucleic acid molecule, such as a plasmid, cosmid, or bacteriophage that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. Simpler vectors called "transcription vectors" are only capable of being transcribed but not translated: they can be replicated in a target cell but not expressed, unlike expression vectors. Transcription vectors are used to amplify their insert.

A "recombinant host" is a cell that contains a heterologous nucleic acid molecule, such as a cloning vector or expression vector.

Transfection describes the introduction of foreign material into eukaryotic cells. The term 'transfection' for non-viral methods is most often used in reference to mammalian cells, while the term 'transformation' is preferred to describe non-viral DNA transfer in bacteria and non-animal eukaryotic cells such as fungi, algae and plants. Both chemical and physical methods may be employed to transfect cells.

A "polypeptide" is a polymer of amino acid residues preferably joined exclusively by peptide bonds, whether produced naturally or synthetically. A polypeptide produced by expression of a non-host DNA molecule is a "heterologous" peptide or polypeptide. The term "polypeptide" as used herein covers proteins, peptides and polypeptides, wherein said proteins, peptides or polypeptides may or may not have been post-translationally modified. Post-translational modification may for example be phosphorylation, methylation and glucosylation.

An "amino acid residue" can be a natural or non-natural amino acid residue linked peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids.

Natural amino acids of standard nomenclature as listed in J. Biol. Chem., 243:3552-59 (1969) and adopted in 37 C.F.R., section 1.822(b)(2) belong to the group of amino acids listed in Table 1 herein below. Non-natural amino acids are those not listed in Table 1. Examples of non-natural amino acids are those listed e.g. in 37 C.F.R. section 1.822(b)(4), all of which are incorporated herein by reference. Also, non-natural amino acid residues include, but are not limited to, modified amino acid residues, L-amino acid residues, and stereoisomers of D-amino acid residues.

TABLE 1

Natural amino acids and their respective codes.

| Symbols | | |
| --- | --- | --- |
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers in one embodiment to the following classes: 1) HRK, 2) DENQ, 3) C, 4) STPAG, 5) MILV and 6) FYW Within the meaning of the term "equivivalent amino acid substitution" as applied herein, one amino acid may be substituted for another, in one embodiment, within the groups of amino acids indicated herein below:

i) Amino acids having polar side chains (Asp, Glu, Lys, Arg, His, Asn, Gin, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

The present invention also relates to variants of Hsp70, or fragments thereof, wherein the substitutions have been designed by computational analysis that uses sequence homology to predict whether a substitution affects protein function (e.g. Pauline C. Ng and Steven Henikoff, Genome Research, Vol. 11, Issue 5, 863-874, May 2001).

Due to the imprecision of standard analytical methods, molecular weights and lengths of polymers are understood to be approximate values. When such a value is expressed as "about" X or "approximately" X, the stated value of X will be understood to be accurate to +/−20%, such as +/−10%, for example +/−5%.

Ribbon and Molecular surface models of the ATPase domain of Hsp70. ATP (van der Waal-surface representation) can be visualized bound in the ATP-binding pocket. Green and purple spheres denote the van der Waals-surface of the coordinated Calcium and Sodium ions, respectively. Notice the positively charged part of the domain in the bottom and the position of W90.

The values represent means±SD for a minimum of five independent experiments (b, c, f and g).

FIG. 7

Hsp70 stimulates ASM activity that in turn stabilizes lysosomes. (a) Biacore measurement of binding of 200 nM rASM to BMP-containing liposomes at pH 4.5 as a function of pre-bound rHsp70. The experiments were performed as described in the legend for FIG. 6e with rASM added for 180 sec after the 10 min rHsp70-dissociation phase followed by yet a 10 min dissociation phase. (b) ASM activity in the lysates of wild-type (WT) and Hsp70 transgenic (Hsp70) MEFs (left panel) and in WT MEFs incubated with 300 nM rHsp70 for 24 or 48 h as indicated. (c and d) Viability (MTT reduction; c) and cytosolic cathepsin activity (zFRase; d) in WT and Hsp70 iMEFs treated with indicated concentrations of desipramine for 3 h. (e) Live single-cell imaging of loss of lysosomal integrity (photo-oxidation in WT and Hsp70 MEFs as well as Hsp70 MEFs incubated for 3 h with 12.5 and 25 µM Desipramine (left and right panels, respectively). Loss of red (left panel) and increase in green fluorescence (right panel) was continuously measured to give full kinetic curves for the loss of lysosomal integrity. 25-60 cells were examined pr. experiment from pre-defined areas), $p<0.001$ for Hsp70 vs. WT and Hsp70+despramine vs. Hsp70. All values represent means±SD for a minimum of 3 independent experiments.

Figure 1:
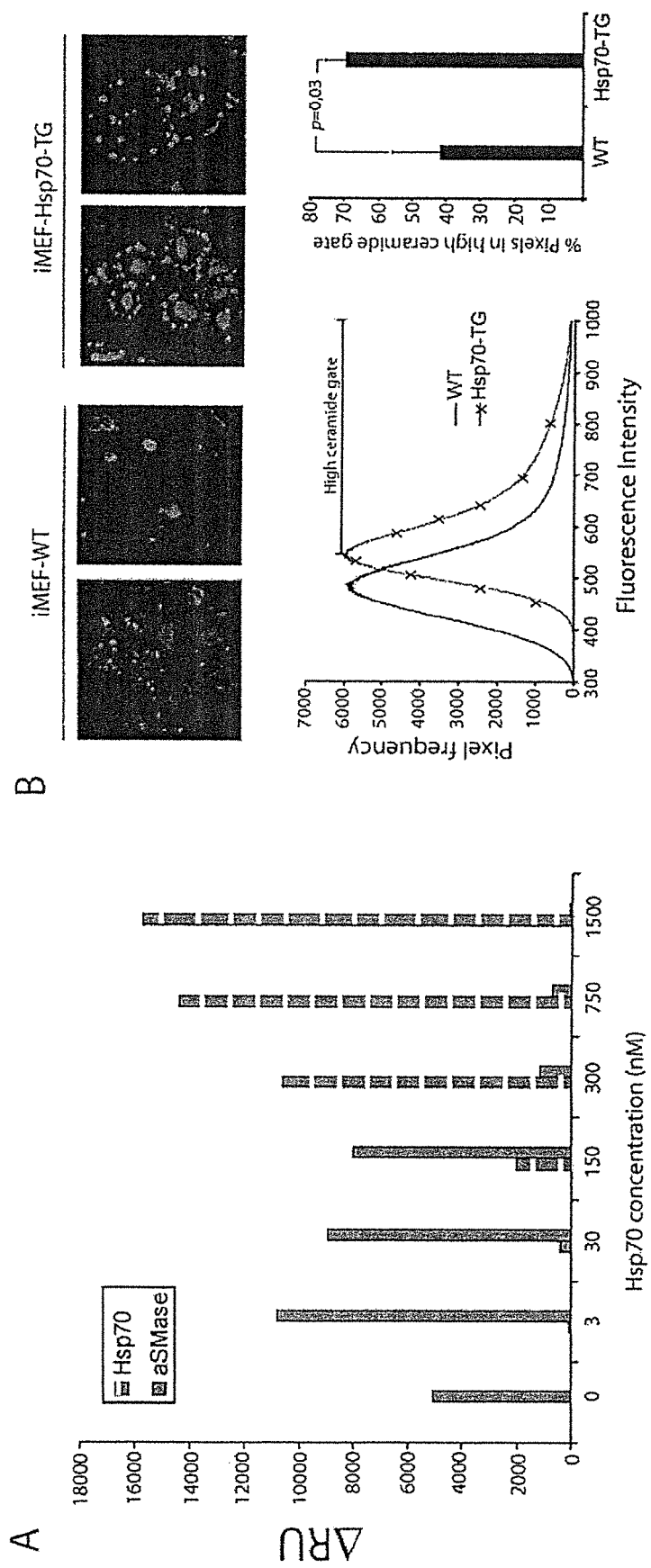
FIG. 1
The effects of Hsp70 on aSMase binding to BMP and ceramide levels. (A) Binding of 0.2 μM aSMase to BMP-containing liposomes at pH 4.5 as a function of pre-bound Hsp70 (experiment analogous to Example 1, see materials and methods herein for further details). Hsp70 was allowed to dissociate for 10 min, hereby reaching a lower asymptote for dissociation before addition of aSMase). (B) Confocal microscopy and quantification of ceramide levels in wild-type (WT) and Hsp70-transgenic (Hsp70-TG) iMEFs. Immunodetection was performed with a mouse monoclonal antibody against ceramide (clone 15b4). Quantification was done based on laser scanning micrographs from 6 predefined areas, after which quantification was done in LSM Duo software.
Figure 2:
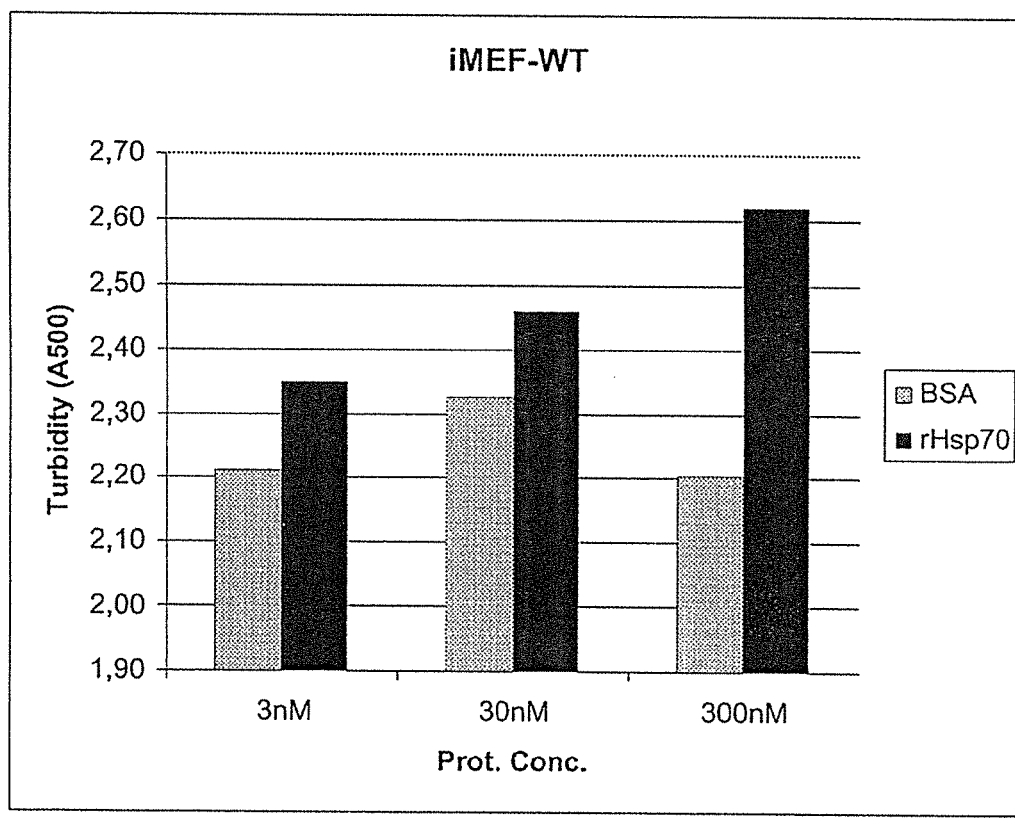
FIG. 2
The effect of rHsp70 on acid sphingomyelinase activity in iMEF-VVT (immortalized murine embryonic fibroblasts, wild type). rHsp70 was administered to cells at 3 nM, 30 nM and 300 nM, and the activity of aSMase measured (A500 is a measure of produced ceramide that increases the turbidity). Control cells were trated with BSA (bovine serum albumin).
Figure 3:
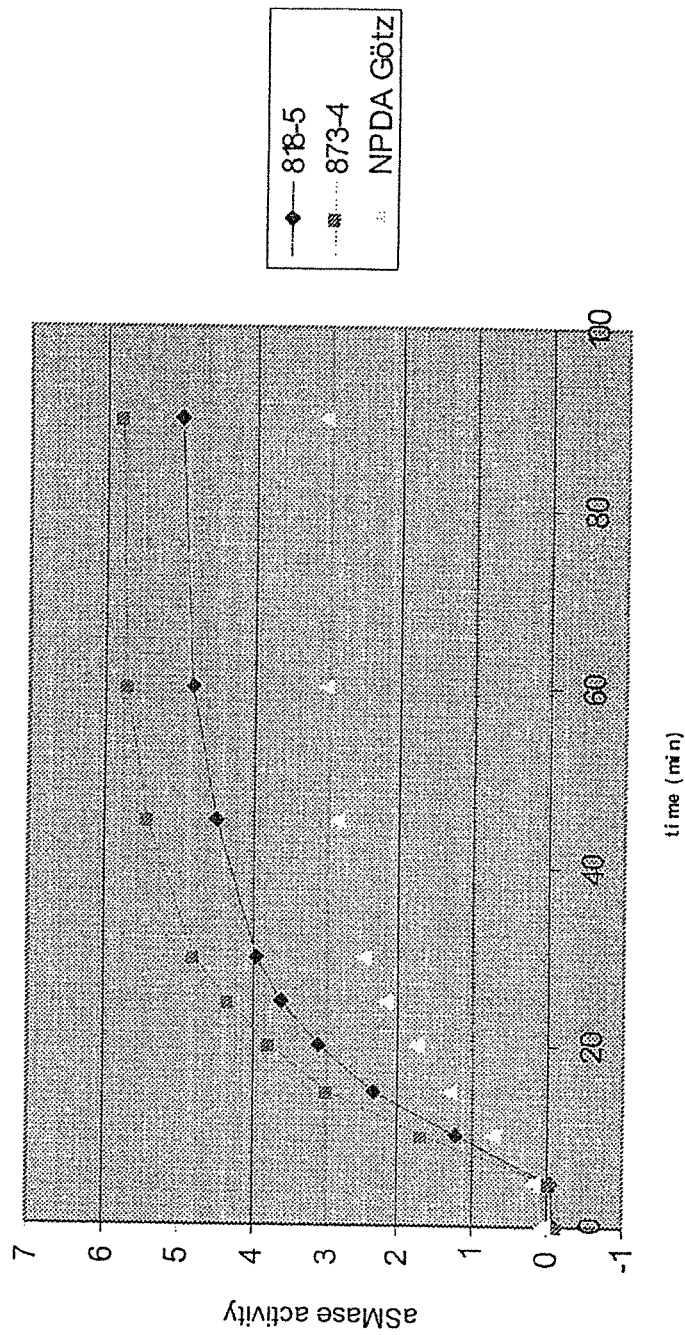
FIG. 3
Acidic SMase activity in different fibroblasts. NPDA: Niemann-Pick disease type A.

FIG. 8 rHsp70 stimulates ASM activity, stabilizes lysosomes and decreases the lysosomal volume in NPDA fibroblasts. (a) Live single-cell imaging of lysosomal stability of primary fibroblasts from a patient with NPDA analyzed as in FIG. 3e, $p<0.001$. (b) ASM activity of NPDA fibroblasts left untreated or treated with 300 nM rHsp70 for 48 h (left panel), or with 150 nM rASM alone or in combination with 300 nM rHsp70 for 24 h (right panel). The p values were calculated from the obtained enzymatic velocity (DA500/mg protein/min). The picture on the right demonstrates the endocytic uptake of rASM (green) and its localization to the lysosomal compartment as visualized by co-staining with Lysotracker Red. (c) Lysosomal stability of NPDA fibroblasts left untreated or treated for 24 h with 300 nM rHsp70, 150 nM aSMase or a combination of rHsp70 and aSMase was analyzed as in FIG. 3e. $p<0.001$ for all treatments as compared with untreated cells. (d) Quantification of lysosomal area of confocal cross sections of cells in NPDA fibroblasts left untreated or treated for 24 h with 300 nM BSA, 300 nM rHsp70, 150 nM rASM (150 nM) or a combination of rHsp70 and rASM. The picture on the right demosntrates the effect of rHsp70 (green) on the volume of the lysosomal compartment (red) in NPDA fibroblasts. White arrows indicate cells with endocytosed rHsp70 and deminshed lysosomal compartment. The values represent means±SD for 3 independent experiments. Scale bars=20 µM. UT=untreated.

FIG. 9

Colocalization of endocytosed rHsp70-AF488 with lysosomes. Representative confocal images of U-2-OS cells incubated with 300 nM rHsp70-AF488 (green) for 24 h, fixed and stained for the following organelle markers (red): lysosome-associated membrane-protein-1 (LAMP-1; lysosomes), LAMP-2 (lysosomes), LBPA/BMP (6C4; endo-lysosomal compartment), cut c (mitochondria), SERCA (ER) and golgin-97 (Golgi). Scale bars: 20 µm (LAMP-1, LAMP-2 and BMP) or 10 µm (Cyt c, SERCA and Golgin-97).

FIG. 10

Interaction of rASM (recombinant aSMase) and BMP in the presence of rHsp70. (a) interaction of rASM with immobilized anionic liposomes (average diameter is 100 nm, total lipid concentration is 0.1 mM, and composition; 10 mol % sphingomyelin, 50 mol % phosphatidylcholine, 20 mol % cholesterol and 20 mol % BMP) at pH 4.5. Response signals measured subsequent to the binding of the liposomes where defined as zero. (b) The effect of prebound rHsp70 on subsequent binding of rASM. Indicated amounts of rHsp70 were incubated with immobilized anionic liposomes identically to (a). After a 10 min dissociation phase of rHsp70, 200 nM rASM was added for 180 s followed by 10 min dissociation.

FIG. 11

Effect of the small molecule Hsp70 inducer; Benzyl Alcohol on Niemann-Pick Type A (NPDA) patient fibroblasts. (A) Induction of Hsp70 in NPDA Götz by Benzyl alcohol in a dose-dependent manner (protein expression). (B) Increased stability of NPDA Götz lysosomes after treatment of NPDA Götz cells with 40 mM Benzyl Alcohol. (C) Decreased pathology in NPDA Götz cells after treatment with 40 mM Benzyl Alcohol, as measured by lysosomal cross-sectional area (method further detailed in Example 2).

FIG. 12

Effect of aSMase depletion on lysosomal stability. Small interfering RNAs (siRNAs) targeting acid Sphingomyelinase (si938, si1257, si1340) and a control siRNA (mm) were transfected into U2OS cells using Oligofectamine (lnvitrogen) according to the manufacturers guidelines. Concentration of siRNAs: 50 nM. After 72 h hours knockdown was confirmed via RT-PCR (not shown) and cells analyzed for lysosomal stability via live single-cell imaging of acridine orange mediated photooxidation. Increase in green fluorescence was continuously measured to give full kinetic curves for the loss of lysosomal integrity. As evident form the graphs cells treated with siRNAs targeting aSMase show a marked decrease in lysosomal stability. The method is further explained in Example 2.

FIG. 13

Treatment of all NPDA/B cell lines with rHsp70 dramatically reverses the lysosomal pathology, i.e. reduces the cross-sectional area of lysosomes. Quantification of lysosomal area of confocal cross sections of cells of Niemann-Pick Disease Type A and B fibroblasts (NPDA/NPDB) and normal fibroblasts (BJ) left untreated or treated for 24 h with 300 nM BSA or Dextran as control, or treated for 24 h with 300 nM rHsp70, 150 nM rhaSMase or a combination thereof. NPDA cells treated for 24 h with 300 nM rHsp70-W90F (W90F)—the Hsp70-mutant which does not interact with BMP, has an effect comparable to control cells. See Example 2 for methods.

FIG. 14

Increased activity of aSMase in Hsp70 transgenic fibroblasts and rHsp70 treated NPDA fibroblasts. Mass spectroscopic analysis of lipid species (sphingomyelin and ceramide as indicated) in immortalized mouse embryonic fibroblasts (iMEFs), either wild type (WT) or Hsp70-transgenic (TG) (A and B), as well as Niemann-Pick Disease type A patient fibroblasts (NPDA 83/24) either left untreated or treated with rHsp70 (C). The lower levels of sphingomyelin and higher levels of ceramide indicate an increased activity of acidic sphingomyelinase.

FIG. 15

Reversion of pathology in Farber isease Patient Fibroblasts. Quantification of lysosomal area of confocal cross sections of cells from Farber Disease Patients. Farber Disease patient fibroblasts (Farber 89/73 and Farber 89/78) were left untreated or treated for 24 h with 300 nM BSA or 300 nM rHsp70 as indicated. As evident from the figures, the treatment of Farber disease patient fibroblasts with rHsp70 dramatically reverses the lysosomal pathology, i.e. reduces the cross-sectional area of lysosomes. See Example 2 for a description of methods.

FIG. 16

Hsp70 increases endocytic uptake of other molecules. Panel A: immortalized mouse embryonic fibroblasts (iMEF), either wildtype (WT) or transgenic for Hsp70 (TG) where incubated with 20 µg/mL Alexa Fluor-488-labelled BSA (BSA*) for 24 h. Endocytic uptake was verified by fluorescence microscopy (not shown) (see example 2). Cells where then harvested and analyzed for uptake of BSA*. As evident from the figure the Hsp70-transgenic iMEFs had a significantly higher uptake of BSA* than wildtype iMEFs. Panel B: U2OS osteosarcoma cells where incubated with 20 µg/mL BSA* for 24 h either with 3000 nM rHsp70 or without as indicated. Endocytic uptake was verified by fluorescence microscopy (not shown) (see example 2). Cells where then harvested and analyzed for uptake of BSA*. As evident from the figure, the U2OS cells in which BSA* and rHsp70 where added together had a significantly higher uptake of BSA* than cells incubated with BSA* alone.

DETAILED DESCRIPTION OF THE INVENTION

As is demonstrated by the present inventors, Hsp70 exerts a major part of its cytoprotective effect through a direct interaction with endo-lysosomal membranes; an interaction which is orchestrated by a specific phospholipid, namely BMP (bis(monoacylglycero)phosphate). BMP is present only in late endosomes and lysosomes. The inventors show that the Hsp70-BMP interaction is dependent on the N-terminal ATP-ase domain of Hsp70, specifically tryptophan 90, and also that the interaction is pH-dependent. The interaction between Hsp70 and BMP is essential for the membrane-stabilizing effect of Hsp70, by providing a platform for modulating the stability of a specific subset of lysosomal enzymes, and preventing destabilization of lysosomal membranes with ensuing release of lysosomal enzymes. These findings form the basis for a new and promising treatment modality for the lysosomal storage disorders, as disclosed herein.

Lysosomes

Since the discovery of lysosomes by de Duve in 1955, the view of this organelle has been dominated by the dogma that it is solely the terminus of the endocytic pathway in animal cells—a compartment housing a vast array of hydrolases, that, if released into the cytosol, cause necrosis and tissue inflammation. This view of the lysosomes as, at best, a garbage disposal unit, and at worst, an unspecific "suicide bag" has changed dramatically due to recent discoveries that provide evidence for numerous more specific tasks for lysosomes and their contents.

Lysosomal Hydrolases

As the main compartment for intracellular degradation and subsequent recycling of cellular constituents, the lysosomes receive both hetero- and autophagic cargo, which in the lumen of this organelle find their final destination. The degradation is carried out by a number of acid hydrolases (phosphatases, nucleases, glycosidases, proteases, peptidases, sulfatases, lipases, etc) capable of digesting all major cellular macromolecules. Among the best-studied lysosomal proteases is the family of cathepsin proteases. The cathepsins can be divided into three sub-groups according to their active site amino acid, i.e. cysteine (B, C, H, F, K, L, O, S, V, W and X/Z), aspartate (D and E) and serine (G) cathepsins. The cathepsins function optimally at the acidic pH of the lysosomes (pH 4-5) although they can still function at the neutral pH outside the lysosomes, albeit having decreased stability and/or altered specificity.

Until recently the function of cathepsins was thought to be limited to intralysosomal protein-turnover, and the degradation of the extracellular matrix once secreted. However, during the past few years many of the cathepsins have been accredited with more specific functions including roles in bone remodeling, antigen presentation, epidermal homeostasis, prohormone processing, protection of cytotoxic lymphocytes from self-destruction after degranulation, maintenance of the central nervous system in mice, angiogenesis, cancer cell invasion as well as programmed cell death (PCD).

Apart from the breakdown of proteins, the lysosomes and late endosomes are also responsible for the metabolism of cellular lipids, such as the glycosphingolipids, through a series of endolysosomal enzymes and co-enzymes, whose proper function depend on the lipid composition of the intra-lysosomal membranes. The importance of functional endolysosomal lipid metabolism can be easily appreciated by the fact that clinical disease is apparent in case of dysfunction at any stage of sphingolipid metabolism, giving rise to diseases such as Tay-Sachs, Sandhoff, Farber, Fabry, Gaucher, Krabbe and Niemann-Pick disease.

Trafficking to and from the Lysosomes

The traffic of endocytic membranes serves an essential role in the mammalian cell through its delivery of membrane components, various solute molecules and receptor-associated ligands to a range of intracellular compartments. Whilst the various endocytic routes until recently appeared simple, with the main pathways converging on the lysosomes, where degradation and possible recycling back to the plasma membrane would take place, recent evidence shows that these pathways are more complex than first imagined.

The Endocytic Route

Endocytosis is best understood in terms of the receptor-mediated endocytosis of molecules via the formation of clathrin-coated pits, although a variety of non-clathrin mediated endocytic routes (e.g. macropinocytosis, phagocytosis, uptake via caveolae-formation and non-clathrin-coated-pit formation) have also been identified. The nomenclature of the endocytic system has not been fully standardized, and the commonly used term "early endosome" actually describes two distinct endosomal compartments—the sorting endosome and the endocytic recycling compartment (ERC). In the conventional receptor-mediated endocytic pathway, receptors such as the transferrin receptor, the low density lipoprotein receptor and the mannose 6-phosphate receptor (MPR) concentrate into clathrin-coated pits on the surface of the plasma membrane by virtue of interactions between sequence motifs in their cytoplasmic tails and elements in the clathrin coat. After shedding of its clathrin-coat, the newly formed endosome fuses with other endosomes and pre-existing sorting endosomes to become a sorting endosome. As the name implies, its primary task is to sort newly acquired components to their correct locations. The three known destinations include the plasma membrane, the late endosomes and the ERC. As the sorting endosome matures, it experiences a drop in pH, which facilitates the release of receptor-bound ligands into the lumen of the endosome. Before the full maturation of the sorting endosome into the late endosome, however, the molecules destined to recycling must be sorted out. It is believed that this process takes place through the pinching off of narrow tubules, a process, which favors the sorting of membrane proteins from solute molecules as the surface-area-to-volume ratio of the tubules is greater than that of the vesicular sorting endosome. The pinched-off-tubules can either relay the membrane proteins directly back to the plasma membrane (the direct return pathway) or to the ERC. The ERC is mainly a collection of tubular organelles, whose localization varies between cell types. While the ERC is capable of sorting molecules to several different destinations, most of the molecules that transit via the ERC return to the plasma membrane.

As the sorting endosome matures, its luminal pH steadily drops, mainly due to the action of the vacuolar-type proton ATPase (V-ATPase), while shifts in membrane lipid and protein composition also occur. The membrane traffic from the sorting endosome to the late endosome and further into the lysosome has been the scene of some controversy. The dispute concerns whether this transport is best explained via vesicular transport or by the maturation of the sorting endosome. Both models provide for an intermediate between the sorting and the late endosome. While the maturation model argues that the vesicle, which reaches the late endosome, is what remains after the removal of components from the former sorting endosome, the pre-existing compartment model argues that transport of molecules to the late endosomes occurs via an endocytic carrier vesicle (ECV), a specific transport vesicle between pre-existing sorting and late endosomal compartments. Both the sorting and late endosomal compartments are considered to be structurally more complex and to have more specialized functions than the carrier vesicles. Recent live-cell imaging studies have reconciled mechanistic aspects of both models, however, as vesicles arising from a dynamic early endosome network can undergo a conversion in which they loose the small GTPase RAB5 and recruit RAB7, a marker of late endosomes. Although the organization of the endocytic pathway is functionally well defined, the nomenclature can be confusing. Functionally, the endocytic pathway is defined by housekeeping receptors (e.g. the transferrin receptor) and other lipids and proteins being cycled through the early endosome/sorting endosome where receptor-ligand uncoupling occurs—but not through late endosomes where proteolysis can occur. Beyond these functional criteria however, the picture becomes cloudier when it comes to nomenclature, not least so as the generation of intraluminal vesicles, starting in the early endosomes and becoming more and more prominent during the maturation to late endosomes, has given rise to the term "multivesicular bodies" (MVB). This term has been used interchangeably as another name for the ECVs and late endosomes as well as for all endocytic vesicles containing multivesicular regions or elements, including the hybrid organelle that forms when the lysosomes fuse with the late endosomes (which contain multivesicular structures). However, late endosomes contain more luminal membrane vesicles than early endosomes and are thus often the compartment described by the term "multivesicular bodies".

Finally, a substantial amount of confusion in the field has arisen from the definition, or rather lack thereof, of late endosomes versus lysosomes. Both compartments are equally acidic and most, if not all, proteins present in lysosomes are also found in late endosomes. According to the maturation model, the late endosomes would be precursors for the lysosomes, but given the gradual development, as the theory suggests, a stringent classification could be very difficult to achieve. Recently, however, evidence has been presented for lysosomes and late endosomes being separate compartments, which then undergo both "kissing" events (transient fusions) as well as complete fusion events, after which the lysosomes can reform from the hybrid organelle.

The Biosynthetic Route

Apart from endocytosis, the late endosomes also receive cargo via the MPR pathway from the trans-golgi network (TGN) (the biosynthetic route). The cation-dependent MPR and the cation-independent MPR/Insulin-like growth factor-II (IGF-II) receptor share the task of delivery of newly synthesized acid hydrolases from the TGN to the lysosomes. The recognition of acid hydrolases by MPRs requires the addition of carbohydrates in the endoplasmic reticulum and the subsequent modification and phosphorylation of the carbohydrate residues to mannose-6-phosphate moieties in the cis-Golgi The MPR-bound hydrolases are first delivered to endosomes, where they dissociate from the receptors due to the drop in the lumenal pH, hereby allowing the receptors to recycle back to the TGN. The protein mainly responsible for the sorting of the MPRs into clathrin-coated pits at the TGN, is an adaptor protein-1 (AP-1), although the Golgi-localized, γ-ear-containing ADP ribosylation factor-binding proteins (GGAs) also play a part. Whether AP-1 and the GGAs work in concert or in fact target the two MPRs to different subcellular localizations is presently unknown. AP-1 is part of an adaptor protein family consisting of four members, all of which are heterotetrameric proteins utilized extensively in the secretory and endocytic pathways. In addition to the above-mentioned role of AP-1 in clathrin-coated pits formed in TGN, AP-1 and AP-2 are used in clathrin-coated pits during endocytosis at the plasma membrane, while AP-3 and AP-4 function in the trafficking of the lysosome-associated membrane proteins (LAMPs).

The Autophagic Route

Autophagy is the third well-characterized route by which macromolecules reach the lysosome. Autophagy is an evolutionary conserved pathway involved in the turnover of long-lived proteins and organelles. It usually operates at low basal levels, although it can be induced, for example under conditions of nutrient starvation. Under these conditions macroautophagy is the major pathway responsible for delivering material to the lysosomes. Macroautophagy is characterized by a flat membrane cistern wrapping around cytoplasmic organelles and/or a portion of cytosol thereby forming a closed double-membrane bound vacuole, the autophagosome. The autophagosome finally fuses with lysosomes forming autophagolysosomes/autolysosomes, where the degradation and recycling of the engulfed macromolecules occur. The origin of the autophagosome membrane is still not clarified. The endoplasmic reticulum, Golgi, a less-well characterized membrane compartment called the phagophore as well as de novo synthesis have all been proposed as origins of the autophagosome membrane. Recent progress through yeast genetics and the subsequent discovery of mammalian homologues is rapidly enhancing the understanding of the process of autophagy and will hopefully shed light also on the origin of the autophagosomal membrane in the near future.

There are also other routes by which the lysosomes receive autophagic cargo. A rather indiscriminate process termed microautophagy is characterized by engulfment of cytosol by the lysosomes through invaginations of the lysosomal membrane. Besides the macromolecules, which are present in the engulfed cytosol, this process may also involve the uptake of organelles such as peroxisomes. Finally, chaperone-mediated transport of cytosolic proteins into the lysosomal lumen presents a more direct and selective form of autophagy. This pathway is dependent on the presence of the constitutively expressed member of the Heat shock protein 70 family, Hsc70, on both sides of the lysosomal membrane. The process is furthermore dependent on the recognition of a KDEL sequence motif in target proteins by LAMP-2a.

Reformation of Lysosomes and Lysosomal Secretion

After fusion of lysosomes with late endosomes or autophagosomes, the lysosomes are reformed from the resultant hybrid organelles through sequestration of membrane proteins and condensation of the lumenal content. Of the membrane proteins that need to be removed or recycled from the hybrid organelle, the most obvious are the MPRs, as they by definition are absent from lysosomes. The lysosomes, however, cannot be seen as the terminal point of the endocytic pathways as they are also able to form secretory lysosomes through fusion with secretory granules, a process that is $Ca^{2+}$-dependent and was first recognised in secretory cells of haematopoietic origin. However, evidence also exists for a $Ca^{2+}$-regulated membrane-proximal lysosomal compartment responsible for exocytosis in non-secretory cells. The process of exocytosis is dependent on the protein Rab27a, a member of the Rab protein family, which counts more than 60 members. The Rabs are small GTPases that have key regulatory roles in most membrane-transport steps including vesicle formation, motility, docking and fusion. At least 13 Rab proteins are utilised in the endocytic pathways in order to determine the fate of the various endocytosed molecules and their vesicles.

Programmed Cell Death

Regulation of overall cell number as well as the amount of cells constituting the different tissues along with the need for a mechanism of eliminating unwanted cells is of fundamental importance in multicellular organisms. Programmed cell death is the means to this end, endowing the multicellular organism with the potential to rid itself of unwanted cells without the leakage of cellular constituents, thus avoiding the inflammation associated with necrosis, the conceptual counterpart to programmed cell death.

Apoptosis

The word apoptosis is used in Greek to describe the "dropping off" or "falling off" of petals from flowers, or leaves from trees and was first coined by Currie and colleagues in 1972 to describe a common type of programmed cell death, which the authors had observed in a number of tissues and cell types. The authors had noticed that the events they observed had significant morphological similarities, which were distinct from the morphological features characterizing cells undergoing pathological, necrotic death and suggested that these common morphological features might be due to an identical underlying process.

When cells die by apoptosis, they undergo a series of transforming events. Amongst these events, and essential for the characteristic apoptotic phenotype, is the activation of caspases—a family of cysteine endopeptidases, which cleave substrates at specific aspartate residues, hence the name. The activation of the caspases lead to proteolytic processing of other caspases as well as a host of other changes in the overall protein activities within the cells, ultimately producing the characteristic morphological features associated with the caspase-activation and thus, per definition, apoptosis. The classical apoptotic features include cell shrinkage and blebbing of the cytoplasmic membrane, condensation of chromatin within the nucleus in clear, geometrical shapes, fragmentation of DNA into ~200 bp integers, the so-called nucleosomal ladder, cellular detachment from its neighboring cells and disintegration of the cell into small, enclosed vesicles termed apoptotic bodies. In a multicellular environment these apoptotic bodies are ultimately phagocytosed by macrophages or neighboring cells hereby completing the removal of the unwanted cell.

Programmed Cell Death

Programmed cell death (PCD) is not synonymous with apoptosis although one could be inclined to think so based on the amount of literature using these terms indiscriminately. The term PCD is gradually taking over, but the term apoptosis is still used to describe a cell death program orchestrated by the activation of caspases, in particular caspase-3. However, the ability of certain cells to survive the activation of pro-apoptotic caspases as well as PCD with complete absence of caspase activation and caspase-activation leading to non-apoptotic PCD, has revealed a remarkable plasticity of the cellular death programme(s) and PCD can thus be more accurately defined as cell death dependent on signals or activities within the dying cell. It has been suggested that PCD can be subdivided into apoptosis, apoptosis-like and necrosis-like PCD, according to the nuclear morphology of the dying cells, each definition coined to distinct morphological characteristics, the main feature being the shape of chromatin condensation or the absence hereof, although it would be preferable to make distinctions of PCD based on the signaling pathways participating under any given set of conditions leading to PCD. This way of distinguishing between different modes of PCD is not yet applicable however, as the threads leading to the varying kinds of cell death remains to be sorted out.

Necrosis

Necrosis is the conceptual counterpart to PCD, as it cannot be prevented by any other means than removing the stimulus giving rise to the necrosis. This mode of cell death is usually seen during pathological insults to an organism.

The Molecular Machinery of Programmed Cell Death

Apoptosis

As mentioned in the previous section, apoptosis is defined by the activation of members of the family of cysteine endopeptidases known as the caspases and the morphology associated with their activation. The caspases reside in cells as inactive zymogens, which can be rapidly activated by proteolytic processing. This processing proceeds in a hierarchic cascade in which an apoptotic stimulus activates an initiator caspase (e.g. caspase-8 and -9), which in turn activates the next level in the hierarchy, the effector caspases (e.g. caspase-3, -6 and -7). The latter are considered the executioners of apoptosis as they cleave a number of substrates, the processing of which ultimately leads to the phenotype associated with apoptosis. The apoptotic programme can be activated by a variety of stimuli, which can be broadly divided into extracellular and intracellular stimuli, the latter seeing the mitochondrion as an essential player. The extracellular stimuli and the following response giving rise to apoptosis are also referred to as the extrinsic signaling pathway and are comprised of a series of events starting with activation of one of a variety of death receptors such as Fas/Apo-1/CD95, TNFR or TRAIL. Upon binding of their appropriate ligand, these receptors recruit death domain (DD)-containing adaptor molecules, such as TRADD (TNFR1-associated death domain protein) and FADD (Fas-associating protein with death domain), through interaction with the DD present in the receptors. These adaptor molecules then recruit caspase-8 to the receptor complex, where the caspase is activated, possibly by proximity-induced autocatalytic processing. In certain cells (the so-called type I cells) caspase-8 then directly cleaves and activates procaspase-3, whereas in type II cells, the substratum for caspase-8 is the cytoplasmic protein Bid. The cleavage of Bid generates a fragment (truncated Bid (tBid)), which induces the oligomerisation, translocation and insertion of two pro-apoptotic Bcl-2 family members, Bax and Bak into the outer mitochondrial membrane. This insertion mediates the release of the electron-carrier cytochrome c (CytC) from the mitochondrial intermembrane space along with a host of other proteins, the most prominent of which include Apoptosis Inducing Factor (AIF), Smac/DIABLO which antagonizes the effects of the proteins known as inhibitors-of-apoptosis (IAP) proteins and endonuclease G, a DNAse. It should be noted, that although this is the pivotal point in the theories of caspase activation through mitochondria, no conclusive evidence has been presented with regard to how the insertion of Bax and Bak facilitates the release of cytochrome c. Upon release from the mitochondrion, CytC accumulates in the cytoplasm, where it binds to the protein Apaf-1 (apoptotic protease-activating factor-1) resulting in a conformational change, which promote oligomerisation of Apaf-1. This oligomer then binds procaspase-9 through homotypic interactions between caspase recruitment domains (CARDs) resulting in the formation of a complex called the apoptosome. The formation of this complex leads to a greatly enhanced enzymatic activity of pro-caspase-9, the activity of which leads to the proteolytic activation of caspase-3.

Apoptosis can also be triggered by intracellular factors eliciting mitochondrial outer membrane permeabilisation (MOMP), a process known as the intrinsic pathway. These factors include second messengers associated with cellular stress such as $Ca^{2+}$, NO and arachidonic acid as well as bilirubin, bile salts and stimuli which can give rise to protein denaturation and nuclear and mitochondrial DNA damage such as ionizing radiation, heat stress, reactive oxygen species (ROS) and chemotherapeutic agents. In the event of nuclear DNA damage, this is sensed by a variety of protein kinases, which depends on the form of DNA damage but also the noxa eliciting it. The activity of these kinases induce the accumulation of p53, which can then act as a transcription factor, giving rise to an enhanced transcription of pro-apoptotic genes such as Bax, Noxa and PUMA, all of which can induce MOMP. At the mitochondrial level, p53 induces the expression of mitochondrial enzymes that locally generate ROS as well as a mitochondrial matrix protein (p53AIP1), which overexpression triggers loss of mitochondrial membrane potential and apoptosis.

The induction of MOMP by p53 or by the action of the intrinsic stimuli described above is the point at which the intrinsic and extrinsic pathways converge, the route of the intrinsic pathway following the one already described for the extrinsic with release of cytochrome c, formation of the apoptosome and activation of caspase-3 constituting the final steps towards the demise of the unwanted cell.

The Alternatives to Apoptosis

Within the past decade, the exclusive role of caspases as the executioners of PCD has been challenged and mounting evidence suggest that there is more to life—and especially death—of a cell than can be ascribed to the caspases alone.

As newly developed caspase-specific pharmacological inhibitors as well as inactivation of caspase-pathways by factors such as energy depletion, nitrative/oxidative stress and members of the inhibitor of apoptosis protein (IAP) family did not always stop the progression towards death, they revealed, or even enhanced, a subset of underlying caspase-independent death-programs. These programs include death-receptor initiated pathways as well as pathways elicited by cancer drugs, growth-factor deprivation, staurosporine, Bax-related proteins and the depletion of Hsp70. The morphological features of these caspase-independent death programs are often reminiscent of the ones observed for classical apoptosis, and experimental support for a role for other proteases such as cathepsins, calpains and serine proteases as essential cofactors either upstream or downstream of caspases was rapidly growing. The argument is strengthened by the findings that many non-caspase proteases are able to cleave at least some of the classic caspase substrates, which might explain some of the similarities observed between the caspase-dependent and -independent death programmes.

Although one can argue the relevance of such death programmes, as they are masked by the efficacy of the caspases, evidence is gathering for an evolutionarily conserved role for lysosomal cathepsin proteases in cell death programs initiated as a response to various stimuli such as death receptors of the tumor necrosis factor receptor family, hypoxia, oxidative stress, osmotic stress, heat and anti-cancer drugs.

Lysosomal Involvement in Programmed Cell Death

While the role of lysosomes and their hydrolases in the clean-up phase of PCD, i.e. the engulfment of apoptotic cells and bodies by neighboring cells or phagocytes, is well established, it has taken a long time to recognize the importance of lysosomes and lysosomal hydrolases in the more immediate events of PCD. One of the reasons for this delay may be the fact that the methyl ketone peptide inhibitors commonly used to assess the role of caspases in PCD (e.g. zVAD-fmk, Ac-DEVD-fmk, Boc-D-fmk, etc) also inhibit other cysteine proteases, including several cysteine cathepsins. Even nine years after the recognition of this cross-reaction, protective effects with these inhibitors at concentrations capable of inhibiting non-caspase proteases are still often interpreted as a proof for caspase-mediated death pathways, and the role of other cysteine proteases in PCD thus continues to be underestimated. The discovery of lysosomal PCD may have been additionally delayed, because the lysosomal ultrastructure appears intact in apoptotic cells analysed by electron microscopy. Thus, the lysosomal rupture has until recently been considered as an all-or-nothing switch during late stages of uncontrolled necrotic cell death and tissue autolysis. However, new techniques allowing a more precise assessment of the lysosomal membrane integrity have revealed that lysosomes with normal ultrastructure may have leaked part of their enzymes, and that partial lysosomal membrane permeabilization (LMP) not only occurs early in many death paradigms, but can in fact trigger apoptosis and apoptosis-like PCD.

Lysosomal Membrane Permeabilization (LMP) and its Consequences

Studies with various compounds that directly target the integrity of the lysosomal membranes, such as $H_2O_2$, L-leucyl-L-leucine methyl ester, osmotic stress, sphingosine, the lysosomotropic antibiotics norfloxacin and ciprofloxacin and photo-oxidative lysosomal damage (photolysis), have convincingly proven that moderate lysosomal permeabilization can result in PCD. A quantitative relationship between the amount of lysosomal rupture and the mode of cell death has been suggested to explain the widely different morphological outcomes following LMP. According to this model, low stress intensities trigger a limited release of lysosomal contents to the cytoplasm followed by apoptosis or apoptosis-like cell death, while high intensity stresses lead to a generalized lysosomal rupture and rapid cellular necrosis. Accordingly, low concentrations of sphingosine, an acid ceramidase-generated metabolite of ceramide with detergent-like properties at low pH, induces partial LMP and caspase-mediated apoptosis, whereas higher concentrations result in massive LMP and caspase-independent necrotic cell death. In this model, the death triggered by partial LMP can be inhibited by pharmacological inhibitors of cysteine and aspartate cathepsins, and the increase in the cytosolic cathepsin activity precedes the activation of caspases and mitochondrial membrane potential changes suggesting a direct role for cytosolic cathepsins in the death process. Importantly, the role of LMP and cathepsins in cell death is not limited to the experimental models employing direct lysosomal disrupters. LMP also participates in the execution of cell death in response to a wide variety of classic apoptotic stimuli, such as activation of death receptors of tumour necrosis factor (TNF) receptor family, interleukin-1, p53 activation, growth factor starvation, microtubule stabilizing agents, etoposide, sigma-2 receptor activation, synthetic retinoid CD437, B cell receptor activation, staurosporine, osmotic stress, as well as small molecules identified in a screen for novel cancer drugs that induce p53 independent apoptosis.

LMP as a Trigger of the Mitochondrial Apoptosis Pathway

The cytotoxic effects of LMP often rely, at least partially, on the activation of the mitochondrial death pathway. An elegant microinjection study has demonstrated that when localized to the cytosol, a single lysosomal hydrolase, cathepsin D, is sufficient to trigger the mitochondrial outer membrane permeabilization and apoptosis in human fibroblasts at cellular doses corresponding to half of the total cellular cathepsin D activity. Cathepsin D is, however, not sufficient to trigger PCD in all cell death models involving LMP. Other well-documented mediators of LMP-triggered PCD include cysteine cathepsins B and L as well as reactive oxygen species. It should, however, be emphasized that the role of other lysosomal hydrolases, lysosome-derived second messengers and LMP-induced acidification of cytosol has not been appropriately ruled out. One of the links between cathepsins and mitochondrial membrane permeabilization may be Bid, a proapoptotic BH3-only protein of the Bcl-2 family that can be processed and activated by several cysteine cathepsins, but not by cathepsin D, at cytosolic pH. Cathepsin D has, however, been suggested to cleave and activate Bid in the acidic environment of the endolysosomal compartment following TNF receptor-1 (TNF-R1) internalization. According to this model, the endocytosis of the ligand-activated TNF-R1 results in acid sphingomyelinase-mediated generation of ceramide, which then binds to the inactive cathepsin D and activates it via autocatalytic processing. Cathepsin D may also activate Bax in a Bid-independent manner as demonstrated in staurosporine-treated T cells. Also in fibroblasts treated with ciprofloxacine, LMP triggers mitochondrial membrane permeabilization through a Bid-independent activation of Bax and Bak. In this model system the Bax activation is independent of cathepsin D, but relies instead on reactive oxygen species. It should be noted that ciprofloxacine-induced mitochondrial membrane permeabilization is not fully inhibited in cells lacking both Bax and Bak. The alternative mechanisms connecting LMP to the mitochondrial membrane permeabilization may include the direct effects of reactive oxygen species and/or lipid mediators such as arachidonic acid that can be generated in a cathepsin B-dependent manner.

Studies employing immortalized murine embryonic fibroblasts (MEFs) from mice deficient for individual cathepsins have clearly revealed that different cathepsins are engaged in the cell death execution depending on the stimulus triggering LMP. Immortalized MEFs from cathepsin B and L deficient mice, but not from cathepsin D deficient mice, are highly resistant to TNF, whereas the opposite picture emerges when the cells are treated with staurosporine. Extensive studies on TNF-induced cell death pathways have further revealed that the role of individual cathepsins in PCD depends on the cell type studied. As indicated above, TNF-induced death of immortalized MEFs depends on cysteine cathepsins, but not cathepsin D. Yet, cathepsin D depletion effectively protects HeLa cervix cancer cells against TNF- and cisplatin-induced cytotoxicity. This difference does not appear to be due to general differences between human and murine cells, because cathepsin B alone or together with other cysteine cathepsins is also crucial for the effective TNF-induced killing in human cervix (ME-180) and breast (MCF-7) cancer cell lines. The explanation for this diversity is as yet unknown, but varying expression levels of individual cathepsins and their inhibitors in different cell lines could play a role. Accordingly, the varying ability of different death stimuli to regulate the expression levels of individual cathepsins or their inhibitors could explain the difference in response to different stimuli. For example, adriamycin and etoposide are known to enhance the expression of cathepsin D via the activation of p53. Alternatively, other signaling pathways induced by various stimuli may co-operate with specific cathepsins.

Mitochondrion-Independent Death Pathways Induced by LMP

Importantly, the lethal effects of LMP and cytosolic cathepsins are not limited to the activation of the intrinsic apoptosis pathway. In small cell lung cancer cells treated with microtubule stabilizing drugs (paclitaxel, epothilone B and discodermolide), LMP occurs early in the death process and cysteine cathepsins mediate micronucleation and cell death in a caspase-independent manner. In TNF-treated human carcinoma cell lines LMP occurs downstream of mitochondrial outer membrane permeabilization. However, the inhibition of cysteine cathepsin activity or expression confers significant protection against TNF-induced cell death without significantly inhibiting the effector caspase activation. Furthermore, cathepsin B is responsible for apoptosis-like changes, such as chromatin condensation, phosphatidylserine exposure and plasma membrane blebbing, in the absence of caspase activity in TNF-treated murine WEHI-S fibrosarcoma cells. Furthermore, the depletion of heat shock protein 70 (Hsp70) in various human cancer cells as well as supraoptimal activation of T cells triggers LMP and cathepsin-mediated apoptosis-like PCD without the activation of the intrinsic apoptosis pathway. In line with these data, cathepsin B can induce nuclear apoptosis in isolated nuclei. Thus, cathepsins appear to carry both the ability to act as initiator—as well as effector proteases of programmed cell death depending on the stimulus and the cellular context. Especially their ability to mediate PCD in cancer cells, where the mitochondrial death pathway is blocked for example due to overexpression of Bcl-2, raises hopes that treatments inducing LMP may prove effective in treatment of cancers that are resistant to inducers of classis apoptosis. This idea is further supported by data showing that immortalization and transformation can sensitize cells to the lysosomal cell death.

Signaling to LMP

As described above, LMP followed by the release of lysosomal contents, especially cathepsins, to the cytosol is considered to be the key activation step of the lysosomal death pathway. However, the signaling pathways leading to LMP are still only beginning to emerge. One of the best studied mechanisms is the signaling from the tumor necrosis factor receptor 1 although the clarification of this signaling pathway to LMP has been greatly complicated by widely different responses in different target cells.

In summary, TNF can either induce caspase-dependent or -independent LMP depending on cellular context. In addition, the TNF-related ligands FasL, TRAIL and TWEAK have also all been associated with caspase-independent PCD with either apoptotic or necrotic morphology. Pharmacological and genetic studies indicate that the caspase-mediated pathway leading from TNF to LMP is dependent on caspases-8 and -9, although activation of caspase-9 differs widely between human and murine cells. The link between caspases and LMP is as yet unknown, and although TNF-induced caspase-8-mediated cleavage of Bid has been suggested to contribute to LMP, these findings could not be verified by TNF-induced LMP in Bid-deficient iMEFs. Bid has furthermore been suggested to be a target for cathepsins in lysosomal death pathways implicating Bid downstream, rather than upstream, of the LMP.

TNF also stimulates sphingomyelin breakdown to phosphorylcholine and ceramide by activating neutral sphingomyelinase (SMase) at the plasma membrane and acid or acidic SMase (aSMase) in the lysosomal compartment. Both events have been implicated in TNF-induced cell death pathways, but so far only neutral SMase has been connected to LMP through the factor associated with neutral SMase (FAN). Studies based on FAN deficient iMEFs as well as human fibroblasts expressing a dominant negative form of FAN have shown that FAN does not only mediate TNF-induced ceramide production, but also contributes to the caspase-8 processing and cell death. Since the TNF-induced LMP in murine hepatocytes depends on caspase-8, its reduced processing may explain the reduced LMP in TNF-treated hepatocytes expressing dominant negative FAN. The role of ceramide and its metabolites can, however, not be ruled out. Their role in TNF-induced death signaling is supported by the reduced TNF and Fas-induced hepatotoxicity in mice deficient for aSMase, which is activated downstream of caspase-8. Especially sphingosine that is generated from ceramide in a reaction catalyzed by the lysosomal enzyme acid ceramidase is a tempting candidate, as it, contrary to ceramide, can act as a detergent, directly destabilizing the lysosomal membrane. In addition to increasing the generation of the sphingosine precursor, ceramide, by activating SMases, TNF regulates sphingosine levels also by cathepsin B-mediated downregulation of sphingosine kinase-1, en enzyme that converts the pro-apoptotic sphingosine to an anti-apoptotic sphingosine-1-phospate. This activity of cathepsin B could result in the accumulation of sphingosine in the lysosomes and may thus, at least partially, explain the requirement of cathepsin B for an efficient LMP in TNF-treated hepatocytes.

TNF can also trigger LMP and cell death in the presence of caspase inhibitors. This pathway is independent of caspase-8, but requires the death domain-containing receptor interacting protein-1 (RIP-1) and involves the generation of reactive oxygen species. Oxidative stress can, together with intra-lysosomal iron, generate oxygen radicals through a Fenton-type chemistry and thereby may cause oxidation of lysosomal membrane lipids, resulting in the destabilization of the membrane and the release of the lysosomal content. The molecular links between RIP-1, oxidative stress and LMP are, however, still missing.

The induction of cell death by several classic apoptosis inducers (e.g. p53, etoposide and staurosporine) also involves LMP followed by cathepsin-dependent mitochondrial membrane permeabilization. However, the signaling pathways from these stimuli to LMP remain to be revealed.

Cellular Defense Mechanisms Against LMP

Given the potential fatal outcome of LMP, it is not surprising that cells have developed numerous strategies to counteract it—either by inhibiting the LMP itself or by protecting cells against the acid hydrolases leaking to the cytosol as a consequence of LMP.

Among its many other functions, phosphatidylinositol 3-kinase (PI3K) has been reported to protect lysosomes against destabilization. Inhibition of PI3K in human vascular endothelial cells induces the release of cathepsin B to the cytosol arguing for a rather direct role of PI3K in preserving lysosomal membrane integrity. Furthermore, PI3K inhibitors sensitize the cells to the TNF- and interleukin-1-induced lysosomal death pathways. Altered lysosomal functions and increased expression levels of cathepsins in cancer cells may pose a threat in form of decreased stability of lysosomes. Thus, PI3K, which is commonly activated in human cancer cells, may also contribute to lysosomal stability of tumor cells and thereby increase their cell death resistance. Whereas the role of PI3K on the stability of tumor cell lysosomes is purely speculative, recent data advocate for a role for Hsp70 in the protection of lysosomes against membrane-disruptive stimuli. This work has been mainly done in tumor cells, which also often demonstrate a localization of Hsp70 on the plasma membrane as well as in the endolysosomal compartment.

In the event of release of lysosomal proteases to the cytosol upon LMP, cytosolic protease inhibitors present a bulwark against its deleterious consequences. Whereas no endogenous inhibitors of cathepsin D are known, cysteine cathepsins can be effectively inhibited by at least three cytosolic protease inhibitors, i.e. cystatin A and B and serine protease inhibitor 2A (Spi2A) which was recently found to possess potent inhibitor activity also against several cysteine cathepsins (B, H, K, L and V) and cathepsin G. The importance of these inhibitors in preventing PCD in physiological and pathological conditions is demonstrated by cystatin B-deficient mice which display increased apoptosis of cerebellar granule cells. Moreover, the expression of Spi2A is induced upon TNF-treatment via the NF-κB pathway, and effectively inhibits TNF-induced cytosolic cathepsin B activity and cell death in MEFs. Interestingly, it has just been reported that in *C. Elegans*, the cytosolic serine protease inhibitor (serpin)-6 can protect against both the induction as well as the lethal effects from lysosomal injury caused by hypo-osmotic stress as well as a variety of other lysosomal stresses, demonstrating that protection against LMP is an evolutionarily conserved mechanism.

Lysosomal Storage Diseases

Lysosomal storage diseases (LSDs) are a group of approximately 40 rare inherited metabolic disorders that result from defects in lysosomal function. LSDs are caused by lysosomal dysfunction usually as a consequence of deficiency of a single enzyme required for the metabolism of lipids, glycoproteins or mucopolysaccharides. Although each disorder results from different gene mutations that translate into a deficiency in enzyme activity, they all share a common biochemical characteristic—all lysosomal disorders originate from an abnormal accumulation of substances inside the lysosome.

Individually, LSDs occur with incidences of less than 1:100.000, however, as a group the incidence is about 1:5000-1:10.000. Most of these disorders are autosomal recessively inherited, however a few are X-linked recessively inherited, such as Fabry disease.

The lysosomal storage diseases are generally classified by the nature of the primary stored material involved, and can be broadly broken into the following:

lipid storage disorders (or lipidoses), mainly sphingolipidoses (including Gaucher's and Niemann-Pick diseases)
gangliosidosis (including Tay-Sachs disease)
leukodystrophies
mucopolysaccharidoses (including Hunter syndrome and Hurler disease)
glycoprotein storage disorders (glycoproteinosis)
mucolipidoses Depending on the severity of the disease patients either die at a young and unpredictable age, many within a few months or years of birth, whereas others survive into early adulthood finally succumbing to the various pathologies of their particular disorder. The symptoms of LSD vary, depending on the particular disorder and can be mild to severe. They can include developmental delay, movement disorders, seizures, dementia, deafness and/or blindness. Some people with LSD have enlarged livers (hepatomegaly) and enlarged spleens (splenomegaly), pulmonary and cardiac problems, and abnormal bone growth.

The majority of patients are initially screened by an enzyme assay, which is the most efficient method to arrive at a definitive diagnosis. In some families where the disease-causing mutation(s) is known and in certain genetic isolates, mutation analysis may be performed. As there may be numerous different mutations, sequencing of the gene encoding the particular affected enzyme is sometimes necessary to confirm the diagnosis. Prenatal diagnosis may be useful when there is a known genetic risk factor.

The present invention is in one embodiment related to a method for treating lysosomal storage disorders.

Lysosomal Sphingolipid Hydrolysis

Figure 4:
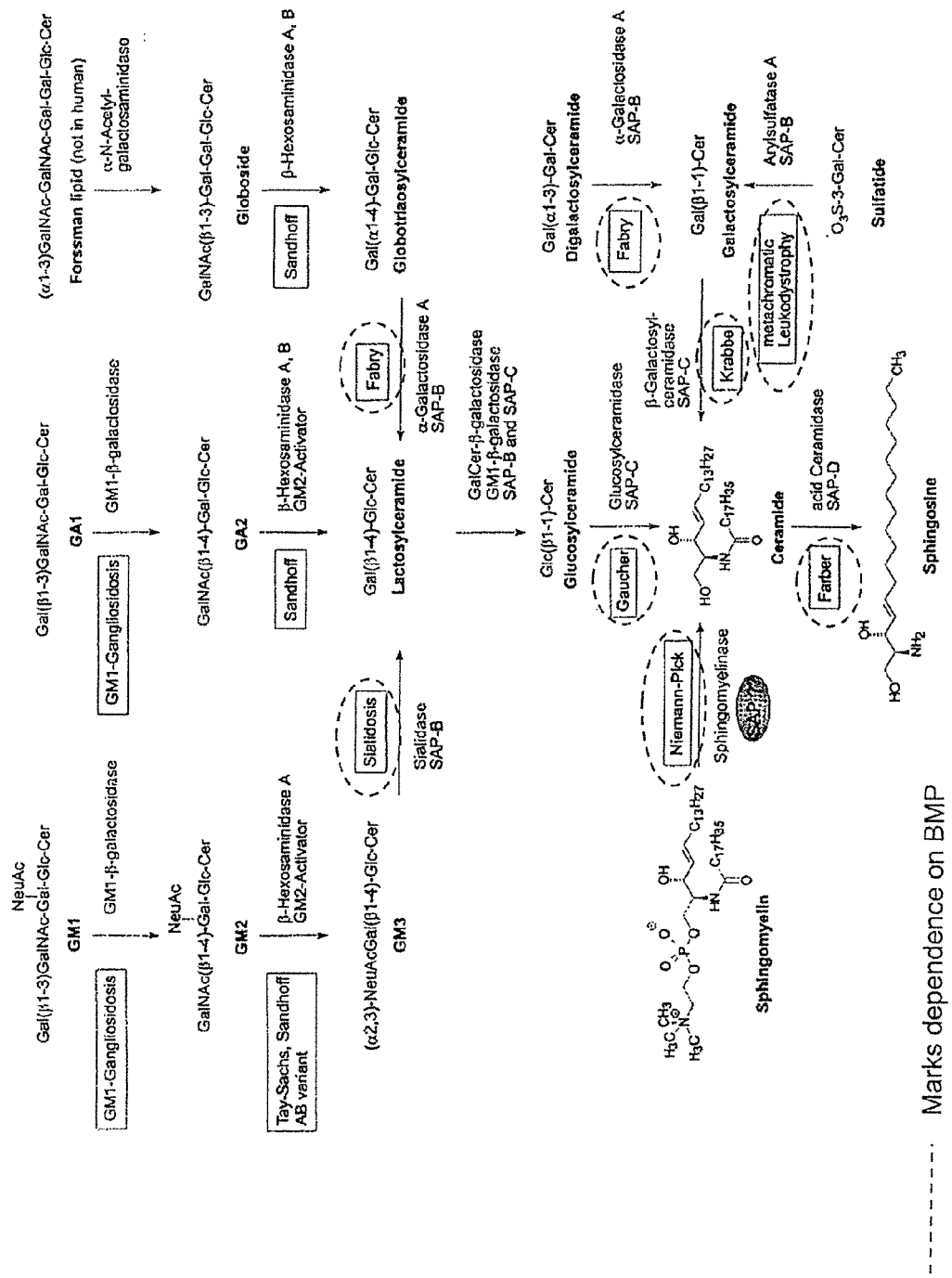
FIG. 4
Scheme of major sphingolipid hydrolysis. Exohydrolytic breakdown of sphingolipids with short hydrophilic head-groups requires non-enzymatic co-factors, sphingolipid activator proteins (SAPs or saposins). Both, inherited deficiencies of the respective enzyme as well as of the corresponding activator protein causes lysosomal lipid storage and results in the expression of various sphingolipidoses. From Ferlintz et al., Chem. Phys. Lipids, (102) 35-43, 1999.

A multitude of enzymes are involved in the lysosomal catabolism of sphingolipids (or glycophingolipids) (see FIG. 4). These enzymes, or more specifically hydrolases, are each responsible for the degradation of a specific sphingolipid.

The lysosomal sphingolipid hydrolases interacts with sphingolipid activator proteins (SAP or saposins) to stimulate the activity of said hydrolases. SAPs are considered to facilitate the enzyme/substrate interaction between water-soluble enzymes and membrane-bound substrates.

Further, the lipid composition of late endosomal and lysosomal compartments are characterized by the presence of negatively charged phospholipids such as BMP and PI (phosphatidylinositol), which also stimulates the activity of some hydrolases. The BMP-dependent lysosomal hydrolases include sialidase, α-galactosidase A, glucosylceramidase, β-galactosylceramidase, arylsulfatase A, acid ceramidase and Sphingomyelinase.

Co-Factor Saposins

Saposins are small lysosomal proteins that serve as activators of various lysosomal lipid-degrading enzymes. They probably act by isolating the lipid substrate from the membrane surroundings, thus making it more accessible to the soluble degradative enzymes. All mammalian saposins are synthesized as a single precursor molecule (prosaposin) which contains four Saposin-B domains, yielding the active saposins after proteolytic cleavage, and two Saposin-A domains that are removed in the activation reaction. The Saposin-B domains also occur in other proteins, many of them active in the lysis of membranes.

Prosaposin (PSAP) is a protein which in humans is encoded by the PSAP gene. This gene encodes a highly conserved glycoprotein which is a precursor for 4 cleavage products: saposin A, B, C, and D. Saposin is an acronym for Sphingolipid Activator Protein or SAP. Each domain of the precursor protein is approximately 80 amino acid residues long with nearly identical placement of cysteine residues and glycosylation sites. Saposins A-D localize primarily to the lysosomal compartment where they facilitate the catabolism of glycosphingolipids with short oligosaccharide groups. The precursor protein exists both as a secretory protein and as an integral membrane protein and has neurotrophic activities. Saposins A-D are required for the hydrolysis of certain shingolipids by specific lysosomal hydrolases.

The saposins are important co-activators of sialidase (SAP-B), α-galactosidase A (SAP-B), glucosylceramidase (SAP-C), β-galactosylceramidase (SAP-C), arylsulfatase A (SAP-B) and acid ceramidase (SAP-D). Acidic sphingomyelinase (aSMase) is not critically dependent on any of the known activator proteins, however the presence of saposins increases the activity of this enzyme. A fifth saposin; GM2-activator protein has also been characterised.

BMP

Bis(monoacylglycero)phosphate (BMP), also known as Lysobisphosphatidic acid, is a major part of the lipid composition of late endosomal and lysosomal compartments. It is a negatively charged phospholipid, more specifically a glycerol-phospholipid.

BMP was first isolated from rabbit lung but is now known to be a common if minor constituent of all animal tissues. Its stereochemical configuration differs from that of other animal glycero-phospholipids in that the phosphodiester moiety is linked to positions sn-1 and sn-1' of glycerol, rather than to position sn-3. It remains unclear whether positions sn-3 and 3' or sn-2 and sn-2' in the glycerol moieties are esterified with fatty acids. Whatever the positions of the fatty acids on the glycerol molecule, their compositions can be distinctive with 18:1(n-9) and 18:2(n-6), 20:4 and 22:6(n-3) being abundant, although this is highly dependent on the specific tissue, cell type or organelle. Such distinctive compositions suggest quite specific functions, some of which have yet to be revealed.

BMP is usually a rather minor component of animal tissues. However, it is highly enriched in the lysosomes of liver and other tissues, where it can amount to 15% or more of the membrane phospholipids, and it is now recognized as a marker for this organelle. It is the late endosomes and the lysosomes that contain the unique lipid, BMP. Indeed, there appear to be internal membranes of the late endosomes that contain as much as 70% of the phospholipids as BMP.

If the reported presence of BMP in some alkalophilic strains of *Bacillus* species can be confirmed, this will be the only known exception to the rule that this lipid is strictly of mammalian origin and not present in prokaryotes, yeasts and higher plants.

There is good evidence that BMP is synthesised from phosphatidylglycerol, primarily in the endosomal system. In what is believed to be the primary route, a phospholipase A2 removes the fatty acid from position sn-2 of phosphatidylglycerol in the first step. In the second step, the lysophosphatidylglycerol is acylated on the sn-2' position of the head group glycerol moiety to yield sn-3:sn-1' lysobisphosphatidic acid, by means of a transacylase reaction with lysophosphatidylglycerol as both the acyl donor and acyl acceptor. The third step has still to be adequately described but must involve removal of the fatty acid from position sn-1 of the primary glycerol unit and a rearrangement of the phosphoryl ester from the sn-3 to the sn-1 position. Finally position sn-2 of the primary glycerol unit is esterified, probably by a transacylation reaction with another phospholipid as donor (hence the distinctive fatty acid compositions). Other biosynthetic routes may be possible.

The function of BMP in lysosomes is under active investigation. It may have a structural role in developing the complex intraluminal membrane system, aided by a tendency not to form a bilayer. It is a cone-shaped molecule, and it encourages fusion of membranes at the pH in the endosomes. Further, its unique stereochemistry means that it is resistant to phospholipases, so it will hinder or prevent self digestion of the lysosomal membranes. The fatty acid constituents may turn over rapidly by transacylation, but the glycerophosphate backbone is stable. A further possibility is that this lipid may associate with specific proteins in membrane domains, functionally similar to rafts. It has been suggested that that the characteristic network of BMP-rich membranes contained within multivesicular late endosomes regulates cholesterol transport by acting as a collection and re-distribution point. For example, when lysosomal membranes are incubated with antibodies to BMP, cholesterol tends to accumulate. The process is under the control of Alix/AIP1, which is a protein that interacts specifically with BMP and is involved in sorting into multivesicular endosomes.

BMP is known to greatly stimulate the enzymes involved in the degradation of glycosylceramides, such as the sphingolipid activator proteins like the saposins. In this instance, it may simply function to provide a suitable environment for the interaction of the glycosphingolipid hydrolases and their activator. In addition, it has a dynamic role in the provision of arachidonate for eicosanoid production in alveolar macrophages.

For BMP-dependent enzymes, the rate of hydrolysis is increased dramatically when BMP is present in the membrane, for aSMase even without the presence of an activator protein such as saposin. In FIG. 4, a stippled circle marks the enzymes, or the disease in which this enzyme is defect, which show a dependence on BMP.

BMP is involved in the pathology of lysosomal storage diseases such as Niemann-Pick C disease (cholesterol accumulation) and certain drug-induced lipidoses. In these circumstances, its composition tends to change to favour molecular species that contain less of the polyunsaturated components. It is an antigen recognized by autoimmune sera from patients with a rare and poorly understood disease known as antiphospholipid syndrome, so it is probably a factor in the pathological basis of this illness.

The present invention is in one embodiment related to a method for treating lysosomal storage disorders, by exploiting the interaction between Hsp70 and BMP.

The Lipid Storage Disorders

Lipid storage disorders (or lipidoses) are a subgroup of the lysosomal storage disorders in which harmful amounts of lipids accumulate in the intracellular space due to reduced expression or function of the enzymes needed to metabolize lipids. Over time, this excessive storage of lipids can cause permanent cellular and tissue damage, particularly in the brain, peripheral nervous system, liver, spleen and bone marrow.

Lipids are a broad group of naturally-occurring molecules which includes fats, waxes, sterols, fat-soluble vitamins (such as vitamins A, D, E and K), monoglycerides, diglycerides, phospholipids, and others. The main biological functions of lipids include energy storage, as structural components of cell membranes, and as important signaling molecules.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits: ketoacyl and isoprene groups. Using this approach, lipids may be divided into eight categories: fatty acyls, glycerolipids, glycerophospholipids, sphingolipids, saccharolipids and polyketides (derived from condensation of ketoacyl subunits); and sterol lipids and prenol lipids (derived from condensation of isoprene subunits).

Although the term lipid is sometimes used as a synonym for fats, fats are a subgroup of lipids called triglycerides. Lipids also encompass molecules such as fatty acids and their derivatives (including tri-, di-, and monoglycerides and phospholipids), as well as other sterol-containing metabolites such as cholesterol.

Several lysosomal storage disorders characterized by the accumulation of lipids (i.e., lipid storage disorders) have been characterized; these are outlined herein below.

The present invention is in one embodiment related to a method for treating lipid storage disorders.

Niemann-Pick Disease

Niemann-Pick disease (NPD) is caused by a defect in the acidic sphingomyelinase enzyme (aSMase), with the systematic name sphingomyelin phosphodiesterase. The bulk of membrane sphingomyelin is hydrolysed by the lysosomal enzyme aSMase to produce ceramide (and phosphocholine). Sphingomyelin consists of a ceramide membrane anchor which is linked to a short hydrophilic phosphorylcholine moiety.

Sphingomyelinase is not critically dependent on any of the known activator proteins, making the assumed intramolecular activator domain of aSMase and the presence of negatively charged lipids in the lysosomes sufficient for sphingomyelin turnover. aSMase thus does not require the presence of saposins as a co-factor; however the presence of saposins invariably further stimulates the activity of this enzyme. (Ferlinz et al., 1999). aSMase activity is stimulated by BMP.

When sphingomyelin cannot be metabolized properly it is accumulated within the cell, eventually causing cell death and the malfunction of major organ systems. Symptoms may include lack of muscle coordination, brain degeneration, learning problems, loss of muscle tone, increased sensitivity to touch, spasticity, feeding and swallowing difficulties, slurred speech, and an enlarged liver and spleen. There may be clouding of the cornea and a characteristic cherry-red halo develops around the center of the retina.

Niemann-Pick disease (NPD) has 4 related types; types A, B, C and D. All types of NPD are inherited in an autosomal recessive pattern and can affect both males and females. In types A and B, insufficient activity of the enzyme aSMase causes the build up of toxic amounts of sphingomyelin. The disease occurs when both copies of a person's aSMase gene (both alleles) have a mutation.

Niemann-Pick Type A (NPDA), the most common type, occurs in infants. It is characterized by jaundice, an enlarged liver, and profound brain damage. There is currently no effective treatment for persons with type A, and patients with type A die in infancy, usually before the age of 18 months.

Niemann-Pick Type B (NPDB) involves an enlarged liver and spleen, which usually occurs in the pre-teen years, and respiratory problems are common. The enlargement of organs and the respiratory problems can cause cardiovascular stress and can lead to heart disease later in life. Patients with NPDB generally have little or no neurologic involvement. Bone marrow transplantation has been attempted in a few patients with type B, and mixed results have been reported. The future development of enzyme replacement and gene therapies might also be helpful for those with type B. Children with Type B may live a comparatively long time, but may require supplemental oxygen because of lung impairment.

NPDA and NPDB are both caused by the same enzymatic deficiency and there is growing evidence that the two forms represent opposite ends of a continuum. People with NPDA generally have little or no aSMase production (less than 1% of normal) while those with NPDB have approximately 10% of the normal level of aSMase.

There are approximately 1,200 cases of NPA and NPB world wide with the majority being Type B or an intermediate form.

NPDA and NPDB are diagnosed by measuring the level of activity of aSMase in white blood cells from a blood sample. While this test will identify persons with Type and B, it is not very reliable for detecting persons who are carriers (who have only one non-functional copy of the ASM gene). Further, the test will show decreased activity of aSMase, but it cannot always predict whether the individual will have type A or Type B or an intermediate variant of the disease; that requires clinical evaluation of the individual.

In certain populations, specific mutations account for a high percentage of cases of aSMase deficiency. For NPDA, the mutations R496L, fsP330 and L302P account for over 95% of disease-causing genetic changes in the Ashkenazi Jewish population. Direct testing of individuals in this population for these 3 changes is used for carrier identification. In other populations, the mutations must first be identified in the affected individual before DNA carrier testing can be performed for family members.

For NPDB, the H421Y and K576N aSMase mutations account for 85% of the Saudi Arabian NPDB population; the L137P, fsP189 and L549P mutations account for 75% of the Turkish NPDB population; the S379P, R441X and R474W mutations account for 55% of the Portuguese NPDB population; the A196P mutations account for 42% of the English/Scottish NPDB population, and the mutations F480L and DeltaR608 have also been identified as disease-causing in NPDB patients.

Niemann-Pick Type C (NPDC) is very different than Type A or B. NPDC Patients are not able to metabolize cholesterol and other lipids properly within the cell, and is characterized by a defect that disrupts the transport of cholesterol between brain cells. Consequently, excessive amounts of cholesterol and other lipids accumulate within the liver, spleen and brain. NPDC causes a secondary reduction of aSMase activity, which led all three types to be considered forms of the same disease.

There is considerable variation in when Type C symptoms first appear and in the progression of the disease. Symptoms may appear as early as a few months of age or as late as adulthood. Vertical gaze palsy (the inability to move the eyes up and down), enlarged liver, enlarged spleen, or jaundice in young children are strong indications that NPC should be considered. It is common for only one or two symptoms to appear in the early stages of the disease. In most cases, neurological symptoms begin appearing between the ages of 4 and 10. Generally, the later neurological symptoms begin, the slower the progression of the disease.

Type C Niemann-Pick disease has about 500 cases diagnosed worldwide. It is believed, however, that the number of people affected by NPDC is higher, but diagnostic difficulties do not allow an accurate assessment of the occurrence rate. NPDC has been initially diagnosed as a learning disability, mild retardation, clumsiness, and delayed development of fine motor skills.

Niemann-Pick Type D is now considered a variant of type C. Type D usually occurs in people with an ancestral background in Nova Scotia. Individuals with types C and D are frequently placed on a low-cholesterol diet, but its clinical benefit is not convincing. The life expectancy of persons with types C and D varies, however the disease is always fatal. The vast majority of children die before age 20.

NPDC is a rare and extremely variable condition and therefore may not be recognized by some health care providers. For those specialists who do suspect this diagnosis in a patient, it can be determined by taking a skin biopsy, culturing the fibroblasts, and studying their ability to transport and store cholesterol. The transport of cholesterol in the cells is studied by measuring conversion of the cholesterol from one form to another (esterification). The storage of cholesterol is assessed by staining the cells with a chemical (filipin) that glows under ultraviolet light.

In 1997, the NPC1 gene was identified. Mutations, or disease-causing changes, in this gene are responsible for about 95% of all NPDC cases. Since then, over 250 different genetic mutations related to NPDC have been identified in this gene and in the second NPDC gene, called NPC2. Overall, in about 95% of cases, it is possible to identify the genetic changes that have caused the disease if the diagnosis of NPC has first been confirmed by the testing outlined above. However, because there are so many unique mutations in these genes, and there are patients with classic NPC in whom mutations have not been identified, it is not optimal to use genetic testing as a general diagnostic tool for NPDC.

Niemann-Pick Disease affects all segments of the population with cases reported from North America, South America, Europe, Africa, Asia, and Australia. However a higher incidence has been found in certain populations:
  Ashkenazi Jewish population (NPDA and NPDB)
  French Canadian population of Nova Scotia (type D—now considered a variant of NPDC)
  Maghreb region (Tunisia, Morocco, and Algeria) of North Africa (NPDB)
  Spanish-American population of southern New Mexico and Colorado (NPDC)

The present invention is in one embodiment related to a method for treating Niemann-Pick disease, by modulation of acidic sphingomyelinase enzyme (aSMase) activity.

Farber Disease

Farber disease is caused by a defect in the acid ceramidase enzyme. Acid ceramidase is responsible for the conversion of ceramide to sphingosine (and fatty acid); the defect thus leads to an accumulation of ceramide. Its activity is stimulated by BMP and is dependent on saposins.

Acid ceramidase is also known as N-acylsphingosine amidohydrolase, and is coded by the gene ASAH1. It is a heterodimeric protein consisting of a nonglycosylated alpha subunit and a glycosylated beta subunit that is cleaved to the mature enzyme posttranslationally.

Farber disease is also known as Farber's lipogranulomatosis, ceramidase deficiency, Fibrocytic dysmucopolysaccharidosis, and Lipogranulomatosis. It is an extremely rare autosomal recessive disease characterized by abnormalities in the joints, liver, throat, tissues and central nervous system. The liver, heart, and kidneys may also be affected. Symptoms are typically seen in the first few weeks of life and include impaired motor and mental ability and difficulty with swallowing. Other symptoms may include arthritis, swollen lymph nodes and joints, hoarseness, nodules under the skin (and sometimes in the lungs and other parts of the body), chronic shortening of muscles or tendons around joints, and vomiting. Affected persons may require the insertion of a breathing tube. In severe cases, the liver and spleen are enlarged.

Currently there is no specific treatment for Farber disease. Corticosteroids can help relieve pain. Nodes can be treated with bone marrow transplants, in certain instances, or may be surgically reduced or removed. Most children with the classic form of Farber's disease die by age 2, usually from lung disease. Individuals having a milder form of the disease may live into their teenage years.

The present invention is in one embodiment related to a method for treating Farber disease, by modulation of acid ceramidase enzyme activity.

Krabbe Disease

Krabbe disease is caused by a defect in the β-galactosylceramidase enzyme. β-galactosylceramidase is responsible for the conversion of galactosylceramide to ceramide; the defect thus leads to an accumulation of galactosylceramide. Its activity is stimulated by BMP and is dependent on saposins.

Krabbe disease is also known as globoid cell leukodystrophy or galactosylceramide lipidosis. It is a rare, often fatal degenerative autosomal recessive disorder that affects the myelin sheath of the nervous system. It occurs in about 1 in 100,000 births. A higher prevalence, about 1 in 6,000 has been reported in some Arab communities in Israel.

Krabbe disease is caused by mutations in the GALC gene, which causes a deficiency of the galactosylceramidase enzyme. The lipid buildup affects the growth of the nerve's protective myelin sheath (the covering that insulates many nerves) and causes severe degeneration of motor skills.

Infants with Krabbe disease are normal at birth. Symptoms begin between the ages of 3 and 6 months with irritability, fevers, limb stiffness, seizures, feeding difficulties, vomiting, and slowing of mental and motor development. In the first stages of the disease, doctors often mistake the symptoms for those of cerebral palsy. Other symptoms include muscle weakness, spasticity, deafness, optic atrophy and blindness, paralysis, and difficulty when swallowing. Prolonged weight loss may also occur. There are also juvenile- and adult-onset cases of Krabbe disease, which have similar symptoms but slower progression. In infants, the disease is generally fatal before age 2. Patients with late-onset Krabbe disease tend to have a slower progression of the disease and live significantly longer.

Although there is no cure for Krabbe disease, bone marrow transplantation has been shown to benefit cases early in the course of the disease. Generally, treatment for the disorder is symptomatic and supportive. Physical therapy may help maintain or increase muscle tone and circulation. A recent study reports that cord blood transplants have been successful in stopping the disease as long as they are given before overt symptoms appear.

The present invention is in one embodiment related to a method for treating Krabbe disease, by modulation of β-galactosylceramidase enzyme activity.

Fabry Disease

Fabry disease is caused by a defect in the α-galactosidase A enzyme. α-galactosidase A is responsible for the conversion of globotriaosylceramide to lactosylceramide; the defect thus leads to an accumulation of globotriaosylceramide (also abbreviated as Gb3, GL-3, or ceramide trihexoside). Its activity is stimulated by BMP and is dependent on saposins.

Fabry disease is also known as Anderson-Fabry disease, Angiokeratoma corporis diffusum, Ruiter-Pompen-Wyers syndrome, Ceramide trihexosidosis, and Sweeley-Klionsky disease. It is an X-linked recessive (inherited) disease that affects hemizygous males, as well as both heterozygous and homozygous females; males tend to experience the most severe clinical symptoms, while females vary from virtually no symptoms to those as serious as males. This variability is thought to be due to X-inactivation patterns during embryonic development of the female.

Symptoms include anhidrosis (lack of sweating), fatigue, angiokeratomas (benign cutaneous injury of capillaries), burning extremity pain and ocular involvement. Angiokeratomas are tiny, painless papules that appear at any region of the body, but are predominant on the thighs, buttocks, lower abdomen, and groin. Cosmetic ocular involvement may be present showing cornea verticillata (also known as vortex keratopathy). Keratopathy may be the presenting feature in asymptomatic carriers, and must be differentiated from other causes of vortex keratopathy (e.g. drug deposition in the cornea). Other ocular findings that can be seen include conjunctival aneurysms, posterior spoke-like cataracts, papilloedema, macular edema, optic atrophy and retinal vascular dilation. Kidney complications are a common and serious effect of the disease; renal insufficiency and renal failure may worsen throughout life. Proteinuria is often the first sign of kidney involvement. Cardiac complications may also occur; heart related effects worsen with age and may lead to increased risk of heart disease. Cerebrovascular effects lead to an increased risk of stroke. Other symptoms include tinnitus, vertigo, nausea, and diarrhea.

Symptoms are typically first experienced in early childhood and can be very difficult to understand; the rarity of Fabry disease to many clinicians sometimes leads to misdiagnoses or ignorance. Manifestations of the disease usually increase in number and severity as an individual age.

Until recently, treatment of Fabry disease targeted the symptomatic effects. However, it is currently being treated at the cellular level through enzyme replacement therapy (ERT) using Agalsidase alpha (Replagal) and Agalsidase beta (Fabrazyme). The cost of these drugs is problematic (approximately $250,000 US a year/patient) and remains a barrier to many patients in some countries. Enzyme replacement therapy (typically infused every two weeks) may be performed in the patient's home by the patients themselves. Enzyme replacement therapy is not a cure, and it must be infused recurrently for maximum benefit.

The present invention is in one embodiment related to a method for treating Fabry disease, by modulation of α-galactosidase A enzyme activity.

Gaucher Disease

Gaucher disease is caused by a defect in the glucosylceramidase enzyme (also known as glucocerebrosidase and acid β-glucosidase); a 55.6 KD, 497 amino acids long protein. Glucosylceramidase is responsible for the conversion of glycosylceramide (or glucocerebroside) to ceramide; the defect thus leads to an accumulation of glycosylceramide. Its activity is stimulated by BMP and is dependent on saposins.

Gaucher's disease is the most common of the lysosomal storage diseases. Fatty material can collect in the spleen, liver, kidneys, lungs, brain and bone marrow. Symptoms may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the sclera. Persons affected most seriously may also be more susceptible to infection.

The disease shows autosomal recessive inheritance and therefore affects both males and females. Different mutations of glucosylceramidase determine the remaining activity of the enzyme, and, to a large extent, the phenotype. Research suggests that heterozygotes for particular glucosylceramidase mutations are at an increased risk of Parkinson's disease and particular malignancies (non-Hodgkin lymphoma, melanoma and pancreatic cancer).

Glycosylceramide is a cell membrane constituent of red and white blood cells. The macrophages that clear these cells are unable to eliminate the waste product, which accumulates in fibrils, and turn into Gaucher cells, which appear on light microscopy to resemble crumpled-up paper.

Gaucher's disease has three common clinical subtypes. Each type has been linked to particular mutations. In all, there are about 80 known mutations.

Type I (or nonneuropathic type) is the most common form of the disease, occurring in approximately 1 in 50,000 live births. It occurs most often among persons of Ashkenazi Jewish heritage, 100 times the occurrence in the general populace. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leukopenia. The brain is not affected, but there may be lung and, rarely, kidney impairment. Patients in this group usually bruise easily (due to low levels of platelets) and experience fatigue due to low numbers of red blood cells. Depending on disease onset and severity, type 1 patients may live well into adulthood. Many patients have a mild form of the disease or may not show any symptoms.

Type II (or acute infantile neuropathic Gaucher's disease) typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

Type III (the chronic neuropathic form) can begin at any time in childhood or even in adulthood, and occurs in approximately 1 in 100,000 live births. It is characterized by slowly progressive but milder neurologic symptoms compared to the acute or type 2 version. Major symptoms include an enlarged spleen and/or liver, seizures, poor coordination, skeletal irregularities, eye movement disorders, blood disorders including anemia and respiratory problems. Patients often live into their early teen years and adulthood.

The National Gaucher Foundation states that around 1 in 100 people in the general U.S. population is a carrier for type 1 Gaucher's disease, giving a prevalence of 1 in 40,000; among Ashkenazi Jews the rate of carriers is considerably higher, at roughly 1 in 15. Type 2 Gaucher's disease shows no particular preference for any ethnic group. Type 3 Gaucher's disease is especially common in the population of the Northern Swedish region of Norrbotten where the incidence of the disease is 1 in 50,000.

For type 1 and most type 3 patients, enzyme replacement treatment with intravenous recombinant glucosylceramidase can decrease liver and spleen size, reduce skeletal abnormalities, and reverse other manifestations. The rarity of the disease means that dose-finding studies have been difficult to conduct, so there remains controversy over the optimal dose and dosing frequency. Due to the low incidence, this has become an orphan drug in many countries. The currently existing treatment of Gaucher's disease, Cerezyme® (imiglucerase for injection), costs up to $550,000 annually for a single patient and the treatment should be continued for life. Miglustat is another drug approved for this disease in 2003.

Successful bone marrow transplantation cures the non-neurological manifestations of the disease, because it introduces a monocyte population with active glucosylceramidase. However, this procedure carries significant risk and is rarely performed in Gaucher patients. Surgery to remove the spleen (splenectomy) may be required on rare occasions if the patient is anemic or when the enlarged organ affects the patient's comfort. Blood transfusion may benefit some anemic patients. Other patients may require joint replacement surgery to improve mobility and quality of life. Other treatment options include antibiotics for infections, antiepileptics for seizures, bisphosphonates for bone lesions, and liver transplants.

Substrate reduction therapy may prove to be effective in stopping Type 2, as it can cross through the blood barrier into the brain. There is currently no effective treatment for the severe brain damage that may occur in patients with types 2 and 3 Gaucher disease.

The present invention is in one embodiment related to a method for treating Gaucher disease, by modulation of glucosylceramidase enzyme activity.

Sialidosis

Sialidosis, or Mucolipidosis type I (ML I), is caused by a defect in the sialidase enzyme (or alpha-neuraminidase). Sialidase is responsible for the conversion of GM3 to lactosylceramide; the defect thus leads to an accumulation of GM3. Its activity is stimulated by BMP and is dependent on saposins.

Sialidosis is inherited in an autosomal recessive manner. Symptoms are either present at birth or develop within the first year of life. In many affected infants, excessive swelling throughout the body is noted at birth. These infants are often born with coarse facial features, such as a flat nasal bridge, puffy eyelids, enlargement of the gums, and excessive tongue size (macroglossia). Many infants with are also born with skeletal malformations such as hip dislocation. Infants often develop sudden involuntary muscle contractions (called myoclonus) and have red spots in their eyes (cherry red macules). They are often unable to coordinate voluntary movement (called ataxia). Tremors, impaired vision, and seizures also occur. Tests reveal abnormal enlargement of the liver (heptomegaly) and spleen (splenomegaly) and extreme abdominal swelling. Infants generally lack muscle tone (hypotonia) and have mental retardation that is either initially or progressively severe. Many patients suffer from failure to thrive and from recurrent respiratory infections. Most infants with ML I die before the age of 1 year.

Sialidosis may be sub-categorised according to the age at which symptoms begin and the types of symptoms present. The effects of the disease may range from mild to severe.

Sialidosis is a rare disorder that has no racial predilection. Very little population data are available, but a study from the Netherlands reported a frequency of approximately 1 case in 2,175,000 live births. However, this rate may not apply to all populations, some of which could have a higher incidence; moreover, missed clinical recognition is an important factor when newborn screening is not an option.

Treatment options for sialidosis remain limited and are primarily directed at supportive care and symptomatic relief.

The present invention is in one embodiment related to a method for treating Sialidosis, by modulation of sialidase activity.

Metachromatic Leukodystrophy

Metachromatic leukodystrophy (MLD) or Arylsulfatase A deficiency is caused by a defect in the arylsulfatase A enzyme (or cerebroside-sulfatase). Arylsulfatase A is responsible for the conversion of sulfatide (or cerebroside 3-sulfate) to galactosylceramide; the defect thus leads to an accumulation of sulfatide. Its activity is stimulated by BMP and is dependent on saposins.

It is a lysosomal storage disease which is commonly listed in the family of leukodystrophies. Leukodystrophiea affect the growth and/or development of myelin, the fatty covering which acts as an insulator around nerve fibers throughout the central and peripherial nervous systems.

Like many other genetic disorders that affect lipid metabolism, there are several forms of MLD, which are late infantile, juvenile, and adult:

In the late infantile form, which is the most common form MLD, affected children begin having difficulty walking after the first year of life. Symptoms include muscle wasting and weakness, muscle rigidity, developmental delays, progressive loss of vision leading to blindness, convulsions, impaired swallowing, paralysis, and dementia. Children may become comatose. Untreated, most children with this form of MLD die by age 5, often much sooner.

Children with the juvenile form of MLD (onset between 3-10 years of age) usually begin with impaired school performance, mental deterioration, and dementia and then develop symptoms similar to the late infantile form but with slower progression. Age of death is variable, but normally within 10 to 15 years of symptom onset.

The adult form commonly begins after age 16 as a psychiatric disorder or progressive dementia. Adult-onset MLD progresses more slowly than the late infantile and juvenile forms, with a protracted course of a decade or more.

In rare cases the body can compensate for the deficiency and the person will exhibit no symptoms.

There is no cure for MLD, and no standard treatment, it is a terminal illness. Children with advanced juvenile or adult onset, and late infantile patients displaying symptoms have treatment limited to pain and symptom management. Presymptomatic late infantile MLD patients, as well as those with juvenile or adult MLD that are either presymptomatic or displaying mild to moderate symptoms, have the option of bone marrow transplantation (including stem cell transplantation), which is under investigation.

The present invention is in one embodiment related to a method for treating Metachromatic leukodystrophy, by modulation of arylsulfatase A enzyme activity.

Saposin-Deficiency

In both humans and mice, prosaposin/saposin deficiencies lead to severe neurological deficits.

Human patients with point mutations in the saposin A, B and C show phenotypes of Krabbe disease, metachromatic leukodystrophy and Gaucher disease, indicating that their primary in vivo substrates are galactosylceramide, sulfatide and glucosylceramide, respectively.

Krabbe disease, atypical, due to saposin A deficiency: An inherited biochemical disorder which results in neurological regression within a few months of birth. Death usually occurs during the first few years of life. The disorder is similar to Krabbe disease but is differentiated by the genetic origin of the biochemical defect. Krabbe disease involves a defect in the galactocerebrosidase gene whereas atypical Krabbe disease involves a defect in the prosaposin gene which causes a deficiency of saposin A.

Saposin B, previously known as SAP-1 and sulfatide activator, stimulates the hydrolysis of a wide variety of substrates including cerebroside sulfate, GM1 ganglioside, and globotriaosylceramide by arylsulfatase A, acid beta-galactosidase, and alpha-galactosidase, respectively. Human saposin B deficiency, transmitted as an autosomal recessive trait, results in tissue accumulation of cerebroside sulfate and a clinical picture resembling metachromatic leukodystrophy (activator-deficient metachromatic leukodystrophy) although with normal arylsulfatase activity. Saposin B deficiency is a heterogeneous disease with a spectrum similar to that in metachromatic leukodystrophy.

Saposin (SAP-) C is required for glucosylceramide degradation, and its deficiency results in a variant form of Gaucher disease; non-neuronopathic Gaucher disease due to SAP-C deficiency. Very high levels of chitotriosidase activity, chemokine CCL18, and increased concentration of glucosylceramide in plasma and normal (3-glucosidase activity in skin fibroblasts are observed in the patients. A missense mutation, p.L349P, located in the SAP-C domain and another mutation, p.M1L, located in the initiation codon of the prosaposin precursor protein has been identified.

In a few non-neuronopathic Gaucher patients, a mutation in both Saposin C and saposin D has been identified.

Combined saposin C and D deficiencies in mice lead to a neuronopathic phenotype with glucosylceramide and alpha-hydroxy ceramide accumulation.

In mice, saposin D deficiency is associated with ceramide accumulation, partial loss of Purkinje cells and impaired urinary system function. This phenotype does not mimic the embryonic lethality exhibited by mice with complete deficiency of acid ceramidase, saposin D's cognate enzyme Two mutations are known in humans that result in complete inactivation of all four saposins and prosaposin. Total saposin deficiency is a devastating disease with involvement of multiple organs and multiple sphingolipids. Combined saposin deficiency (or prosaposin deficiency) has been reported in a case presenting with a severe neurovisceral dystrophy which caused death as a neonate. Multiple sphingolipids were elevated in the urine, with globotriaosylceramide showing the greatest increase. A novel mutation in the PSAP gene was identified, being homozygous for a splice-acceptor site mutation two bases upstream of exon 10. This mutation led to a premature stop codon and yielded low levels of transcript.

The present invention is in one embodiment related to a method for treating saposin-deficiency. Said saposin-deficiency may be selected from the group consisting of saposin A deficiency, saposin B deficiency, saposin C deficiency, saposin C deficiency, and combined saposin deficiency (or prosaposin deficiency).

Residual Enzymatic Activity

The lysosomal storage diseases are, as outlined herein above, caused by a defective enzyme. Said defective enzyme may have no residual activity, or may have some residual activity.

Residual enzymatic activity as used herein means that although the enzyme is defective, for example caused by a mutation, the activity of the enzyme is not completely abolished, but rather reduced to a pathological level.

The present invention relates in one aspect to a bioactive agent for use in treatment of a lysosomal storage disease, and a method for treatment of an individual with a lysosomal storage disease.

In an embodiment of the present invention, the lysosomal storage disease which is treated accoding to the present invention is characterised as having residual enzymatic activity of the defective enzyme involved in the disease pathology.

In one embodiment, said residual enzymatic activity is in the range of from 0.1% to 50%, such as in the range of 0.1 to 1%, for example 1 to 2%, such as 2 to 3%, for example 3 to 4%, such as 4 to 5%, for example 5 to 6%, such as 6 to 7%, for example 7 to 8%, such as 8 to 9%, for example 9 to 10%, such as 10 to 11%, for example 11 to 12%, such as 12 to 13%, for example 13 to 14%, such as 14 to 15%, for example 15 to 20%, such as 20 to 25%, for example 25 to 30%, such as 30 to 35%, for example 35 to 40%, such as 40 to 45%, for example in the range of 45 to 50% residual enzymatic activity.

Current Treatment Modalities for LSD

There are no cures for the lysosomal storage diseases and treatment is mostly symptomatic, although bone marrow transplantation and enzyme replacement therapy (ERT) have been tried with some success. In addition, umbilical cord blood transplantation is being performed at specialized centers for a number of these diseases. Transplantation therapy is however accompanied by major side effects and often poses complications to the patients. In addition, substrate reduction therapy, a method used to decrease the accumulation of storage material, is currently being evaluated for some of these diseases.

For most of the lysosomal storage diseases, a major unmet need for providing an effective treatment modality remains.

Enzyme replacement therapy has been developed for a subset of the lysosomal storage diseases, and Cerezyme® has been on the market for a number of years for the treatment of Gaucher disease. The defective enzyme, glucocerebrosidase, is made by recombinant techniques, and given by intravenous infusion over a few hours. Treatment is not a cure and patients require lifelong treatment to halt disease progression. Some symptoms may improve by ERT.

However, for most LSDs, an efficient ERT has not been developed. This may be because the production of active enzyme has proven a difficult task, due to the complex sub-unit structure of the defective enzymes. Indeed, enzymes may fold incorrectly upon production.

For those LSDs in which ERT is available, there are drawbacks which make this form of therapy less desirable. First and foremost, ERT is a very expensive form of therapy, which is a financial burden to the society and makes it inaccessible to some patients. Also, ERT is targeted specifically at one disease only. Some side effects has been reported for Cerezyme®, including the development of an immune response, nausea, vomiting, abdominal pain, diarrhea, rash, fatigue, headache, fever, dizziness, chills, backache, and rapid heart rate as well as symptoms suggestive of allergic reactions.

The disclosures made in the present invention thus provide a new and innovative method for treatment of the lysosomal storage diseases. This is particularly relevant for these diseases for which no effective therapy has been developed, those that may benefit from a less expensive treatment, and those that may benefit from a combination therapy comprising the bioactive agent of the present invention.

As disclosed herein, the method according to the present invention provides for a treatment modality which is substantially cheaper to produce than ERT and which targets more than one specific lysosomal storage disorder.

The molecular chaperones, or heat shock proteins, are introduced herein below as the inventors have found that an interaction between heat shock protein 70 and lysosomal BMP, as introduced herein above, forms the basis for modulating lysosomal enzymatic activity, and treating lysosomal storage disorders, according to the present invention.

The Molecular Chaperones

Having spent vast amounts of energy upon first transcribing and then translating the genetic code of DNA, the cell has finally produced a polypeptide, whose function presumably is required at this point in the cell's life. However, some final obstacles has to be overcome in order to achieve a fully functional protein—one of these being correct folding of this nascent polypeptide chain. The evolutionary imperatives of achieving correct folding are obvious—not only would it be a terrible waste of energy to have synthesized a peptide without the proper conformation and hence function, but also the aggregation of such proteins in the cellular lumen could prove detrimental to the cell. This aggregation is in fact a very likely outcome, considering the intracellular environment of high protein concentration, so it comes as no surprise that a complicated and sophisticated machinery of proteins exists to assist protein folding, allowing the functional state of proteins to be maintained under such conditions. These proteins are collectively called molecular chaperones, because, like their human counterparts, they prevent unwanted interactions between their immature clients.

The molecular chaperones are found in all compartments of a cell where conformational rearrangements of proteins occur, and although protein synthesis is the major source of unfolded peptides in the cell, a challenge to the cell by high temperature or other stimuli that might render proteins structurally labile, and hence prone to unfolding and aggregation, is met with a specific cellular response involving the production of protective proteins. This response is a phenomenon observed in every cell type ranging from prokaryotes to eukaryotes and is referred to as the heat-shock- or stress-response. The proteins induced by this response are known as the heat shock proteins (HSPs), of which there exist several families. These families are composed of both sequentially, structurally and functionally related proteins, whereas chaperones from different families can differ markedly both in structure as well as cellular function. A primary example of a family of chaperones are the Hsp70 proteins, which constitute the central part of an ubiquitous chaperone system present in most compartments of eukaryotic cells, in eubacteria, and in many archae. This family has recently been implicated in other aspects of cellular homeostasis besides serving as a chaperone—most markedly through its anti-apoptotic features, its functions in immunity, and the apparent dependence of cancer cells on the upregulation of Hsp70.

The Heat Shock Protein 70 Family

Hsp70 proteins are involved in a wide range of cellular processes including protein folding and degradation of unstable cellular proteins as well as serving other cytoprotective roles. The common function of Hsp70 in these processes appears to be the binding of short hydrophobic segments in partially folded polypeptides, thereby facilitating proper folding and preventing aggregation. In eukaryotes, Hsp70 chaperones interact in vivo with different classes of proteins that serve to regulate critical steps of their functional cycle; amongst these the J-domain family protein Hsp40. Furthermore, additional partner proteins have been identified, some of which are linking Hsp70 to other chaperone systems such as the Hsp90 system.

Members of the Human Hsp70 Family

Some of the important functions attributed to the molecular chaperones include import of proteins into protein cellular compartments, folding of proteins in the cytosol, endoplasmic reticulum and mitochondria, prevention of protein aggregation and refolding of misfolded proteins. At present the human Hsp70 family includes 10 members encoded by different genes, and this section is meant to provide an overview of these family members with respect to function, expression patterns and homology. Some confusion exists about the nomenclature of the different human Hsp70 family members, although a set of general guidelines has been set forth by Tavaria et al., which provides a logical link between locus names, genes and proteins. However, as there still exists some interspecies confusion, the Hsp70 genes and proteins are referred to herein by their locus name. The name Hsp70 may refer to the two inducible Hsp70 family members with loci names HSPA1A and HSPA1B or to the whole Hsp70 family in general as evident from the consensus of the text. However, as used throughout the present invention, Hsp70 is meant to denote any of the two inducible Hsp70 family members with loci names HSPA1A and HSPA1B.

HspA1A and HspA1B

The genes transcribed from the loci HSPA1A and HSPA1B are the two heat/stress-inducible Hsp70-genes and the majority of the literature concerning human Hsp70 refers to the proteins encoded by these two genes. The genes give rise to proteins consisting of 641 amino acids, having 99% homology to each other and were the first human Hsp70 family members to be cloned and characterized. The genes are linked in the MHC-class III complex at 6p21.3, are intron-less and with promoter regions containing HSEs, enabling them to bind HSFs and induce transcription in response to a variety of cellular assaults.

```
The protein sequence for Homo sapiens heat shock 70kDa protein 1A
(HSPA1A) is (SEQ ID NO: 1) (Accession no. NM_005345.5):
MAKAAAIGIDLGTTYSCVGVFQHGKVEIIANDQGNRTTPSYVAFTDTERLIGDAAKNQVAL

NPQNTVFDAKRLIGRKFGDPVVQSDMKHWPFQVINDGDKPKVQVSYKGETKAFYPEEISSM

VLTKMKEIAEAYLGYPVTNAVITVPAYFNDSQRQATKDAGVIAGLNVLRIINEPTAAAIAY

GLDRTGKGERNVLIFDLGGGTFDVSILTIDDGIFEVKATAGDTHLGGEDFDNRLVNHFVEE

FKRKHKKDISQNKRAVRRLRTACERAKRTLSSSTQASLEIDSLFEGIDFYTSITRARFEEL

CSDLFRSTLEPVEKALRDAKLDKAQIHDLVLVGGSTRIPKVQKLLQDFFNGRDLNKSINPD

EAVAYGAAVQAAILMGDKSENVQDLLLLDVAPLSLGLETAGGVMTALIKRNSTIPTKQTQI

FTTYSDNQPGVLIQVYEGERAMTKDNNLLGRFELSGIPPAPRGVPQIEVTFDIDANGILNV

TATDKSTGKANKITITNDKGRLSKEEIERMVQEAEKYKAEDEVQRERVSAKNALESYAFNM

KSAVEDEGLKGKISEADKKKVLDKCQEVISWLDANTLAEKDEFEHKRKELEQVCNPIISGL

YQGAGGPGPGGFGAQGPKGGSGSGPTIEEVD

The nucleic acid (DNA) sequence for Homo sapiens heat shock 70kDa
protein 1A (HSPA1A) is (SEQ ID NO: 2) (Accession no. NM_005345.5):
   1 ataaaagccc agggggcaagc ggtccggata acggctagcc tgaggagctg ctgcgacagt 61 ccactacctt tttcgagagt gactcccgtt gtcccaaggc ttcccagagc gaacctgtgc 121 ggctgcaggc accggcgcgt cgagtttccg gcgtccggaa ggaccgagct cttctcgcgg 181 atccagtgtt ccgtttccag cccccaatct cagagcggag ccgacagaga gcaggggaacc 241 ggcatggcca aagccgcggc gatcggcatc gacctgggca ccacctactc ctgcgtgggg 301 gtgttccaac acggcaaggt ggagatcatc gccaacgacc agggcaaccg caccaccccc 361 agctacgtgg cctttacgga caccgagcgg ctcatcgggg atgcggccaa gaaccaggtg 421 gcgctgaacc cgcagaacac cgtgtttgac gcgaagcggc tgattggccg caagttcggc 481 gacccggtgg tgcagtcgga catgaagcac tggcctttcc aggtgatcaa cgacggagac 541 aagcccaagg tgcaggtgag ctacaagggg gagaccaagg cattctaccc cgaggagatc 601 tcgtccatgg tgctgaccaa gatgaaggag atcgccgagg cgtacctggg ctacccggtg
```

```
 661   accaacgcgg tgatcaccgt gccggcctac ttcaacgact cgcagcgcca ggccaccaag
 721   gatgcgggtg tgatcgcggg gctcaacgtg ctgcggatca tcaacgagcc cacggccgcc
 781   gccatcgcct acggcctgga cagaacgggc aaggggagc  gcaacgtgct catctttgac
 841   ctgggcgggg caccttcga cgtgtccatc ctgacgatcg acgacggcat cttcgaggtg
 901   aaggccacgg ccggggacac ccacctgggt ggggaggact tgacaacag  gctggtgaac
 961   cacttcgtgg aggagttcaa gagaaaacac aagaaggaca tcagccagaa caagcgagcc
1021   gtgaggcggc tgcgcaccgc ctgcgagagg gccaagagga ccctgtcgtc cagcacccag
1081   gccagcctgg agatcgactc cctgtttgag gcatcgact  tctacacgtc catcaccagg
1141   gcgaggttcg aggagctgtg ctccgacctg ttccgaagca ccctggagcc cgtggagaag
1201   gctctgcgcg acgccaagct ggacaaggcc cagattcacg acctggtcct ggtcggggc
1261   tccacccgca tccccaaggt gcagaagctg ctgcaggact tcttcaacgg gcgcgacctg
1321   aacaagagca tcaaccccga cgaggctgtg gcctacgggg cggcggtgca ggcggccatc
1381   ctgatggggg acaagtccga gaacgtgcag gacctgctgc tgctggacgt ggctcccctg
1441   tcgctggggc tggagacggc cggaggcgtg atgactgccc tgatcaagcg caactccacc
1501   atccccacca agcagacgca gatcttcacc acctactccg acaaccaacc cggggtgctg
1561   atccaggtgt acgagggcga gagggccatg acgaaagaca acaatctgtt ggggcgcttc
1621   gagctgagcg gcatccctcc ggcccccagg ggcgtgcccc agatcgaggt gaccttcgac
1681   atcgatgcca acggcatcct gaacgtcacg gccacggaca gagcaccgg  caaggccaac
1741   aagatcacca tcaccaacga caagggccgc ctgagcaagg aggagatcga gcgcatggtg
1801   caggaggcgg agaagtacaa agcggaggac gaggtgcagc gcgagagggt gtcagccaag
1861   aacgccctgg agtcctacgc cttcaacatg aagagcgccg tggaggatga ggggctcaag
1921   ggcaagatca gcgaggcgga caagaagaag gtgctggaca gtgtcaagag ggtcatctcg
1981   tggctggacg ccaacaccct tggccgagaag acgagtttg  agcacaagag gaaggagctg
2041   gagcaggtgt gtaaccccat catcagcgga ctgtaccagg gtgccggtgg tcccgggcct
2101   gggggcttcg ggctcagggg tcccaaggga gggtctgggt caggccccac cattgaggag
2161   gtagattagg ggccttttcca agattgctgt ttttgttttg gagcttcaag actttgcatt
2221   tcctagtatt tctgtttgtc agttctcaat ttcctgtgtt tgcaatgttg aaatttttg
2281   gtgaagtact gaacttgctt tttttccggt ttctacatgc agagatgaat ttatactgcc
2341   atcttacgac tatttcttct ttttaataca cttaactcag gccatttttt aagttggtta
2401   cttcaaagta aataaacttt aaaattcaaa aaaaaaaaa  aaaaa
```

The protein sequence for *Homo sapiens* heat shock 70kDa protein 1B (HSPA1B) is (SEQ ID NO: 3) (Accession no: NM_005346):

MAKAAAIGIDLGTTYSCVGVFQHGKVEIIANDQGNRTTPSYVAFTDTERLIGDAAKNQVAL

NPQNTVFDAKRLIGRKFGDPVVQSDMKHWPFQVINDGDKPKVQVSYKGETKAFYPEEISSM

VLTKMKEIAEAYLGYPVTNAVITVPAYFNDSQRQATKDAGVIAGLNVLRIINEPTAAAIAY

GLDRTGKGERNVLIFDLGGGTFDVSILTIDDGIFEVKATAGDTHLGGEDFDNRLVNHFVEE

FKRKHKKDISQNKRAVRRLRTACERAKRTLSSSTQASLEIDSLFEGIDFYTSITRARFEEL

CSDLFRSTLEPVEKALRDAKLDKAQIHDLVLVGGSTRIPKVQKLLQDFFNGRDLNKSINPD

EAVAYGAAVQAAILMGDKSENVQDLLLLDVAPLSLGLETAGGVMTALIKRNSTIPTKQTQI

FTTYSDNQPGVLIQVYEGERAMTKDNNLLGRFELSGIPPAPRGVPQIEVTFDIDANGILNV

TATDKSTGKANKITITNDKGRLSKEEIERMVQEAEKYKAEDEVQRERVSAKNALESYAFNM

KSAVEDEGLKGKISEADKKKVLDKCQEVISWLDANTLAEKDEFEHKRKELEQVCNPIISGL

YQGAGGPGPGGFGAQGPKGGSGSGPTIEEVD

The nucleic acid (DNA) sequence for *Homo sapiens* heat shock 70kDa
protein 1B (HSPA1B) is (SEQ ID NO: 4) (Accession no: NM_005346):

```
   1  ggaaaacggc cagcctgagg agctgctgcg agggtccgct tcgtctttcg agagtgactc
  61  ccgcggtccc aaggctttcc agagcgaacc tgtgcggctg caggcaccgg cgtgttgagt
 121  ttccggcgtt ccgaaggact gagctcttgt cgcggatccc gtccgccgtt ccagccccc
 181  agtctcagag cggagcccac agagcagggc accggcatgg ccaaagccgc ggcgatcggc
 241  atcgacctgg gcaccaccta ctcctgcgtg ggggtgttcc aacacggcaa ggtggagatc
 301  atcgccaacg accagggcaa ccgcaccacc ccagctacg tggccttcac ggacaccgag
 361  cggctcatcg ggatgcggc caagaaccag gtggcgctga cccgcagaa caccgtgttt
 421  gacgcgaagc ggctgatcgg ccgcaagttc ggcgacccgg tggtgcagtc ggacatgaag
 481  cactggcctt tccaggtgat caacgacgga gacaagccca aggtgcaggt gagctacaag
 541  ggggagacca aggcattcta ccccgaggag atctcgtcca tggtgctgac caagatgaag
 601  gagatcgccg aggcgtacct gggctacccg gtgaccaacg cggtgatcac cgtgccggcc
 661  tacttcaacg actcgcagcg ccaggccacc aaggatgcgg gtgtgatcgc ggggctcaac
 721  gtgctgcgga tcatcaacga gcccacggcc gccgccatcg cctacggcct ggacagaacg
 781  ggcaagggg agcgcaacgt gctcatcttt gacctgggcg ggggcacctt cgacgtgtcc
 841  atcctgacga tcgacgacgg catcttcgag gtgaaggcca cggccgggga cacccacctg
 901  ggtggggagg actttgacaa caggctggtg aaccacttcg tggaggagtt caagagaaaa
 961  cacaagaagg acatcagcca gaacaagcga gccgtgaggc ggctgcgcac cgcctgcgag
1021  agggccaaga ggaccctgtc gtccagcacc caggccagcc tggagatcga ctccctgttt
1081  gagggcatcg acttctacac gtccatcacc agggcgaggt tcgaggagct gtgctccgac
1141  ctgttccgaa gcaccctgga gcccgtggag aaggctctgc gcgacgccaa gctggacaag
1201  gcccagattc acgacctggt cctggtcggg ggctccaccc gcatccccaa ggtgcagaag
1261  ctgctgcagg acttcttcaa cgggcgcgac ctgaacaaga gcatcaaccc cgacgaggct
1321  gtggcctacg ggcggcggt gcaggcggcc atcctgatgg gggacaagtc cgagaacgtg
1381  caggacctgc tgctgctgga cgtggctccc ctgtcgctgg ggctggagac ggccggaggc
1441  gtgatgactg ccctgatcaa gcgcaactcc accatcccca ccaagcagac gcagatcttc
1501  accacctact ccgacaacca acccgggtg ctgatccagg tgtacgaggg cgagagggcc
1561  atgacgaaag acaacaatct gttggggcgc ttcgagctga gcggcatccc tccggccccc
1621  aggggcgtgc cccagatcga ggtgaccttc gacatcgatg ccaacggcat cctgaacgtc
1681  acggccacgg acaagagcac cggcaaggcc aacaagatca ccatcaccaa cgacaagggc
1741  cgcctgagca aggaggagat cgagcgcatg gtgcaggagg cggagaagta caaagcggag
1801  gacgaggtgc agcgcgagag ggtgtcagcc aagaacgccc tggagtccta cgccttcaac
1861  atgaagagcg ccgtggagga tgaggggctc aagggcaaga tcagcgaggc ggacaagaag
1921  aaggttctgg acaagtgtca agaggtcatc tcgtggctgg acgccaacac cttggccgag
1981  aaggacgagt ttgagcacaa gaggaaggag ctggagcagg tgtgtaaccc catcatcagc
```

```
2041  ggactgtacc  agggtgccgg  tggtcccggg  cctggcggct  tcggggctca  gggtcccaag 2101  ggagggtctg  ggtcaggccc  taccattgag  gaggtggatt  aggggcctt   gttctttagt 2161  atgtttgtct  ttgaggtgga  ctgttgggac  tcaaggactt  tgctgctgtt  ttcctatgtc 2221  atttctgctt  cagctctttg  ctgcttcact  tctttgtaaa  gttgtaacct  gatggtaatt 2281  agctggcttc  attatttttg  tagtacaacc  gatatgttca  ttagaattct  ttgcatttaa 2341  tgttgatact  gtaagggtgt  ttcgttccct  ttaaatgaat  caacactgcc  accttctgta 2401  cgagtttgtt  tgttttttt   tttttttttt  tttttgctt   ggcgaaaaca  ctacaaaggc 2461  tgggaatgta  tgtttttata  atttgtttat  ttaaatatga  aaaataaaat  gttaaacttt 2521  aaaaaaaaaa  aaaaaaaaaa  aaaaaaaaaa  a
```

HspA1L and HspA2

Two Hsp70 family members have been termed "chauvinist genes" because male germ cells favor their expression with strong prejudice. The hspA1L gene is a constitutively expressed intron-less Hsp70 family member located 4 kb telomeric to the HSPA1A locus in the same MHC-class III complex on chromosome 6. It is expressed in low amounts both before and after heat shock but with the expression pattern favoring the testes in mouse, rat and humans with the 641 amino acids (aa) protein being 90% homologous to HspA1A. The hspA2 gene was first isolated from a mouse genomic library and has later been shown to be constitutively expressed albeit in low levels in various tissues in the human body including skeletal muscle, ovary, small intestine, colon, brain, placenta and the kidneys, but highly expressed in testis. Its expression, or rather lack thereof, has been connected with abnormal human spermatogenesis and male hspA2$^{(-/-)}$ mice are sterile. The gene is located on chromosome 14, giving rise to a 639 aa protein with 84% homology to HspA1A, although the exact location is subject to discussion as two papers have presented different loci positions—14q24.1 vs. 14q22.

HspA6 and HspA7

The hspA6 and hspA7 genes are heat inducible members of the Hsp70 family with no apparent counterparts in mice. They contain HSEs in their promoter-sites and the genes are intron-less. They are co-localized on chromosome 1 and are 94% homologous to each other in the nucleotide sequence. However, only HspA6 is functional as the hspA7 gene harbors a single nucleotide insertion generating a premature stop codon at +1324. The HspA6 protein is 643 aa long and shows 77% homology to HspA1A and HspA1B.

HspA5 and HspA9

The hspA5 and hspA9 genes are the two compartment-specific members of the Hsp70 family. The 655 aa HspA5 protein is located in the endoplasmic reticulum (ER) and facilitates folding and transport of newly synthesized proteins in this compartment. The protein is 64% homologous to HspA1A, the gene being located at 9q34. The 679 aa HspA9 protein is located in the mitochondria where it assists in folding of proteins after their transport across the mitochondrial membrane. HspA9 is located at 5q31.1, the protein being 52% homologous to HspA1A.

HspA8

The cognate Hsp70 member known as Hsc70 is encoded by a gene named hspA8 at 11q24, giving rise to a 646 aa protein with 86% homology to HspA1A, and is constitutively expressed in all tissues and cell lines. The protein is analogous to Hsp70 in its cellular functions, providing the required chaperoning under normal circumstances, but has also been ascribed a role in the un-coating of clathrin-coated vesicles as well as in chaperone-mediated autophagy.

HspA3 and HspA4

These will not be discussed here, as there is doubt as to whether HSPA3 exists at all and since HSPA4 is most likely a member of the Hsp110 family and nothing is known about it so far, except for its chromosomal location at 5q31.1-2.

TABLE 1

List of the Human Hsp70 Gene Family.

| Locus | Name Used herein, Gene/Protein | Position | % aa Homology to HSPA1A | Alternative Names |
|---|---|---|---|---|
| HSPA1A | hspA1A/HspA1A (Hsp70) | 6p23.1 | 100 | Hsp70; Hsp72; Hsp70-1 |
| HSPA1B | hspA1B/HspA1B (Hsp70) | 6p23.1 | 99 | Hsp70; Hsp72; Hsp70-2 |
| HSPA1L | hspA1L/HspA1L | 6p23.1 | 90 | Hsp70-Hom; Hsp70t |
| HSPA2 | hspA2/HspA2 | 14q24.1 | 84 | Hsp70-3 |
| HSPA4 | hspA4/HspA4 | 5q31.1 | 31 | Hsp70RY; APG-2 |
| HSPA5 | hspA5/HspA5 | 9q34 | 64 | BiP; GRP78 |
| HSPA6 | hspA6/HspA6 | 1q | 84 | Hsp70-6; Hsp70B' |
| HSPA7 | hspA7/HspA7 | 1q | — | Hsp70-7; Hsp70B |
| HSPA8 | hspA8/HspA8 (Hsc70) | 11q24 | 86 | Hsc70; Hsp73 |
| HSPA9 | hspA9/HspA9 | 5q31.1 | 52 | GRP75; PBP74; mtHsp75; mortalin; mot-2 |

The genes are listed according to locus name, names used herein, chromosomal location (position), amino acid homology to HspA1A as well as alternative names often seen in the literature.

Transcriptional Regulation of Hsp70

Genomic foot printing of the human Hsp70 promoter has revealed that heat shock/stress induces a rapid binding of heat shock transcription factors (HSF) to a region encompassing nGAAn sequences named heat shock elements (HSEs). Under normal conditions Hsp70 is bound to HSFs, which reside in the cytosol, but during stress the HSFs are separated from Hsp70 and adapt a homotrimeric conformation upon phosphorylation by PKC or other serine/threonine kinases. The HSF trimers enter the nucleus, where they bind HSEs located in the promoter region of Hsp70 genes and become further phosphorylated by HSF kinases.

Three HSFs have so far been characterized in humans (HSF1, HSF2 and HSF4). HSF1 is the major transcription factor activated under most stress conditions and responds to a wide range of stimuli, which can be categorized into physiological (e.g. cell division, hormonal stimulation), pathological (e.g. infections, fever, inflammation, malignancy) and environmental conditions (e.g. heat shock, heavy metals, ethanol). HSF2 responds only to hemin, whereas HSF4 is preferentially expressed in the human heart, pancreas, brain and skeletal muscle, lacks the c-terminal hydrophobic repeat that is shared among all vertebrate HSFs and appears to repress expression of HSPs. The Hsp70 gene regulation responsible for synthesis of the constitutively expressed Hsp70 (Hsc70) is not clearly understood, but HSFs do not seem to be involved.

Although the HSFs are the most prominent of the factors regulating HSP expression, other transcription factors have been shown to possess the same capability. Specific CCAAT-box binding factors (CBF) have been shown to induce Hsp70 transcription, the tumor-suppressor p53 can repress transcription by binding to the promoter-region of Hsp70 and by neutralizing CBF, and HSFs can be antagonized by the heat shock factor binding protein 1 (HSBP1), which in this way attenuates Hsp70 transcription.

Structural and Functional Properties of Hsp70

The structure and function of the Hsp70 system are best understood for the eubacterial Hsp70, DnaK, its Hsp40 co-chaperone DnaJ and the nucleotide exchange factor GrpE. However, the mechanism is generally considered to be analogous in eukaryotes, although evidence suggests an uncoupling of GrpE. This section will focus on the eukaryotic Hsp70 system, but will also include comments on the eubacterial system, where this is considered appropriate.

Hsp70 is comprised of two functional entities—an N-terminal ATPase domain and a smaller C-terminal peptide-binding domain. The ATPase domain is comprised of two subdomains separated by a cleft containing the nucleotide-binding site, which determines the peptide-binding properties of the C-terminal domain. When ATP is bound, peptide substrates bind and dissociate rapidly, albeit with low affinity, whereas in a state where either no nucleotide or ADP is bound to the N-terminal domain, the rates of peptide binding and dissociation decrease and the affinity increases. ATP hydrolysis thus serves as a molecular switch between two states of Hsp70, the cycling of which is regulated by the J-domain family protein Hsp40 in eukaryotes and DnaJ and GrpE in eubacteria. The N-terminal J-domain of Hsp40 binds to Hsp70 accelerating ATP-hydrolysis, hereby facilitating peptide capture, whereas the C-terminal part of Hsp40 functions as a chaperone by recognizing hydrophobic peptides, whereby Hsp70 is recruited to nascent polypeptide chains. It is important to note that the molecular chaperones do not provide specific steric information for the folding of the bound protein, but rather inhibit unproductive interactions, thus allowing the protein to fold more efficiently into its native structure.

In eubacteria, GrpE induces the release of ADP from DnaK (bacterial Hsp70), whereas for eukaryotic Hsp70 proteins such a factor appears to be dispensable because the rate-limiting step in this ATPase cycle is not the dissociation of bound ADP but rather the ATP-hydrolysis itself. However, additional proteins serve to regulate Hsp70 function in eukaryotes; the homo-oligomeric protein Hip (Hsp70 interacting protein) serving as a positive regulator by stabilizing the ADP-bound state of Hsp70, whereas the proteins Carboxy-terminus of Hsp70-binding protein (CHIP) and Bcl-2-associated athanogene-1 (Bag-1) both have inhibitory effects—CHIP by inhibiting the ATPase activity of Hsp70 and Bag-1 by antagonizing the refolding activity of Hsp70. Further interactions are provided by the two human Hsp40 proteins Hdj1 and Hdj2, which, besides their Hsp40 functions (described above), have been shown to facilitate the coupling of Hsp70 and Hsp90 through Hop (Hsp-organizing protein), an adaptor protein which physically links the chaperones through its two tetratricopeptide repeat (TPR) domains that bind the extended C-terminal sequences of Hsp70 and Hsp90, respectively. It has recently been shown that some of the above mentioned proteins are regulatory in the transfer of non-native or irreversible misfolded proteins from the chaperones to the ubiquitin-proteasome machinery. The protein CHIP is, apart from its negative regulatory role on Hsp70, able to associate with Hsp90 through an N-terminal TPR domain and targets Hsp90 substrates for degradation through a C-terminal ubiquitin ligase domain, but is also capable of cooperating functionally with BAG-1, which binds to Hsp70 (as well as the proteasome. These findings provide a possible link between the mechanisms that integrate chaperone-assisted folding and proteolytic degradation, the two main components of protein quality control in the cytosol.

Cytoprotection via Hsp70

Apart from its anti-apoptotic abilities as a consequence of being a molecular chaperone, i.e. facilitating protein folding under otherwise denaturing conditions, Hsp70 is also able to affect the survival of cells in various other ways, including protection of mitochondrial function after ischemia-reperfusion injury, blocking activation of the stress kinase c-jun N-terminal kinase (JNK) upon stimulation of primary fibroblasts with TNF, and a Hsp70/Bag-1 complex has been proposed to regulate cell growth and mitogenesis during conditions of cellular stress. The ability of Hsp70 to protect cells from cell death induced by an array of stimuli such as TNF, TRAIL, oxidative stress, UV-radiation and the anticancer drugs doxorubicin, etoposide and taxol further emphasize its anti-apoptotic features. Finally, reports have also provided evidence of more direct interactions between Hsp70 and the apoptotic machinery as Hsp70 has been shown to antagonize apoptosis-inducing factor (AIF), as well as exert an anti-apoptotic function downstream of caspase-3.

Recent evidence also suggests that parts of the potent cytoprotective effect of Hsp70 are due to stabilization of lysosomal membranes. In evidence of this, the depletion of Hsp70 triggers an early permeabilization of lysosomal membranes and cathepsin-mediated cell death in cancer cells, and exogenous Hsp70 effectively inhibits lysosomal destabilization induced by various stresses. Furthermore, mice deficient for Hsp70 suffer from pancreatitis caused by the leakage of lysosomal proteases into the cytosol. All of these events stress the role of Hsp70 as an important regulator of PCD and hence survival factor for cells.

Hsp70 in Cancer

Hsp70 is often over-expressed in malignant human tumors, and its expression correlates with poor prognosis in breast and endometrial tumors. In line with this, Hsp70 increases the tumourigenic potential of rodent cells implanted into immuno-compromised or syngeneic animals.

The role of Hsp70 as an essential factor for cancer cell survival is further substantiated from a report by Wei et al., who made the first depletion-study of Hsp70 in cancer cells. The results indicated that when Hsp70 expression was inhibited in various cancer cell lines by the use of an antisense-oligomer, inhibition of cell proliferation and subsequent apoptosis was induced. This work has been substantiated in a series of experiments in which adenoviral antisense-mediated depletion of Hsp70 triggers a tumor cell-specific lysosomal death program.

In vivo studies utilizing orthotopic xenografts of glioblastoma and breast carcinomas as well as sub-cutaneous xenografts of colon-carcinoma in immunodeficient mice has further demonstrated the anti-cancer potential of Hsp70 depletion, as the tumors of mice receiving locoregional application of the above-mentioned adenoviral construct showed massive apoptosis-like cell death and recruitment of macrophages. These studies clearly demonstrate the dependence of some tumors upon the presence of Hsp70, although other studies have argued that the cytotoxicity observed in cell culture upon adenovirus-mediated depletion of Hsp70 is due to a combination of virally mediated cell-stress and Hsp70-downregulation. Despite this controversy, the cytotoxicity in cell culture induced by the depletion of Hsp70 was not dependent on caspases since neither overexpression of Bcl-2 nor pharmacological inhibition of caspases could rescue the cells. Rather, the triggering of LMP and release of cathepsins to the cytosol was the likely death-inducing events as the inhibition of cysteine cathepsins conferred significant cytoprotection. Furthermore, depletion of Hsp70 in the before mentioned tumor xenografts in mice lead to cathepsin release and tumor cell death.

As mentioned earlier, one of the cytoprotective mechanisms of Hsp70, which many cancer cells seem to have adapted, is the translocation of Hsp70 to the endo-lysosomal compartment where it serves a membrane-protective role. This translocation may not only be driven by the need to protect the lysosomal membranes, as studies have shown that more than 50% of tumors show localization of Hsp70 on the plasma-membrane surface—an area which is directly connected with the endo-lysosomal compartment via endocytosic and secretory events, as described earlier. The surface-exposed Hsp70 presents a unique epitope which can act as a recognition structure for natural killer (NK) cells, stimulating their proliferation and cytolytic activity. NK cells activated by this Hsp70 peptide sequence has been shown to inhibit tumour growth in mice with severe combined immunodeficiency (SCID), a possible mechanism for this could be that the cell-surface-bound Hsp70 mediates apoptosis by the specific binding and uptake of granzyme B, independent of perforin.

As previously written, the endo-lysosomal membranes and plasma membranes are constantly interchanged. Thus, the presence of Hsp70 on the surface of cancer cells could be an "unfortunate" consequence of two events that promote tumor progression; the secretion of cathepsins, which promotes invasion and angiogenesis, and the localization of Hsp70 on the lysosomal membranes, which prevents accidental release of cysteine cathepsins to the cytosol and ensuing cell death.

Extracellular Hsp70

As evident from the former paragraphs, the intracellular functions of Hsp70 are essential for proper cell homeostasis, not least so in the face of noxious challenges. However, interesting roles are also emerging for extracellular Hsp70 (eHsp70) especially when it comes to immune and inflammatory responses, which again might have important roles for the clearance of cancer cells. Furthermore, involvement in a general physiological adaptation to stress and protection versus cellular damage are also emerging themes for eHsp70.

Extracellular Hsp70 and Neuroprotection

The first evidence for the presence of eHsp70 came from studies in the squid giant axon, in which it was shown that elevation of temperature induced a set of heat shock proteins in the glial sheath surrounding the axon which where transferred into the axon. These findings where soon reproduced in cultured rat embryo cells, and importantly, already at this point, evidence was presented for a non-classical pathway of exocytosis being responsible for the release of Hsp70 as neither monensin nor colchicine, both inhibitors of the classical secretory pathway, could block the secretion of Hsp70. Since these publications, other reports have provided examples of release of Hsps by glia and the uptake by neurons in various animal model systems such as frogs, crayfish and rats. Support of a role for glia cells as sources of eHsp70 in humans was provided by a study of cultured human glioblastoma cells. This study showed that under control conditions the cells released ~10 µg of Hsp70 per million cells to the medium in a time period of 24 h. This release was increased 2.5-5-fold when a 20 min heat shock was applied in the beginning of the time period. Importantly, this study also showed that the release of eHsp70 was greater than what could be accounted for by cell death. These data all support the originally suggested hypothesis set forth by Tytell et al., that glial release of Hsps may be a way to support neuron function during metabolic stress.

In vivo evidence for eHsp70 having a neuroprotective role during acute stress comes from a variety of studies. A study by Tidwell et al. found that eHsp70 is capable of reducing the amount of post-axotomy motor neuron cell death, when eHsp70 was applied via a gel-sponge after axotomy. In the same study, increased survival of dorsal root ganglion sensory neuron cells where also observed upon Hsp70 administration, albeit this depended on slightly higher doses of Hsp70 than the motor neurons. In addition, eHsp70 has been shown to protect motor neurons otherwise destined to die during chick embryonic development, and also protect motor neurons isolated from chick spinal cords upon trophic factor deprivation. An in vivo protective role for eHsp70 has also been described when it comes to light damage of the retina. In this study, Yu et al., intravitreally injected a solution of recombinant Hsp70 and Hsc70 after exposure to damage-inducing light at a dose which had previously been described to cause extensive photoreceptor degeneration. Interestingly, the presence of the eHsp70 mixture in the vitreous chamber of the right eye resulted in significantly more photoreceptors surviving in the retina. Furthermore, evaluation of uptake of fluorescein-labelled Hsc/Hsp70 demonstrated that it was present in the retina 6 h after administration. Extracellular Hsp70 administered via intranasal treatment has also been shown to prevent the consequences of unavoidable stress in rats and it was recently described that intraperitoneally injected recombinant human Hsp70 was effective in increasing the lifespan, delaying symptom onset, preserving motor function and prolonging motor neuron survival in a mouse model of amyotrophic lateral sclerosis. Additional in vitro work using Hsp70 or the Hsc/Hsp70 mixture in neuronal systems has furthermore shown that eHsp70 can enhance neuronal cell stress tolerance and reduce polyglutamine toxicity and aggregation.

Extracellular Hsp70 and Immunity

Beside roles in cytoprotection, both plasma membrane-associated as well as free systemic eHsp70 have been documented to serve roles in immunity. Considering that one of the major functions of Hsp70 is to chaperone intracellular proteins, it is perhaps not surprising that it can be involved in binding of immunogenic peptides and assist in the presentation of these by major histocompatibility complex (MHC) class 1 molecules. Furthermore, tumor-derived eHsp70 has been shown to chaperone immunogenic peptides and selectively bind to antigen presenting cells (APC). Following receptor-mediated endocytosis these Hsp70-peptide complexes are then presented on MHC class 1 molecules leading to a cytotoxic t-cell response. In addition to the chaperoning of self-antigens, Hsp70 is also capable of binding microbial peptides and unmethylated CpG motifs in bacterial DNA.

In addition to its role as an antigen-presenting chaperone, eHsp70 has also been implicated in the stimulation of innate immunity. Whilst a number of cell types have been shown to release Hsp70, eHsp70 has also been shown to bind to a number of receptors on different leucocyte sub-populations including natural killer (NK) cells, macrophages, monocytes and dendritic cells. The receptors involved in eHsp70 recognition mainly include pattern recognition receptors (PRR's) and consist of a variety of receptors from different receptor families such as the toll like receptors (TLR), scavenger receptors and c-type lectins. Upon receptor binding, eHsp70 is capable of eliciting a wide cytokine-response including release of pro-inflammatory cytokines such as TNF-a, IL-1b, IL-12, IL-6 and GM-CSF, a process triggered by translocation of NF-kB to the nucleus, suggesting a cytokine action of eHsp70, which has also led to the suggestion of coining the term chaperokine to eHsp70 in order to better describe the uniqe functions of eHsp70 as both a chaperone and cytokine.

Much of the in vivo work on a role of eHsp70 in immunity has been conducted in rodent models. For example, increases in eHsp70 concentration in response to tail-shock were associated with reduced inflammation and quicker recovery times following a sub-cutaneous E. Coli-injection. In addition, in vivo delivery of Hsp70 into mice accelerated wound closure, a feature which was likely due to enhanced macrophage phagocytosis of wound debris.

Evidence for the immunomodulatory roles of Hsp70 in humans is lacking, but studies have demonstrated relationships between increased eHsp70 and improved prognosis/outcome for brain trauma, although the contrary has also been shown. However, it is also known that concentrations of eHsp70 decline with advancing age, which may be indicative of an age-related reduced ability to mount a full stress-response, which again could account for the increased morbidity and mortality seen with ageing, although this remains purely speculative.

Release of Hsp70

Aside for the data demonstrating transfer of eHsp70 between neighboring cells such as in the glia/axon model, several reports have documented the presence of free eHsp70 in the circulation. For Hsp70 to be present in this compartment, it necessarily has to be released from an organ/cell. Two major ways of achieving this are usually considered. One is a passive way in which the observation of eHsp70 in the peripheral circulation is the consequence of release from an intracellular pool of Hsp70 due to cell lysis or death. Alternatively, or perhaps additionally, Hsp70 is actively released via a non-classical exocytotic pathway.

It has been suggested that Hsp70 along with other heat shock proteins are only released under pathological circumstances resulting in necrotic death and not during programmed cell death. No doubt, severe trauma and pathological conditions resulting in necrosis can lead to the release of Hsp70 to the bloodstream. This has been well documented and would also logically be expected. Recent studies however, have shown that Hsp70 can be released from intact cells by active mechanisms and that the degree of stimulus determines the mode of release. Strong evidence for the non-necrotic release of Hsp70 also comes from studies on exercise-induced release of eHsp70 to the peripheral bloodstream. Dependent on the mode of exercise (the higher the physical strain, the more release) major increases of eHsp70 can be detected in the peripheral bloodstream, and importantly, no known studies have reported a direct correlation between eHsp70 and markers of muscle damage. That eHsp70 can be released regardless of cellular or tissue damage has furthermore been elegantly demonstrated by Fleshner and co-workers who have shown that psychological stress such as predatory fear and electric shock can evoke a stress induced eHsp70 release, a process which was suggested to be dependent on cathecholamine signaling.

The way by which hsp70 leaves the cell is still unclear though, not least so because Hsp70 does not contain any classical peptide leader sequence, which could target it for secretion. In addition, as classical secretion was already questioned early, this suggests that alternate mechanisms for eHsp70 release must exist. It has been demonstrated that eHsp70 can be released in vesicles characterized as exosomes, but evidence has also been presented that eHsp70 can be released as free eHsp70, both in cellular systems as well as in vivo. It has been suggested that lipid rafts are needed for eHsp70 release although this has also been disputed. Moreover, it has been shown that a functional lysosomal compartment is necessary for release of eHsp70 and that this release is accompanied by the presence of lysosomal marker proteins on the surface of the cells, suggesting a secretion dependent on plasma- and lysosomal membrane fusion. Regardless of whether the release is via exosomes or via direct release from lysosomes, it is interesting to note that some sort of secretory MVB/late endosomal/lysosomal compartment is apparently involved in all modes of release.

As catecholamines via the $\alpha_1$-adrenergic receptor can lead to intracellular calcium-fluxes, and since the same calcium-fluxes has been suggested to cause exocytosis of exosomes, multivesicular bodies and lysosomes, a current hypothesis is that under times of stress, increases in noradrenaline acting upon $\alpha_1$-adrenergic receptors results in a calcium flux within the cell and a subsequent release of Hsp70 within exosomes.

Bioactive Agent According to the Present Invention

The present invention relates in one embodiment to the modulation of enzymatic activity, wherein said enzyme interacts with BMP, by the use of a bioactive agent capable of increasing the intracellular concentration and/or activity of Hsp70.

The modulation of enzymatic activity according to the present invention can be obtained by providing one of the following classes of compounds and therapies, which increases the intracellular concentration and/or activity of Hsp70:

Hsp70, or a functional fragment or variant thereof
Hsp70 inducers and co-inducers
    Small-molecule drugs such as Bimoclomol and Arimoclomol
    Membrane fluidizers such as benzyl alcohol
    Sub-lethal heat-therapy (≤42° C.) or hyperthermia
    Certain drugs from the group of anti-inflammatory and anti-neoplastic drugs
    Cellular stress
        Reactive oxygen species (ROS)
        Adrenalin, noradrenalin
        UV light
        Radiation therapy A bioactive agent according to the present invention is thus any agent, chemical or compound that increases the intracellular concentration and/or activity of Hsp70; and includes HSP70 itself, or a functional fragment or variant thereof, and any Hsp70 inducer or co-inducer known to the skilled person, whereby said bioactive agent is capable of modulating the activity of an enzyme which interacts with BMP.

It follows that a bioactive agent may increase the intracellular concentration and/or activity of Hsp70 either directly or indirectly.

In one embodiment, the bioactive agent according to the present invention is Hsp70, or a functional fragment or variant thereof.

In another embodiment, the bioactive agent according to the present invention is an Hsp70 inducer or co-inducer.

In one embodiment, the bioactive agent according to the present invention comprises a combination of Hsp70, or a functional fragment or variant thereof, and an Hsp70 inducer or co-inducer.

It is an aspect of the present invention to provide a bioactive agent capable of increasing the intracellular concentration and/or activity of Hsp70, for use as a medicament.

It is a further aspect of the present invention to provide a bioactive agent capable of increasing the intracellular concentration and/or activity of Hsp70, for use in the treatment of a lysosomal storage disorder.

It is a further aspect of the present invention to provide a bioactive agent capable of increasing the intracellular concentration and/or activity of Hsp70, for use as a medicament or for use in the treatment of a lysosomal storage disorder.

In one embodiment, said treatment may be prophylactic, curative or ameliorating. In one particular embodiment, said treatment is prophylactic. In another embodiment, said treatment is curative. In a further embodiment, said treatment is ameliorating.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

In a particular embodiment, said lysosomal storage disorder is Niemann-Pick disease type A or B. In another particular embodiment, said lysosomal storage disorder is Farber disease. In another particular embodiment, said lysosomal storage disorder is Krabbe disease. In another particular embodiment, said lysosomal storage disorder is Metachromatic leukodystrophy. In another particular embodiment, said lysosomal storage disorder is Sialidosis. In another particular embodiment, said lysosomal storage disorder is Fabry disease. In yet another particular embodiment, said lysosomal storage disorder is Gaucher disease. In yet another particular embodiment, said lysosomal storage disorder is saposin-deficiency.

It is also an aspect of the present invention to provide a bioactive agent capable of increasing the intracellular concentration and/or activity of Hsp70, for use in the treatment of a lysosomal storage disorder, wherein said lysosomal storage disorder is one, such as two, for example three, such as four, for example five, such as six, for example seven disorders selected from the group consisting of Niemann-Pick disease, Farber disease, Krabbe disease, Fabry disease, Gaucher disease, Metachromatic leukodystrophy, Sialidosis and saposin-deficiency.

It follows that the bioactive agent according to the present invention may be used for the treatment of a subset of the lysosomal storage disorders selected from the group consisting of Niemann-Pick disease, Farber disease, Krabbe disease, Fabry disease, Gaucher disease, Metachromatic leukodystrophy, Sialidosis and saposin-deficiency.

In one particular embodiment, the bioactive agent according to the present invention may be used for the treatment of Niemann-Pick disease type A and B and Farber disease.

In one embodiment, the bioactive agent according to the present invention comprises a combination of Hsp70, or a functional fragment or variant thereof, and a substance which increases the interaction between Hsp70 and BMP.

It is a still further aspect of the present invention to provide the use of a bioactive agent capable of increasing the intracellular concentration and/or activity of Hsp70, for the manufacture of a medicament for treatment of a lysosomal storage disorder.

Bioactive Agent—Hsp70, or a Functional Fragment or Variant Thereof

The present invention relates in one embodiment to the modulation of enzymatic activity, wherein said enzyme interacts with BMP, by the use of Hsp70, or a functional fragment or variant thereof.

It is an aspect of the present invention to provide Hsp70, or a functional fragment or variant thereof, for use as a medicament.

It is a further aspect of the present invention to provide Hsp70, or a functional fragment or variant thereof, for use in treating lysosomal storage disorders.

It is a still further aspect of the present invention to provide the use of Hsp70, or a functional fragment or variant thereof, for the manufacture of a medicament for treating lysosomal storage disorders.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

It is understood that Hsp70, or a functional fragment or variant thereof, according to the present invention may be any natural or synthetic product, and may be produced by any conventional technique known to the person skilled in the art.

In one embodiment, Hsp70, or a functional fragment or variant thereof, is purified from a natural source. Said natural source may be any plant, animal or bacteria which expresses, or may be induced to express, Hsp70 in a form suitable for administering to an individual in need thereof.

In a preferred embodiment however, Hsp70, or a functional fragment or variant thereof, is made synthetically. It follows that Hsp70, or a functional fragment or variant thereof, may in one preferred embodiment be a recombinant protein made by conventional techniques therefore and as such is denoted rHsp70.

The Hsp70 according to the present invention, synthetic or natural, may have a sequence which is derived from any suitable species of plant, animal or bacteria. In one embodiment, said rHsp70 is derived from a mammal. Said mammal may be selected form the group consisting of human (homo sapiens), mouse (mus musculus), cow, dog, rat, ferret, pig, sheep, and monkey. In another embodiment, said rHsp70 is derived from bacteria.

Hsp70 is characterized in part by having a very high degree of interspecies sequence conservation, thus possibly allowing for Hsp70 derived from one species to be used in another species without eliciting a harmful immune response.

In one particular embodiment, said rHsp70 has a sequence derived from human Hsp70.

In one particular embodiment, said rHsp70 has a sequence derived from more than one species. Said Hsp70, or a functional fragment or variant thereof, may thus in one embodiment be a chimera.

A recombinant protein is a protein that is derived from recombinant DNA. Recombinant DNA is a form of DNA that does not exist naturally, which is created by combining DNA sequences that would not normally occur together. In terms of genetic modification, recombinant DNA is introduced through the addition of relevant DNA into an existing organismal DNA, such as the plasmids of bacteria, to code for different traits for a specific purpose. It differs from genetic recombination, in that it does not occur through processes within the cell, but is engineered by man.

In one embodiment, the Hsp70 according to the present invention has 100% homology to the wild-type Hsp70 protein. In another embodiment, the Hsp70 according to the present invention has less than 100% homology to the wild-type Hsp70 protein, such as between 99.9 to 95% homology, for example 95 to 90% homology, such as 90 to 85% homology, for example 85 to 80% homology, such as 80 to 75% homology, for example 75 to 60% homology to the wild-type protein.

Regardless of the degree of homology, any variant of Hsp70 that retains its ability to modulate the enzymatic activity of an enzyme which binds to BMP is encompassed by the present invention.

In one embodiment, the bioactive agent is Hsp70. In one embodiment, said Hsp70 is full length Hsp70.

It is also an embodiment to provide a functional fragment or variant of Hsp70. As defined herein, a functional fragment or variant is any fragment of Hsp70 having the desired function, which in terms of the present invention is a capability to modulate the enzymatic activity of an enzyme, wherein said enzyme interacts with BMP.

In one embodiment, the bioactive agent is a functional fragment or variant of Hsp70.

In one embodiment, the bioactive agent is a functional fragment or variant of Hsp70, in which Hsp70 is modified by deletion(s), addition(s) or substitution(s) of the wild type Hsp70.

The wild type Hsp70 protein has a total length of 641 amino acids. A fragment of Hsp70 is in one embodiment meant to comprise any fragment with a total length of less than the wild type protein of 641 amino acids, such as less than 625 amino acids, for example less than 600 amino aids, such as less than 575 amino acids, for example less than 550 amino aids, such as less than 525 amino acids, for example less than 500 amino aids, such as less than 475 amino acids, for example less than 450 amino aids, such as less than 425 amino acids, for example less than 400 amino aids, such as less than 375 amino acids, for example less than 350 amino aids, such as less than 325 amino acids, for example less than 300 amino aids, such as less than 275 amino acids, for example less than 250 amino aids, such as less than 225 amino acids, for example less than 200 amino aids, such as less than 175 amino acids, for example less than 150 amino aids, such as less than 125 amino acids, for example less than 100 amino aids, such as less than 75 amino acids, for example less than 50 amino aids, such as less than 25 amino acids.

The wild type Hsp70 protein has a total length of 641 amino acids. A fragment of Hsp70 is in one embodiment meant to comprise any fragment with a total length of more than 10 amino acids, such as more than 25 amino acids, for example more than 50 amino aids, such as more than 75 amino acids, for example more than 100 amino acids, such as more than 125 amino acids, for example more than 150 amino aids, such as more than 175 amino acids, for example more than 200 amino aids, such as more than 225 amino acids, for example more than 250 amino acids, such as more than 275 amino acids, for example more than 300 amino aids, such as more than 325 amino acids, for example more than 350 amino aids, such as more than 375 amino acids, for example more than 400 amino aids, such as more than 425 amino acids, for example more than 450 amino acids, such as more than 475 amino acids, for example more than 500 amino aids, such as more than 525 amino acids, for example more than 550 amino aids, such as more than 575 amino acids, for example more than 600 amino aids, such as more than 625 amino acids.

It follows that the total length of the fragment of Hsp70 according to the present invention may in one embodiment be within the range of 5 to 25 amino acids, such as 25 to 50 amino acids, for example 50 to 75 amino acids, such as 75 to 100 amino acids, for example 100 to 125 amino acids, such as 125 to 150 amino acids, for example 150 to 175 amino acids, such as 175 to 200 amino acids, for example 200 to 225 amino acids, such as 225 to 250 amino acids, for example 250 to 275 amino acids, such as 275 to 300 amino acids, for example 300 to 325 amino acids, such as 325 to 350 amino acids, for example 350 to 375 amino acids, such as 375 to 400 amino acids, for example 400 to 425 amino acids, such as 425 to 450 amino acids, for example 450 to 475 amino acids, such as 475 to 500 amino acids, for example 500 to 525 amino acids, such as 525 to 550 amino acids, for example 550 to 575 amino acids, such as 575 to 600 amino acids, for example 600 to 625 amino acids, such as 625 to 640 amino acids.

In one particular embodiment, the fragment or variant of Hsp70 comprises all or part of the ATPase domain of Hsp70. It follows that the fragment or variant of Hsp70 according to the present invention in one embodiment comprises all or part of amino acids number 30 to 382.

In another particular embodiment, the fragment or variant of Hsp70 comprises tryptophan at amino acid position 90 of the Hsp70 ATPase domain.

A fragment of Hsp70 may be a truncated version of the wild type protein, meaning that it is a shorter version. A fragment may be truncated by shortening of the protein from either the amino-terminal or the carboxy-terminal ends of the protein, or it may be truncated by deletion of one or more internal regions of any size of the protein.

A fragment or variant of Hsp70 may in one embodiment have 100% homology to the wild-type protein. In another embodiment, the fragment or variant of Hsp70 may also be a variant of Hsp70 which has less than 100% homology to the wild-type protein, such as between 99.9 to 95% homology, for example 95 to 90% homology, such as 90 to 85% homology, for example 85 to 80% homology, such as 80 to 75% homology, for example 75 to 60% homology to the wild-type protein.

It is to be understood that any fragment or variant of Hsp70 which retains its ability to modulate lysosomal enzyme activity is encompassed by the present invention.

It is to be understood that any fragment or variant of Hsp70 which retains its ability to interact with BMP is encompassed by the present invention.

It is appreciated that the exact quantitative effect of the functional fragment or variant may be different from the effect of the full-length molecule. In some instances, the functional fragment or variant may indeed be more effective than the full-length molecule. Furthermore, the use of fragments instead of full-length molecules may be advantageous in view of the smaller size of the fragments.

In one embodiment, a functional fragment or variant of Hsp70 may be a variant of Hsp70 in which one or more amino acids has been substituted. Said substitution(s) may be an equivalent or conservative substitution(s), or a non-equivalent or non-conservative substitution(s).

In one embodiment, between 0.1 to 1% of the amino acid residues of wild type Hsp70 has been substituted, such as between 1 to 2% amino acid residues, for example between 2 to 3% amino acid residues, such as between 3 to 4% amino acid residues, for example between 4 to 5% amino acid residues, such as between 5 to 10% amino acid residues, for example between 10 to 15% amino acid residues, such as between 15 to 20% amino acid residues, for example between 20 to 30% amino acid residues, such as between 30 to 40% amino acid residues, for example between 40 to 50% amino acid residues, such as between 50 to 60% amino acid residues, for example between 60 to 70% amino acid residues, such as between 70 to 80% amino acid residues, for example between 80 to 90% amino acid residues, such as between 90 to 100% amino acid residues.

In one embodiment, between 1 to 5 of the amino acid residues of wild type Hsp70 has been substituted, such as between 5 to 10 amino acid residues, for example between 10 to 15 amino acid residues, such as between 15 to 20 amino acid residues, for example between 20 to 30 amino acid residues, such as between 30 to 40 amino acid residues, for example between 40 to 50 amino acid residues, such as between 50 to 75 amino acid residues, for example between 75 to 100 amino acid residues, such as between 100 to 150 amino acid residues, for example between 150 to 200 amino acid residues, such as between 200 to 300 amino acid residues, for example between 300 to 400 amino acid residues, such as between 400 to 500 amino acid residues.

In one embodiment, the functional fragment or variant of Hsp70 is a fusion protein. In one embodiment, said functional fragment or variant of Hsp70 is fused to a tag.

Advantages of Using Hsp70, or a Functional Fragment or Variant Thereof

As discussed herein above, there are no cures for the lysosomal storage diseases and treatment is mostly symptomatic, with the exception of the development of enzyme replacement therapies (ERT) for Gaucher disease and Fabry disease. As mentioned, ERT is a very expensive form of therapy that is effective for one specific disease only.

To the knowledge of the inventors, to date no succesful attempt has been made to provide ERT for the remaining lysosomal storage diseases associated with lipid accumulation, thus a major unmet need for an effective and specific treatment of these LSDs remains today.

Administration of Hsp70, or a functional fragment or variant thereof, to an individual in need thereof has a number of advantages compared to conventional treatment modalities for the lysosomal storage disorders.

First, producing a recombinant protein, such as rHsp70 or a functional fragment or variant thereof, is with modern technology a simple and straight-forward way of producing sufficient amounts of rHsp70, or a functional fragment or variant thereof. Conventional techniques for producing recombinant enzymes are well known to the skilled person.

Further, producing a recombinant protein, such as rHsp70 a functional fragment or variant thereof, is a cheap method for producing sufficient amounts of rHsp70, or a functional fragment or variant thereof. Compared to the production of enzymes for ERT, the cost is drastically reduced.

Also, the use of Hsp70, or a functional fragment or variant thereof can be used for treatment of more than one specific lysosomal storage disorder. This applies also to the Hsp70 inducers and co-inducers of the present invention. Indeed, the bioactive agent capable of increasing the intracellular concentration and/or activity of Hsp70 may be used for treatment of any lysosomal storage disease which may be reverted by modulating the enzymatic activity of the involved defective enzyme, wherein said enzyme interacts with BMP.

Finally, as Hsp70 is an endogenously occurring molecule, i.e. a molecule that originate from within an organism, tissue, or cell, it is to be expected that no or a very limited immune response is triggered by administering Hsp70, or a functional fragment or variant thereof. This is a major advantage as it facilitates treatment and reduces potential side effects when administered to an individual.

Ectopic Expression of Hsp70

In one embodiment, Hsp70, or a functional fragment or variant thereof, may be expressed from a vector. The invention thus in one embodiment relates to a vector encoding Hsp70, or a functional fragment or variant thereof.

In one embodiment of the present invention, Hsp70, or a functional fragment or variant thereof, may be administered to an individual in need thereof in the form of a vector.

The vector used for expressing Hsp70, or a functional fragment or variant thereof, may be selected from the group consisting of: viral vectors (retroviral and adenoviral) or non-viral vectors (plasmid, cosmid, bacteriophage).

In one embodiment, said vector comprises one or more of a origin of replication, a marker for selection and one or more recognition sites for a restriction endonuclease. In another embodiment, said vector is operably linked to regulatory sequences controlling the transcription of said Hsp70, or a functional fragment or variant thereof, in a suitable host cell.

The present invention in one embodiment relates to a method for producing Hsp70, or a functional fragment or variant thereof, as described herein; said method comprising the steps of providing a vector encoding said Hsp70, or a functional fragment or variant thereof, and expressing said vector either in vitro, or in vivo in a suitable host organism, thereby producing said Hsp70, or a functional fragment or variant thereof.

The invention further relates to an isolated recombinant or transgenic host cell comprising a vector encoding Hsp70, or a functional fragment or variant thereof, according to the present invention.

The invention also relates to a method for generating a recombinant or transgenic host cell, said method comprising the steps of providing a vector encoding Hsp70, or a functional fragment or variant thereof, introducing said vector into said recombinant or transgenic host cell and optionally also expressing said vector in said recombinant or transgenic host cell, thereby generating a recombinant or transgenic host cell producing said Hsp70, or a functional fragment or variant thereof.

In another embodiment the present invention relates to a transgenic, mammalian organism comprising the host cell described above.

In a further embodiment, the transgenic, mammalian organism comprising the recombinant or transgenic host cell according to the present invention is non-human.

The transgenic host cell may be selected from the group consisting of a mammalian, plant, bacterial, yeast or fungal host cell.

To improve the delivery of the DNA into the cell, the DNA must be protected from damage and its entry into the cell must be facilitated. Lipoplexes and polyplexes, have been created that have the ability to protect the DNA from undesirable degradation during the transfection process. Plasmid DNA can be covered with lipids in an organized structure like a micelle or a liposome. When the organized structure is complexed with DNA it is called a lipoplex. There are three types of lipids that may be employed for forming liposomes; anionic (negatively charged), neutral, or cationic (positively charged). Complexes of polymers with DNA are called polyplexes. Most polyplexes consist of cationic polymers and their production is regulated by ionic interactions.

In one embodiment, the vector comprising Hsp70, or a functional fragment or variant thereof, may be used for gene therapy. Gene therapy is the insertion of genes into an individual's cells and tissues to treat a disease, such as a hereditary disease in which a deleterious mutant allele is replaced with a functional one.

In another embodiment, Hsp70, or a functional fragment or variant thereof, may be administered as naked DNA. This is the simplest form of non-viral transfection. Delivery of naked DNA may be performed by use of electroporation, sonoporation, or the use of a "gene gun", which shoots DNA coated gold particles into a cell using high pressure gas.

Bioactive Agent—Hsp70 Inducers and Co-Inducers

The present invention relates in one embodiment to the modulation of enzymatic activity, wherein said enzyme interacts with BMP, by the use of Hsp70 inducers or co-inducers.

A Hsp70 inducer is a compound that can by itself amplify Hsp70 gene expression and protein expression without a concomitant stress.

A Hsp70 co-inducer is a compound that cannot amplify Hsp70 gene expression and protein expression without a concomitant (mild) stress, but the stress-induced increase in Hsp70 levels is further elevated or enhanced by their presence.

It is an aspect of the present invention to provide an Hsp70 inducer or co-inducer for use as a medicament.

It is a further aspect of the present invention to provide an Hsp70 inducer or co-inducer for use in treating lysosomal storage disorders.

It is a still further aspect of the present invention to provide the use of an Hsp70 inducer or co-inducer, for the manufacture of a medicament for treating lysosomal storage disorders.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

In a particular embodiment, said lysosomal storage disorder is Niemann-Pick disease type A or B. In another particular embodiment, said lysosomal storage disorder is Farber disease. In another particular embodiment, said lysosomal storage disorder is Krabbe disease. In another particular embodiment, said lysosomal storage disorder is Metachromatic leukodystrophy. In another particular embodiment, said lysosomal storage disorder is Sialidosis. In another particular embodiment, said lysosomal storage disorder is Fabry disease. In yet another particular embodiment, said lysosomal storage disorder is Gaucher disease. In yet another particular embodiment, said lysosomal storage disorder is saposin-deficiency.

In one embodiment, the bioactive agent according to the present invention is an Hsp70 inducer or co-inducer. In a particular embodiment, the bioactive agent according to the present invention is an Hsp70 inducer. In another particular embodiment, the bioactive agent according to the present invention is an Hsp70 co-inducer.

Small-Molecule Drugs—Hydroxylamine Derivatives

In one embodiment, the bioactive agent according to the present invention is a Hsp70 co-inducer. In a further embodiment, said Hsp70 co-inducer is a small-molecule drug.

In a particular embodiment, the Hsp70 co-inducer according to the present invention is a hydroxylamine derivative.

Said hydroxylamine derivative may in a further embodiment selected from the group of Bimoclomol (BRLP-42), Arimoclomol (BRX-220), BRX-345 and BGP-15.

In a particular embodiment, said hydroxylamine derivative is Arimoclomol (BRX-220).

Bimoclomol ([2-hydroxy-3-(1-piperidinyl) propoxy]-3-pyridine-carboximidoyl-chloride maleate) is a non-toxic compound that was originally developed for treatment of diabetic complications such as neuropathies. Bimoclomol has been shown to improve cell survival under experimental stress conditions partly by increasing intracellular heat shock proteins (HSPs), including Hsp70, via an activation of HSF-1. It has been shown that bimoclomol possess the capability of Hsp70 co-induction in the absence of unfolded proteins, and that bimoclomol interacts with and increases the fluidity of negatively charged membrane lipids. BRX-345 is a structural analog of bimoclomol with a somewhat lesser ability to induce HSPs.

Arimoclomol (BRX-220) is an analog of bimoclomol, which also interacts with and amplifies the heat shock response. Arimoclomol is currently in clinical trials for the treatment of ALS (amyotrophic lateral sclerosis); a progressive neurodegenerative disorder. Arimoclomol is owned by CytRx Corporation.

It is thus an aspect of the present invention to provide a hydroxylamine derivative Hsp70 co-inducer for use in treating lysosomal storage disorders.

It is a still further aspect of the present invention to provide the use of a hydroxylamine derivative Hsp70 co-inducer for the manufacture of a medicament for treating lysosomal storage disorders.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

Membrane Fluidizers

In one embodiment, the bioactive agent according to the present invention is a Hsp70 inducer. In a further embodiment, said Hsp70 inducer is a membrane fluidizer.

Treatment with a membrane fluidizer may also be termed lipid therapy.

In a particular embodiment, the Hsp70 inducer according to the present invention is a membrane fluidizer selected from the group of benzyl alcohol, heptanol, AL721, Docosahexaenoic acid, aliphatic alcohols, oleyl alcohol, dimethylaminoethanol, $A_2C$, farnesol and anaesthetics such as lidocaine, ropivacaine, bupivacaine and mepivacaine, as well as others known to the skilled person.

Besides the denaturation of a proportion of cellular proteins during heat (proteotoxicity), a change in the fluidity of membranes is also proposed as being a cellular thermosensor that initiates the heat shock response and induces HSPs. Indeed, chemically induced membrane perturbations—analogous with heat induced plasma membrane fluidization—are capable of activating HSP, without causing protein denaturation.

Membrane fluidity refers to the viscosity of the lipid bilayer of a cell membrane. The membrane phospholipids incorporate fatty acids of varying length and saturation.

The membrane fluidizers act by intercalating between membrane lipids thus inducing a disordering effect by weakening of van der Vaals interactions between the lipid acyl chains.

It is thus an aspect of the present invention to provide a membrane fluidizer selected from the group of benzyl alcohol, heptanol, AL721, Docosahexaenoic acid, aliphatic alcohols, oleyl alcohol, dimethylaminoethanol, $A_2C$, farnesol and anaesthetics such as lidocaine, ropivacaine, bupivacaine and mepivacaine, as well as others known to the skilled person, for use in treating lysosomal storage disorders.

It is a still further aspect of the present invention to provide the use of a membrane fluidizer selected from the group of benzyl alcohol, heptanol, AL721, Docosahexaenoic acid, aliphatic alcohols, oleyl alcohol, dimethylaminoethanol, $A_2C$, farnesol and anaesthetics such as lidocaine, ropivacaine, bupivacaine and mepivacaine, as well as others known to the skilled person, for the manufacture of a medicament for treating lysosomal storage disorders.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

Other Means for Inducing Hsp70

Any means for inducing Hsp70 expression is envisioned to be encompassed by the present invention, some of which are outlined herein below.

Increasing the temperature of an individual is a potent inducer of HSPs including Hsp70, and as such sub-lethal heat therapy is an aspect of the present invention. In one embodiment, sub-lethal heat therapy comprises increasing the temperature of an individual to a core temperature of about 38° C., such as about 39° C., for example about 40° C., such as about 41° C., for example about 42° C., such as about 43° C.

It is thus an aspect of the present invention to provide sub-lethal heat therapy for use in treating lysosomal storage disorders.

Psychological stress such as predatory fear and electric shock can evoke a stress induced eHsp70 release, a process which is suggested to be dependent on cathecholamine signaling. Further, adrenaline and noradrenalin can evoke Hsp70 release.

The following compounds have been shown to induce (or co-induce) HSPs, including Hsp70: the membrane-interactive compound alkyllysophospholipid Edelfosine (ET-18-OCH3 or 1-octadecyl-2-methyl-rac-glycero-3-phosphocholine); anti-inflammatory drugs including cyclooxygenase ½ inhibitors such as celecoxib and rofecoxib, as well as NSAIDs suh as acetyl-salicylic acid, sodium salicylate and indomethacin; prodstaglandins PGA1, PGj2 and 2-cyclopentene-1-one; peroxidase proliferator-activated receptor-gamma agonists; tubulin-interacting anticancer agents including vincristine and paclitaxel; the insulin sensitizer pioglitazone; anti-neoplastic agents such as carboplatin, doxorubicin, fludarabine, ifosfamide and cytarabine; the Hsp90 inhibitors geldanamycin, 17-AAG, 17-DMAG, radicicol, herbimycin-A and arachidonic acid; proteasome inhibitors MG132 and lactacystin; serine protease inhibitors DCIC, TLCK and TPCK; the anti-ulcer drugs geranylgeranylacetone (GGA), rebamipide, carbenoxolone and polaprezinc (zinc L-carnosine); heavy metals (zinc and tin); the anti-inflammatory drug dexamethasone; cocaine; nicotine; alcohol; alpha-adrenergic agonists; cyclopentenone prostanoids; as well as herbal medicines paeoniflorin, glycyrrhizin, celastrol, dihydrocelastrol, dihydrocelastrol diacetate and curcumin.

It is thus an aspect of the present invention to provide a compound selected from the group of Edelfosine (ET-18-OCH3 or 1-octadecyl-2-methyl-rac-glycero-3-phosphocholine), celecoxib, rofecoxib, acetyl-salicylic acid, sodium salicylate, indomethacin, PGA1, PGj2 2-cyclopentene-1-one, peroxidase proliferator-activated receptor-gamma agonists, vincristine, paclitaxel, pioglitazone, carboplatin, doxorubicin, fludarabine, ifosfamide cytarabine, geldanamycin, 17-RAG, 17-DMAG, radicicol, herbimycin-A, arachidonic acid, MG132, lactacystin, DCIC, TLCK, TPCK, geranylgeranylacetone (GGA), rebamipide, carbenoxolone, polaprezinc (zinc L-carnosine), dexamethasone, cocaine, nicotine, alcohol, alpha-adrenergic agonists, cyclopentenone prostanoids, paeoniflorin, glycyrrhizin, celastrol, dihydrocelastrol, dihydrocelastrol diacetate and curcumin, as well as other HSP inducers known to the skilled person, for use in treating lysosomal storage disorders.

Pharmaceutical Composition According to the Present Invention

The present invention relates to the modulation of enzymatic activity, wherein said enzyme interacts with BMP, by use of a bioactive agent capable of increasing the concentration and/or activity of Hsp70, thereby benefiting patients suffering from lysosomal storage diseases.

Whilst it is possible for the bioactive agents of the present invention to be administered as the raw chemical, it is preferred to present them in the form of a pharmaceutical formulation. Accordingly, the present invention further provides a pharmaceutical composition, for medicinal application, which comprises a bioactive agent of the present invention or pharmaceutically acceptable salts thereof, as herein defined, and a pharmaceutically acceptable carrier therefore.

It is an aspect of the present invention to provide a composition, such as a pharmaceutical composition, comprising a bioactive agent identified herein that may be administered to an individual in need thereof.

In one embodiment, the invention relates to a composition comprising a bioactive agent according to the present invention. The composition as disclosed herein may in one embodiment be formulated in combination with a physiologically acceptable carrier. The composition as disclosed herein may in one embodiment be formulated in combination with a pharmaceutically acceptable carrier.

Pharmaceutical compositions containing a bioactive agent of the present invention may be prepared by conventional techniques, e.g. as described in Remington: The Science and Practice of Pharmacy 1995, edited by E. W. Martin, Mack Publishing Company, 19th edition, Easton, Pa.

The bioactive agents of the present invention may be formulated for parenteral administration and may be presented in unit dose form in ampoules, pre-filled syringes, small volume infusion or in multi-dose containers with an added preservative. The compositions may take such forms as suspensions, solutions, or emulsions in oily or aqueous vehicles, carriers, diluents, or solvents including aqueous solutions of mineral salts or other water-soluble molecules, propylene glycol, polyethylene glycol, vegetable oils, animal oils, synthetic oils, injectable organic esters, and may contain formulatory agents such as preserving, wetting, emulsifying or suspending, stabilizing and/or dispersing agents, colorants, buffers, thickeners, solubilizing agents and the like. Alternatively, the active ingredient may be in powder form, obtained by aseptic isolation of sterile solid or by lyophilization from solution for constitution before use with a suitable vehicle, e.g., sterile, pyrogen-free water.

Pharmaceutically acceptable salts of the bioactive agents, where they can be prepared, are also intended to be covered by this invention, as are specific hydrate forms of a salt. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

Any suitable formulation of the bioactive agent according to the present invention may be employed, known to the skilled person.

In one embodiment, the Hsp70, or a functional fragment or variant thereof, is formulated in a biodegradable microsphere, such as a liposome.

Administration

Any suitable route of administration may be employed for providing a mammal, preferably a human, with an effective amount of a bioactive agent according to the present invention, wherein said bioactive agent may be Hsp70, or a functional fragment or variant thereof.

Administering bioactive agents or pharmaceutical compositions to an individual in need thereof may occur via three major routes of delivery: 1) Topical (applied to body surfaces such as skin or mucous membranes), 2) Enteral (via the gastrointestinal or digestive tract) and 3) Parenteral (routes other than the gastrointestinal or digestive tract).

Topical administration includes epicutaneous (application onto the skin), inhalational, enema, eye drops (onto the conjunctiva), ear drops, intranasal route, and vaginal administration.

Enteral administration is any form of administration that involves any part of the gastrointestinal tract and includes oral administration (by mouth e.g. tablets, capsules or drops), intrarectal (e.g. suppository or enema) administration besides by gastric or duodenal feeding tube.

Parenteral delivery, such as by injection or infusion, are effective to deliver the bioactive agent to a target site or to introduce the drug into the bloodstream, and includes intravenous (into a vein), intra-arterial (into an artery), intramuscular (into a muscle), intracardiac (into the heart), subcutaneous (under the skin), intraosseous (into the bone marrow), intradermal, (into the skin itself), intrathecal or intraspinal (into the spinal canal), intraperitoneal, (into the peritoneum), transdermal (diffusion through the intact skin), transmucosal (diffusion through a mucous membrane, e.g. insufflation (snorting), sublingual, buccal and vaginal suppositories), inhalational, epidural (into the epidural space) and intravitreal (into the eye). Sublingual administration (under the tongue) is also a form of parenteral administration, whereby bioactive agents diffuse into the bloodstream through the mucosal tissue under the tongue. The bioactive agent of the present invention may be administered by any parenteral route of delivery and preferably any of the above.

Parenteral delivery has the advantage of avoiding degradation in the gastrointestinal tract, as associated with enteral delivery.

Parenteral delivery has the further advantage of of abolishing first pass metabolism, as associated with enteral delivery, because it allows compounds to be absorbed directly into the systemic circulation.

First-pass metabolism is a phenomenon of drug metabolism whereby the concentration of a drug is greatly reduced before it reaches the systemic circulation. It is the fraction of lost drug during the process of absorption which is generally related to the liver and gut wall.

After a drug is swallowed, it is absorbed by the digestive system and enters the hepatic portal system. It is carried through the portal vein into the liver before it reaches the rest of the body. The liver metabolizes many drugs, sometimes to such an extent that only a small amount of active drug emerges from the liver to the rest of the circulatory system. This first pass through the liver thus greatly reduces the bioavailability of the drug.

The four primary systems that affect the first pass effect of a drug are the enzymes of the gastrointestinal lumen, gut wall enzymes, bacterial enzymes, and hepatic enzymes.

Appropriate dosage forms for such administration may be prepared by conventional techniques. Appropriate dosage forms for administration by inhalation, such as an aerosol formulation or a metered dose inhaler, may be prepared by conventional techniques.

In one embodiment, a particular mode of administration of a bioactive agent according to the present invention is by parenteral administration.

In one embodiment, a particular mode of parenteral administration of a bioactive agent of the present invention is by intravenous, subcutaneous, intramuscular, intraarterial, subcutaneous or intraperitoneal injection.

In one embodiment, a particular mode of parenteral administration of a bioactive agent of the present invention is by inhalation.

In one embodiment, a particular mode of parenteral administration of a bioactive agent of the present invention is by intravenous infusion.

Intravenous infusion according to the present invention may in one embodiment occur over a time period of from 10 minutes to 20 minutes, such as 20 to 30 minutes, for example 30 to 40 minutes, such as 40 to 50 minutes, for example 50 to 60 minutes, such as 60 to 90 minutes, for example 90 to 120 minutes, such as 2 hours to 3 hours, for example 3 to 4 hours, such as 4 to 5 hours, for example 5 to 6 hours, such as 6 to 7 hours, for example 7 to 8 hours.

In a particular embodiment, the mode of parenteral administration of a bioactive agent of the present invention is by transmucosal delivery. Said transmucosal delivery is in one embodiment sublingual delivery, in another embodiment said transmucosal delivery is buccal delivery, and in yet another embodiment said transmucosal delivery is insufflation or intranasal delivery.

Dosage forms include tablets, troches, dispersions, suspensions, solutions, capsules, creams, ointments, emulsions, gels, lotions, pastes, aerosols, or other forms known in the art.

The effective dosage of active ingredient employed may vary depending on the particular composition employed, the mode of administration, the condition being treated and the severity of the condition being treated. Such dosage may be ascertained readily by a person skilled in the art.

In one embodiment, the bioactive agent of the present invention is administered at a daily dosage of from about 1 microgram to about 100 milligram per kilogram of animal body weight, given as a single daily dose or in divided doses, or in sustained release form. The dosage regimen may be adjusted within this range or even outside of this range to provide the optimal therapeutic response.

In one embodiment, the bioactive agent of the present invention is administered at a dosage of from about 1 µg to about 10 µg per kg body weight, such as from about 10 µg to about 50 µg per kg body weight, for example from about 50 µg to about 100 µg per kg body weight, such as from about 100 µg to about 250 µg per kg body weight, for example from about 250 µg to about 500 µg per kg body weight, such as from about 500 µg to about 750 µg per kg body weight, for example from about 750 µg to about 1000 µg per kg body weight, such as from about 1 mg to about 10 mg per kg body weight, for example from about 10 mg to about 50 mg per kg body weight, such as from about 50 mg to about 100 mg per kg body weight.

Said dosage may be administered in certain time intervals, and may be expressed as mg per kg body weight per time unit. Said time unit may in one embodiment be per minute, such as per hour, for example per day, such as per week.

Combination Treatment

It is an aspect of the present invention to provide a bioactive agent capable of increasing the intracellular concentration and/or activity of Hsp70 for use in treatment of lysosomal storage disorders, in combination with other treatment modalities.

The present invention in one aspect relates to a method of treatment of a lysosomal storage disease comprising administration of the bioactive agent according to any the present invention in combination with at least one other treatment modality.

Thus, in one embodiment, the bioactive agent according to the present invention is administered to an individual in need thereof in combination with at least one other treatment modality, such as conventional or known treatment modalities for LSDs.

It is understood, that the bioactive agent according to the present invention is Hsp70 or a functional fragment or variant thereof, or an Hsp70 inducer or co-inducer.

Administering more than one treatment modality in combination may occur either simultaneously, or sequentially. Simultaneous administration may be two compounds comprised in the same composition or comprised in separate compositions, or may be one composition and one other treatment modality performed essentially at the same time. Sequential administration means that the more than one treatment modalities are administered at different time points, such as administering one treatment modality first, and administering the second treatment modality subsequently. The time frame for administering more than one treatment modality sequentially may be determined by a skilled person in the art for achieving the optimal effect, and may in one embodiment be between 30 minutes to 72 hours.

The treatment modalities in the form of chemical compounds may be administered together or separately, each at its most effective dosage. Administering more than one compound may have a synergistic effect, thus effectively reducing the required dosage of each drug.

In one embodiment, the bioactive agent according to the present invention is administered to an individual in need thereof in combination with enzyme replacement therapy (ERT). Said ERT may in one embodiment be selected from the group consisting of Cerezyme® (imiglucerase for injection), Miglustat, Fabrazyme® (agalsidase beta), and Replagal (Agalsidase alpha).

In one embodiment, the bioactive agent according to the present invention is administered to an individual with Gaucher disease in combination with Cerezyme® (imiglucerase for injection) or Miglustat.

In another embodiment, the bioactive agent according to the present invention is administered to an individual with Fabry disease in combination with Fabrazyme® (agalsidase beta) or Replagal (Agalsidase alpha).

In another embodiment, the bioactive agent according to the present invention is administered to an individual in need thereof in combination with pain relievers.

In yet another embodiment, the bioactive agent according to the present invention is administered to an individual in need thereof in combination with corticosteroids.

The bioactive agent according to the present invention may in one embodiment be administered to an individual in need thereof in combination with a transplantation, such as bone marrow transplantation, cord blood transplantation or stem cell transplantation.

The bioactive agent according to the present invention may in another embodiment be administered to an individual in need thereof in combination with substrate reduction therapy.

In another embodiment, the bioactive agent according to the present invention is administered to an individual in need thereof in combination with symptomatic and supportive therapy, such as physical therapy.

Hsp70 Increases the Uptake of Compounds

Figure 16:
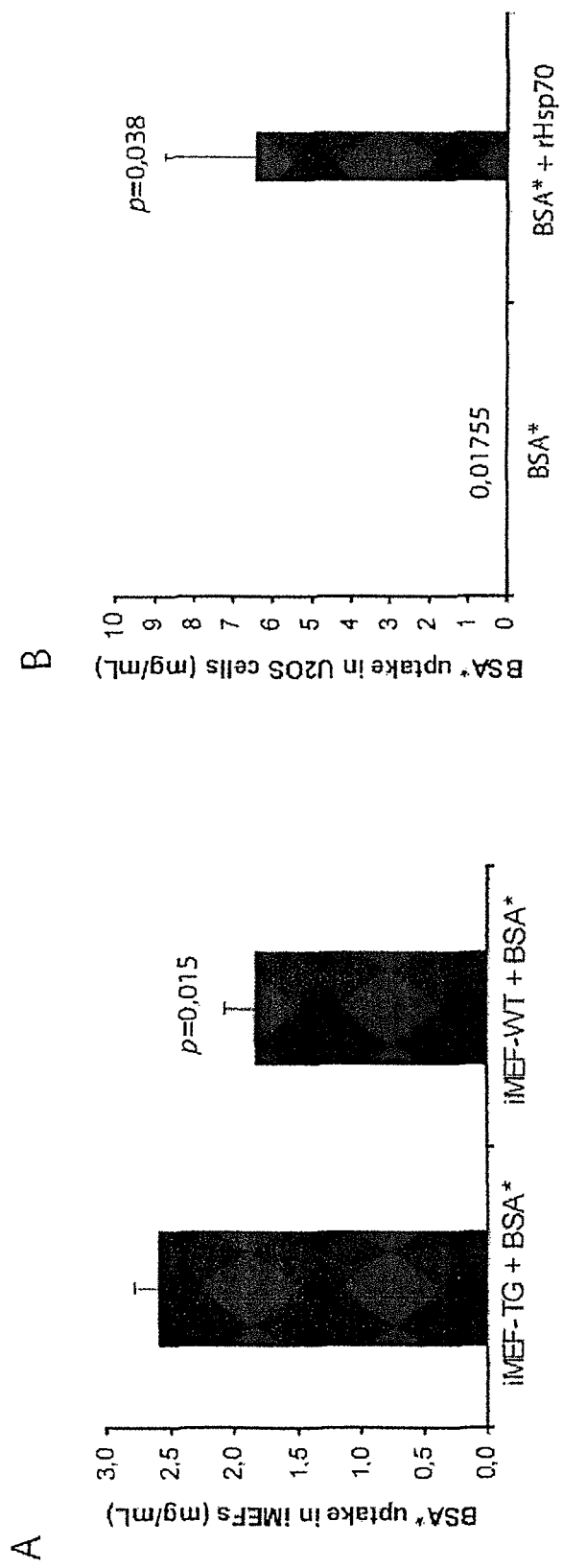

The present inventors have further shown that Hsp70 increases the endocytic uptake of other molecules (FIG. 16). This increased uptake may occur independently on Hsp70 due to a passive mechanism which allows a compound to be more readily taken up by the cell in the presence of Hsp70, or it may be occur dependently on Hsp70 due to a direct association with Hsp70.

The ability of Hsp70 to increase the cellular uptake of compounds is an advantage in that it allows for Hsp70, or a functional fragment or variant thereof, administered to cells to be readily taken up by the cell.

Further, the ability of Hsp70 to increase the cellular uptake of compounds is an advantage in combination treatment regimens, as the presence of Hsp70 may incresase the uptake of both Hsp70 and the compound given in combination with Hsp70.

In respect to combination therapy wherein one compound is an enzyme for ERT, and the other is Hsp70, or a functional fragment or variant thereof, this may help effectively reduce the amount of enzyme for ERT needed to achieve an effective intracellular dosis. This is relevant as ERT is very expensive.

In the situation in which the bioactive agent according to the present invention comprises a combination of Hsp70, or a functional fragment or variant thereof, and an Hsp70 inducer or co-inducer, the presence of Hsp70 may therefore increase the uptake of said Hsp70 inducer or co-inducer.

Method for Modulating the Enzymatic Activity of an Enzyme

The present invention relates in one aspect to the modulation of enzymatic aciticty. Said enzyme may be an enzyme involved in the catabolism of lysosomal substances. And said modulation may derive from an interaction between Hsp70 and BMP.

The present inventors have thus described an interaction between Hsp70 and BMP, wherein Hsp70 interacts with or binds to BMP with a certain affinity. By a molecule having an "affinity" for molecule X is meant herein that a molecule with affinity for molecule X will bind to molecule X in a certain detectable amount under certain conditions but will not (optionally detectably) bind other, different molecules (for which it does not have affinity for) to the same extent under identical conditions. One measure to describe a molecule's affinity to another molecule is a dissociation constant, Kd. The smaller the Kd, the stronger the affinity. Dissociation constants can be determined using methods well-known in the art, such as surface plasmon resonance analysis. Herein, it is preferred that a molecule with "affinity" for another molecule X has a Kd for said molecule X that is less than 100 mM, such as less than 10 mM, for example less than 5 mM, such as less than 1 mM, for example less than 0.1 mM, such as less than 0.01 mM, for example less than 1 µM, such as less than 100 nM, for example less than 10 nM, such as less than 1 nM, for example less than 100 µM, such as less than 10 pM, for example less than 1 pM. Furthermore, it is herein preferred that a molecule that "does not have an affinity" to molecule X has a dissociation constant, Kd with respect to binding molecule X that is at least 10 fold larger, such as at least 20 fold larger, for example at least 30 fold larger, such as at least 40 fold larger, for example at least 50 fold larger, such as at least 60 fold larger, for example at least 70 fold larger, such as at least 80 fold larger, for example at least 90 fold larger, such as at least 100 fold larger, than the Kd of the binding (to molecule X) of a molecule that does have affinity to molecule X. Most preferably, there is at least a ten-fold difference in Kd between those molecules considered to have an affinity and those deemed not to have an affinity to a molecule X.

It is an aspect of the present invention to provide a method for modulating the enzymatic activity of an enzyme, wherein said enzyme interacts with BMP (bis(monoacyl-glycero)phosphate), said method comprising the steps of
  i) administering a bioactive agent capable of increasing the intracellular concentration and/or activity of Hsp70, and
  ii) allowing interaction between BMP and Hsp70, and
  iii) modulating the enzymatic activity of an enzyme interacting with BMP.

Said interaction may in one embodiment be direct, or said interaction may in another embodiment be indirect.

In one embodiment, the present invention relates to a method for modulating the enzymatic activity of an enzyme, wherein said enzyme interacts with BMP (bis(monoacyl-glycero)phosphate), said method comprising the steps of
  i) administering the bioactive agent according to the present invention,
  ii) allowing interaction between BMP and Hsp70, and
  iii) modulating the enzymatic activity of an enzyme interacting with BMP.

In one embodiment, said Hsp70 forms a covalent or non-covalent complex with BMP.

In one embodiment, said BMP interacts with a saposin. In a further embodiment, said saposin may be selected from the group consisting of saposin A, saposin B, saposin C, and saposin D.

In a further embodiment, said enzyme is selected from the group consisting of sphingomyelinase, acidic sphingomyelinase (aSMase), acid ceremidase, beta-galactosylceremidase, alpha-galactosidase, beta-galactosidase, glucosylceremidase, sialidase and aryl sulfatase.

In one particular embodiment, the modulation of the enzymatic activity is an increase in the enzymatic activity.

In one embodiment, said increase in the enzymatic activity is an increase in the range of 1 to 5%, such as in the range of 5 to 10%, for example in the range of 10 to 15%, such as in the range of 15 to 20%, for example in the range of 20 to 25%, such as in the range of 25 to 30%, for example in the range of 30 to 35%, such as in the range of 35 to 40%, for example in the range of 40 to 45%, such as in the range of 45 to 50%, for example in the range of 50 to 60%, such as in the range of 60 to 70%, for example in the range of 70 to 80%, such as in the range of 80 to 90%, for example in the range of 90 to 100%, such as in the range of 100 to 120%, for example in the range of 120 to 140%, such as in the range of 140 to 160%, for example in the range of 160 to 180%, such as in the range of 180 to 200%, for example in the range of 200 to 250%, such as in the range of 250 to 300%, for example in the range of 300 to 400%, such as in the range of 400 to 500%, for example in the range of 500 to 750%, such as in the range of 750 to 1000%, for example in the range of 1000 to 1500%, such as in the range of 1500 to 2000%, for example in the range of 2000 to 5000%.

The present invention in another aspect relates to a method for identifying binding partners for the Hsp70-BMP complex, said method comprising the steps of extracting said Hsp70-BMP complex and isolating said binding partners. In one embodiment, said binding artner is an agonist. In another embodiment, said binding partner is an antagonist.

The present invention in another aspect relates to a Hsp70-BMP complex, and its use for a medicament, such as for the treatment of a lysosomal storage disease.

In one embodiment, the present invention relates to an antibody that specifically recognizes the Hsp70-BMP complex.

Method of Treatment

The present invention relates in one aspect to a method for treating an individual in need thereof.

It is thus an aspect of the present invention to provide a method for treatment of a lysosomal storage disease comprising administration of the bioactive agent according to the present invention to an individual in need thereof.

It follows, that in one embodiment said treatment may be prophylactic, curative or ameliorating. In one particular embodiment, said treatment is prophylactic. In another embodiment, said treatment is curative. In a further embodiment, said treatment is ameliorating.

The bioactive agent used according to the present invention may in one embodiment be formulated as a pharmaceutical composition.

In one embodiment, said lysosomal storage disorder is selected from the group consisting of Niemann-Pick disease, Farber disease, Krabbe disease, Fabry disease, Gaucher disease, Metachromatic leukodystrophy, Sialidosis and saposin-deficiency.

In a particular embodiment, said lysosomal storage disorder is Niemann-Pick disease type A or B. In another particular embodiment, said lysosomal storage disorder is Farber disease. In another particular embodiment, said lysosomal storage disorder is Krabbe disease. In another particular embodiment, said lysosomal storage disorder is Metachromatic leukodystrophy. In another particular embodiment, said lysosomal storage disorder is Sialidosis. In another particular embodiment, said lysosomal storage disorder is Fabry disease. In yet another particular embodiment, said lysosomal storage disorder is Gaucher disease. In yet another particular embodiment, said lysosomal storage disorder is saposin-deficiency.

In one embodiment, said lysosomal disease is characterized by an increased intracellular accumulation of a sphingolipid.

In one embodiment, said treatment reduces the intracellular accumulation of substances in an individual in need thereof. Said substance may be a substance which is normally degraded in the lysosomes. In one embodiment, said substance is a shingolipid.

In one embodiment, the treatment according to the present invention reduces the intracellular accumulation of a lysosomally degradable substance such as a sphingolipid to less than 100% of the accumulated amount, such than less than 90% of the accumulated amount, for example less than 80% of the accumulated amount, such than less than 70% of the accumulated amount, for example less than 60% of the accumulated amount, such than less than 50% of the accumulated amount, for example less than 40% of the accumulated amount, such than less than 30% of the accumulated amount, for example less than 20% of the accumulated amount, such than less than 10% of the accumulated amount, for example less than 5% of the accumulated amount.

In one embodiment, the treatment according to the present invention reduces the intracellular accumulation of a sphingolipid by at least 5%, such as at least 10%, for example at least 15%, such as at least 20%, for example at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80%, for example at least 85%, such as at least 90%, for example at least 95%, such as at least 100%.

In one embodiment, said accumulated sphingolipid is selected from the group consisting of sphingomyelin, ceramide, galactosylceramide, globotriaosylceramide, glycosylceramide, GM3 and sulfatide.

The rate of reducing the intracellular concentration of a lysosomaly degradable substance such as a sphingolipid may depend on factors such as administration form, dosage regimens and the like.

In one embodiment, said treatment prolongs the life expectancy of said individual in need thereof.

It follows, that the life expectancy may in one embodiment be increased by between 6 months to 1 year, such as from 1 year to 2 years, for example from 2 to 3 years, such as from 3 to 4 years, for example from 4 to 5 years, such as from 5 to 6 years, for example from 6 to 7 years, such as from 7 to 8 years, for example from 8 to 9 years, such as from 9 to 10 years, for example from 10 to 12 years, such as from 12 to 14 years, for example from 14 to 16 years, such as from 16 to 18 years, for example from 18 to 20 years, such as from 20 to 25 years, for example from 25 to 30 years, such as from 30 to 40 years, for example from 40 to 50 years, such as from 50 to 60 years, for example from 60 to 70 years, such as from 70 to 80 years, for example from 80 to 90 years, as from 90 to 100 years.

In one embodiment life expectancy is increased by at least 6 months, such as at least 1 year, such as at least 2 years, for example 3 years, such as at least 4 years, for example 5 years, such as at least 6 years, for example 7 years, such as at least 8 years, for example 9 years, such as at least 10 years, for example 12 years, such as at least 14 years, for example 16 years, such as at least 18 years, for example 20 years, such as at least 25 years, for example 30 years, such as at least 40 years, for example 50 years, such as at least 60 years, for example 70 years, such as at least 80 years, for example 90 years, such as at least 100 years.

It is also an aspect of the present invention to provide a method for prolonging life expectancy in a patient with a lysosomal storage disease, wherein said method comprises administration of the bioactive agent according to the present invention to an individual in need thereof.

In one embodiment, the present invention relates to a method for prolonging life expectancy in a patient with a lysosomal storage disease, wherein said method comprises administration of the bioactive agent according to the present invention to an individual in need thereof, wherein said life expectancy is increased by between 6 months to 1 year, such as from 1 year to 2 years, for example from 2 to 3 years, such as from 3 to 4 years, for example from 4 to 5 years, such as from 5 to 6 years, for example from 6 to 7 years, such as from 7 to 8 years, for example from 8 to 9 years, such as from 9 to 10 years, for example from 10 to 12 years, such as from 12 to 14 years, for example from 14 to 16 years, such as from 16 to 18 years, for example from 18 to 20 years, such as from 20 to 25 years, for example from 25 to 30 years, such as from 30 to 40 years, for example from 40 to 50 years, such as from 50 to 60 years, for example from 60 to 70 years, such as from 70 to 80 years, for example from 80 to 90 years, such as from 90 to 100 years.

In one embodiment, the present invention relates to a method for prolonging life expectancy in a patient with a lysosomal storage disease, wherein said method comprises administration of the bioactive agent according to the present invention to an individual in need thereof, wherein said life expectancy is increased by at least 6 months, such as at least 1 year, such as at least 2 years, for example 3 years, such as at least 4 years, for example 5 years, such as at least 6 years, for example 7 years, such as at least 8 years, for example 9 years, such as at least 10 years, for example 12 years, such as at least 14 years, for example 16 years, such as at least 18 years, for example 20 years, such as at least 25 years, for example 30 years, such as at least 40 years, for example 50 years, such as at least 60 years, for example 70 years, such as at least 80 years, for example 90 years, such as at least 100 years.

EXAMPLES

Example 1

Interaction Between Hsp70 and Bis(Monoacylglycero)Phosphate Stabilizes Lysosomes and Promotes Cell Survival Abstract Lysosomal membrane permeabilization is an evolutionarily conserved hallmark of stress-induced cell death. Here the inventors show that the major stress-inducible heat shock protein 70 (Hsp70) enhances cell survival by stabilizing lysosomes through a pH-dependent high affinity binding to an endo-lysosomal anionic phospholipid bis(monoacylglycero)phosphate (BMP; also referred to as lysobisphosphatidic acid). The positively charged ATPase domain of Hsp70 is responsible for the binding but the substrate-binding domain is also required for effective stabilization of lysosomes. Importantly, the cytoprotective effect can be obtained by endocytic delivery of recombinant Hsp70 and specifically reverted by extra cellular administration of BMP antibodies or Hsp70 inhibitors. Thus, this protein-lipid interaction opens exciting possibilities for the development of cytoprotective and cytotoxic lysosome-specific therapies for the treatment of degenerative diseases and cancer, respectively.

Introduction

Lysosomes are highly dynamic cytosolic organelles that receive membrane traffic input from the biosynthetic (trans-Golgi network), endocytic, phagocytic and autophagic pathways. They contain over 50 acid hydrolases that can process all the major macromolecules of the cell to breakdown products available for metabolic reutilization. In addition to their catabolic house keeping functions, lysosomal proteases, cathepsins, have recently been identified as important effectors in evolutionarily conserved cell death programs induced for example by death receptors of tumor necrosis factor receptor family, hypoxia, oxidative stress, osmotic stress, heat and anti-cancer drugs. Cathepsin-dependent cell death is characterized by an early lysosomal membrane permeabilization and the subsequent translocation of cathepsins into the cytosol, where they can initiate both caspase-dependent and—independent cell death pathways. Thus, the lysosomal membrane integrity emerges as an important regulator of cell survival during various stress conditions.

Whereas cytosolic cysteine protease inhibitors have been reported to confer protection against cathepsin-induced cellular damage both in mammalian cells as well as in nematode Caenorhabditis elegans, the mechanisms by which cells regulate lysosomal membrane stability have remained largely obscure. Recent indirect evidence suggests, however, that the potent cytoprotective effect of the major stress-inducible Hsp70 is due to lysosomal membrane stabilization. The depletion of Hsp70 triggers an early permeabilization of lysosomal membranes and cathepsin-mediated cell death in cancer cells, and exogenous Hsp70 effectively inhibits lysosomal destabilization induced by various stresses. Furthermore, mice deficient for Hsp70 suffer from pancreatitis caused by the leakage of lysosomal proteases into the cytosol.

The molecular mechanism underlying the lysosome protective potential of Hsp70 has remained elusive, but clues to its mechanism of action may lie in the stress- and cancer-associated translocation of a small portion of Hsp70 to the endo-lysososmal compartment. The major aim of this study was to define whether the lysosomal localization, indeed, is crucial for the cytoprotective effect of Hsp70. Remarkably, the data presented herein demonstrate that Hsp70 binds with high affinity to a lysosome-specific lipid BMP and that this protein-lipid interaction stabilizes lysosomes. Importantly this novel cytoprotective mechanism can be exploited by extracellular administration of either cytoprotective Hsp70 itself or compounds that interfere with Hsp70-BMP binding or Hsp70 function specifically in the lysosomal compartment.

Results and Discussion

In order to test whether the lysosomal localization is crucial for the cytoprotective effect of Hsp70, the present inventors produced recombinant Hsp70 (rHsp70) and took advantage of the endocytic machinery of cells to target rHsp70 into the lysosomal lumen. Immunocytochemical analysis of U-2-OS osteosarcoma cells incubated with Alexa Fluor 488-labeled rHsp70 revealed a clear co-localization of the endocytosed rHsp70 with late endosomal and lysosomal marker proteins (lysosome-associated membrane proteins 1 and 2 and lysosomal integral membrane protein-1 (LIMP-1)) and an endo-lysosome-specific lipid (BMP), whereas no co-localization was seen with markers for the endoplasmatic reticulum (endoplasmatic reticulum $Ca^{2+}$-ATPase (SERCA)), golgi apparatus (golgin-97) or mitochondria (cytochrome c (cyt c)). The lysosomal localization was also observed in living cells, where the endocytosed rHsp70 co-localized with Lysotracker® Red but not with Mitotracker® Red. In order to determine the amount of endocytosed Hsp70 the fluorescent signal from the rHsp70*-loaded cells was quantified, which revealed that an average of 70 ng rHsp70* is taken up pr. $1*10^5$ cells. To determine whether endocytosed rHsp70* was merely localized to the lumen or whether it would have a direct attachment to the endo-lysosomal membranes, the rHsp70*-loaded U-2-OS cells were sub-fractionated and the amount of rHsp70* present in the light membrane fraction (LMF) measured (cellular organelles including early and late endosomes and lysosomes). Freeze fracturing of the organelles in the LMF via repeated freeze/thaw cycles in liquid nitrogen, resulted in the total release of Cathepsin B into the supernatant, whereas the lysosomal membrane protein LAMP-2 was retained in the pelleted, fractured membrane fraction. Quantification of the endocytosed rHsp70* revealed that approx. ⅓ of the total rHsp70* remained in the pellet, strongly suggesting that it was bound to the endo-lysosomal membranes. In order to assess whether the endocytosed rHsp70 could stabilize the lysosomal membranes, cells were loaded with acridine orange, a metachromatic weak base that accumulates in the acidic compartment of the cells, i.e. late endosomes and lysosomes, and sensitizes them to photo-oxidation upon exposure to blue light (Brunk et al., 1997; Nylandsted et al., 2004). The photo-oxidation results in the loss of the lysosomal pH-gradient and leakage of acridine orange to the cytosol. This can be readily visualized and quantified as acridine orange exhibits red fluorescence when concentrated in the acidic compartment of the cell and green fluorescence when at a lower concentration in the cytosol. Remarkably, the endocytosed rHsp70 protected the lysosomes against blue light-induced photo-oxidation, whereas no protection was observed in cells loaded with recombinant Hsc70 and Hsp70-2, which share 86% and 84% amino acid sequence homology with Hsp70, respectively. Furthermore, a short interfering RNA (siRNA) specific for Hsp70 sensitized lysosomes of U-2-OS cells to photo-oxidation, and this effect was fully reverted by endocytosed rHsp70 aptly demonstrating that the protective effect of endogenous Hsp70 is mediated by the small fraction of the protein localized to the lysosomal lumen rather then the large pool residing in the cytosol. The above demonstrated effective endocytic uptake of Hsp70 and lysosomal stabilization may explain the recently reported surprising neuroprotective effects of extra cellular Hsp70 administered to the sites of injury following a variety of treatments known to trigger the lysosomal cell death pathway, i.e. retinal light damage and sciatic nerve axotomy.

In order to test whether the protective effect of Hsp70 could be a consequence of a direct association of Hsp70 with the lysosomal membranes, the inventors investigated its interaction with palmitoyl-oleoyl-phosphatidylcholine (POPC) large unilamellar vesicles (LUVs) containing a variety of membrane-associated anionic lipids, i.e. palmitoyl-oleoyl-phosphatidylserine (POPS; primarily in inner leaflet of the plasma membrane), cardiolipin (primarily mitochondrial) and BMP (primarily in late endosomes and lysosomes). Taking into account the increasingly acidic milieu of the endo-lysosomal compartment upon maturation to lysosomes, the protein-lipid interactions in neutral (pH 7.4) and acidic (pH 6.0) conditions were compared. At pH 7.4, rHsp70 caused a little relative change in the 90° light scattering in POPC liposomes indicating a very weak binding to the POPC bilayer. As reported earlier for POPS, all negatively charged lipids enhanced the binding of rHsp70 to the liposomes at neutral pH. This enhancement was approximately 4-fold irrespective of the negative lipid or the charge density on the liposome surface (POPS has a net charge of −1, and cardiolipin and BMP have a net charge of −2). Remarkably, lowering of the pH from 7.4 to 6.0 dramatically changed the lipid association profile of rHsp70. Whereas the binding to POPS was only slightly increased upon acidification, the binding to BMP was almost 20 times stronger in the acidic pH as compared to the neutral pH. The pH-dependent, high affinity binding of Hsp70 to BMP was confirmed in an independent set of BIAcore experiments.

In order to test whether the pH-dependent high affinity interaction between Hsp70 and BMP observed in vitro was required for the Hsp70-mediated stabilization of lysosomes in living cells, the inventors targeted the cellular BMP by loading the endo-lysosomal compartment of U-2-OS cells with BMP antibodies as demonstrated earlier (Kobayashi et al., 1998). Remarkably, BMP antibodies effectively inhibited the ability of rHsp70 to confer protection against photooxidation-induced lysosomal leakage. Even more importantly, BMP antibodies significantly sensitized U-2-

OS osteosarcoma cells to cisplatin, which induces an early lysosomal membrane permeabilization in U-2-OS cells as well as other cisplatin sensitive cell lines used in this study. Accordingly, also PC-3 and DU-145 prostate carcinoma cells were significantly sensitized to cisplatin-induced cell death upon treatment with anti-BMP antibodies.

Having confirmed that the lysosomal Hsp70-BMP interaction is essential for the cytoprotective effect of Hsp70, the inventors next investigated which part of the Hsp70 protein is responsible for the lipid binding. To determine this, the fluorescence shift of the tryptophans (W90 and W580) upon docking of rHsp70 into BMP-containing liposomes at pH 6.0 was measured. The inventors produced rHsp70 mutant proteins with deletions of the two major functional domains of the protein, i.e. the amino-terminal ATPase domain (rHsp70-ΔATP, deletion of amino acids 119-426) and the carboxy-terminal peptide-binding domain (rHsp70-ΔPBD; deletion of amino acids 437-617). The loss of signal in relative peak fluorescence intensity for Hsp70-ΔATP indicated that the ATPase domain is required for the high affinity binding of Hsp70 to the POPC/BMP bilayer. Next, the two tryptophans in Hsp70 were substituted with phenylalanines (W90F and W580F) in order to study which tryptophan is responsible for the lipid binding and fluorescence shift. The reduction of the signal with rHsp70-W90F that lacks the tryptophan in the ATPase domain (rHsp70-W90F) and the unchanged signal with rHsp70-W580F that lacks the tryptophan in the peptide-binding domain indicated that the tryptophan in the position 90 docked into the lipid layer. As the method used above only measured the relative shift in fluorescence upon tryptophan embedding into the lipophilic environment, the inventors also analyzed the lipid association of rHsp70 and its mutants in a more quantitative manner employing a BIAcore 2000 system with immobilized BMP-containing LUVs on the surface of an L1 sensor chip at pH 4.5. Both rHsp70 and rHsp70-ΔPBD showed a strong interaction with BMP, whereas the binding of rHsp70-ΔATP was markedly reduced confirming that Hsp70 interacts with BMP mainly through its ATPase domain. Surprisingly, the tryptophan mutants showed a striking difference in their ability to interact with BMP. Whereas the rHsp70-W580F mutant had essentially the same interaction profile as rHsp70, the binding of rHsp70-W90F mutant was dramatically decreased. Since rHsp70-W90F was properly folded as analyzed by far- and near-UV circular dichroism and capable of folding luciferace and hydrolyzing ATP, the W90F mutation specifically abolished the interaction between Hsp70 and BMP whilst retaining the structural and functional aspects of the Hsp70 chaperone. Thus, the rHsp70-W90F mutant unexpectedly provided us with an invaluable tool to further test whether the direct interaction between Hsp70 and BMP endows Hsp70 with its lysosome protective attributes. Indeed, the rHsp70-W90F mutant had completely lost its ability to protect the lysosomal membranes against photo-oxidation and cells against cisplatin-induced lysosomal cell death, whilst the rHsp70-W580F mutant showed the same efficacy as the wild-type protein. Also the rHsp70-ΔPBD mutant that showed an unchanged capacity to bind to BMP rich membranes had lost its ability to protect against photo-oxidation and cisplatin. These findings demonstrate that the binding of Hsp70 to BMP is required but not sufficient to endow the lysosomal membranes with protection. In addition, an intact carboxy-terminal peptide-binding domain is necessary for the stabilization of lysosomal membranes in living cells.

Hsp70 inhibitors have for long been considered as interesting anti-cancer drugs. Attention has, however, concentrated on inhibiting the cytosolic Hsp70, and problems regarding drug-delivery and lack of specificity among the Hsp70 family members have presented impassable barriers for the development of suitable Hsp70 antagonists. Having established that both the binding to BMP and an intact peptide-binding domain are required for the cytoprotective effect of Hsp70, and having verified the potential in targeting Hsp70-BMP interaction, the inventors next tested whether the protective effect of the endo-lysosomal Hsp70 could also be counteracted by inhibitors of Hsp70 chaperone activity. This was accomplished by incubating the cells with an apoptosis inducing factor-derived peptide (ADD70), which inhibits the chaperone function of Hsp70 by binding to its peptide-binding domain. It should be noted that this large peptide (388 amino acids) does not cross the plasma membrane, and thereby it provided us with another tool to specifically target the endo-lysosomal Hsp70. Notably, incubation of cells with ADD70 peptide completely blocked the lysosome-protective effect of endocytosed rHsp70 in U-2-OS cells. In order to test whether ADD70 could also counteract the cytoprotective effect of cells own Hsp70, the inventors investigated its effect on cisplatin-induced cytotoxicity in Hsp70 transgenic immortalized murine embryonic fibroblasts (iMEFs), in which the transgenic Hsp70 confers almost complete resistance against cisplatin-induced cell death. Remarkably, ADD70-treatment of Hsp70-transgenic iMEFs effectively abolished the Hsp70-mediated protective effect and rendered them as sensitive to cisplatin as wild type iMEFs. The wild type iMEFs express very low levels of Hsp70, and thus the inability of ADD70 to further sensitize them to cisplatin supports the idea that ADD70-mediated sensitization is, indeed, due to the inhibition of Hsp70. Akin to anti-BMP treatment, also ADD70 treatment sensitized PC-3 and DU-145 prostate carcinoma cells to cisplatin-induced cytotoxicity.

The data presented herein show that Hsp70 interacts directly with the endo-lysosomal anionic phospholipid BMP and that this interaction stabilizes endo-lysosomal membranes. Because the concentration of BMP increases in endocytic vesicles as the endosomes mature to form multivesicular bodies, late endosomes and lysosomes, the pH-regulation might be the way by which Hsp70 is targeted to BMP and lysosomes. Hsp70 subdomains differ markedly in their pI values, the ATPase domain having 1.72 units higher pI than the peptide-binding domain. This characteristic suggests that at acidic pH, the ATPase domain is preferentially positively charged, which could facilitate its interaction with anionic lipids. As the pH is lowered during the endocytic maturation, the positive charge would build up and any anionic interaction would be enhanced even further. The data presented herein demonstrating the dependence of Hsp70-BMP interaction on acidic pH and the ATPase domain support this theory. Furthermore, molecular modeling of the electrostatic surface of the ATPase domain of Hsp70 revealed that it forms an almost wedge-like structure with a predominantly positive charge at the bottom of the wedge even at pH 7.0. Interestingly, W90 lies within this positively charged domain, which might give clues to why the Hsp70-W90F mutation has such a profound impact on the ability of Hsp70 to interact with BMP and stabilize lysosomes. BMP is localized exclusively in the inner membranes of the endo-lysosomal compartment, where it supports disintegration and lipid extraction from lipid vesicles by acid sphingomyelinase and sphingolipid activator proteins giving rise to metabolites such as ceramide and sphingosine-1-phosphate, which have been implicated in destabilization of membranes and cell death. It should be noted that lysosomal inner membranes can be reached by invagination of the perimeter membranes at the level of early and late endosomes, and, therefore, the respective vesicles are likely to also contain Hsp70. Accordingly, Hsp70 may interfere with BMP's role as a cofactor for sphingolipid hydrolysis and thereby alter the lipid composition of the lysosomes. In order to test this hypothesis, the inventors are presently developing mass-spectroscopy based technology for quantification of lysosomal sphingolipid metabolites.

Accumulating data suggest that increased expression and altered trafficking of lysosomal proteases may form an "Achilles heel" for tumor cells by sensitizing them to lysosomal membrane permeabilization. Therefore, the BMP-Hsp70 interaction on the endo-lysosomal membranes and the resulting stabilization of the endo-lysosomal compartment provide the cancer cells with protection against this otherwise direct route to cell death. The molecular mechanism underlying this cytoprotective effect now opens new exiting possibilities for sensitization of cancer cells to agents that induce lysosomal cell death pathways via specific inhibition of the lysosome stabilizing function of Hsp70. Vice versa, the interaction between Hsp70 and BMP might provide new treatment strategies relying on the cytoprotection offered by the lysosome-stabilizing function of exogenously administered Hsp70 for insults as diverse as pancreatitis, motor and sensory nerve lesions and light-induced retinal damage.

Materials and Methods
Cell Culture and Reagents

Human U-2-OS osteosarcoma cell lines were cultivated in RPMI 1640 (Invitrogen) supplemented with 6% heat-inactivated calf serum and penicillin-streptomycin.

Hsp70 transgenic and appropriate control iMEFs were generated and maintained as described previously (Nylandsted et al., 2004). All cells were grown at 37° C. in a humidified air atmosphere with 5% $CO_2$ and repeatedly tested and found negative for mycoplasma.

Unless otherwise stated, all chemicals were purchased from Sigma-Aldrich (Sigma-Aldrich Denmark NS).
Recombinant Proteins Recombinant Hsp70 and its mutants were generated using the pET-16b vector system (Novagen) with induction of protein expression and subsequent $Ni^{2+}$-affinity-purification optimized according to the manufacturer's protocol.

Labeling of rHsp70 with Alexa Fluor 488 was done according to manufacturers protocol (Molecular Probes).
Cellular Uptake of Recombinant Proteins and Antibodies:

Sub-confluent cells were cultivated in RPMI 1640 (Invitrogen) supplemented with 6% heat-inactivated calf serum and penicillin-streptomycin. Recombinant proteins or reticulocyte lysates were added directly to the medium to obtain the final concentration. The cells were then grown another 20 h in presence of the protein/lysate.

Loading of cells with an antibody towards BMP (LBPA) (6C4) was done according to techniques in the art.

Quantification of endocytosed rHsp70* was done by growing cells 20 h in the presence of rHsp70* after which the cells where harvested, washed 3 times in PBS and counted. For whole cell uptake $1*10^5$ cells where used. The cells where lysed by incubation for 30 min on ice in 100 µL digitonin-PBS (200 µg/mL). Fluorescence was measured on a Spectramax Gemini platereader (Molecular Devices). For light membrane fractions (LMF) a total of $10*10^6$ cells where harvested, washed 3 times in PBS and Dounce-homogenized until membrane-breakage reached 90% as determined by trypan-blue staining. The cells where then subjected to membrane-fractionation by first clearing away the plasma membrane, nucleus and heavy membrane fractions after which the LMF was harvested by centrifugation at 17000*g for 20 min. The LMF was then split in two—the first being kept as the "full" LMF. The second fraction was freeze/thawn for 5 cycles in liquid nitrogen to break the membranes and subsequently centrifuged at 20000*g for 20 min in order to separate membranes from luminal content. All cell work after harvesting was done at max. 4° C.

Assays for Lysosomal Integrity and Cell Viability

Sub-confluent U-2-OS cells incubated with 2 µg/ml acridine orange for 15 min at 37° C. were washed, irradiated and analyzed in Hanks balanced salt solution complemented with 3% FCS. Cells for single cell imaging were selected from 8 pre-defined areas of each well in transmitted lightmode after which the same cells were immediately visualized and exposed to blue light from USH102 100W mercury arc burner (Ushio electric) installed in a U-ULS100HG housing (Olympus) for 20 sec. Fluorescence microscopy was performed on Olympus IX-70 inverted microscope with a LCPlanF1 x20 objective with NA=0,40. Loss of lysosomal pH gradient was quantified by counting the loss of intense red staining.

Apoptosis-like cell death was assessed by staining the cells with 0.05 µg/ml Hoechst 33342 (Molecular Probes) and counting cells with condensed nuclei in an inverted Olympus IX-70 fluorescent Microscope (Filter U-MWU 330-385 nm). For each experiment a minimum of eight randomly chosen areas were counted. The viability of cells was analyzed by the 3-(4,5-dimethylthiazole-2-yl)-2,5-diphenyltetrazolium bromide (MTT) reduction assay as described previously[67]. Necrotic cells where quantified by flow cytometry by staining the cells for 10 min at 37° C. with 2.5 µM SYTOX Green (Molecular Probes) and hereafter measure positively stained cells by their fluorescence intensity in the FL1 channel of a flow cytometer (FACSCalibur™; Becton Dickinson).

Cells were treated with cisplatin as indicated, cytosolic fractions were obtained by digitonin treatment and cytosolic cysteine cathepsin (zFRase) and caspase-3-like (DEVDase) activities were determined.
RNA Interference siRNAs used included one targeting the two genes encoding against Hsp70 (HSPA1A and HSPA1B); 5'-GC-CAUGACGAAAGACAACAAUCUGU-3' (Invitrogen) and a control Hsp70 siRNA described previously. Oligofectamine (Invitrogen) was used as a transfection agent.
Immunodetection Primary antibodies used included mouse monoclonal antibodies against Hsp70 (2H9; kindly provided by Boris Margulis, Russian Academy of Sciences, St. Petersburg, Russia), glyceraldehyde-3-phosphate dehydrogenase (GAPDH; Biogenesis), BMP (6C4; (Kobayashi et al., 1998)), LIMP-1 (H5C6; developed by J. Thomas August and James E. K. Hildreth and obtained from the Developmental Studies Hybridoma Bank developed under the auspices of the NICHD and maintained by The University of Iowa, Department of Biological Sciences, Iowa City, USA), cyt c (clone 6H2.B4, BD PharMingen), SERCA (IID8, Calbiochem), and golgin-97 (CDF4, Molecular Probes). Proteins separated by 10% SDS-PAGE and transferred to a nitrocellulose membrane were detected by using indicated primary antibodies, appropriate peroxidase-conjugated secondary antibodies from Dako, ECL Western blotting reagents (Amersham), and Luminescent Image Reader (LAS-1000Plus, Fujifilm).
Tryptophan Fluorescence Spectra and Liposome 90° Light Scattering The tryptophan fluorescence spectra (RFI) and liposome 90° light scattering (RSI) were analyzed in a HEPES buffer (20 mM HEPES, 0.1 mM EDTA, pH 7.4 or 6.0 as indicated) employing LUVs consisting of indicated lipids essentially as described previously. For the RFI, LUVs were added in 10

µM aliquots and spectra recorded after a 20 min stabilization period. For the RSI, recombinant proteins were added in 0.12 nmol aliquots.

Surface Plasmon Resonance (BIAcore)

For preparation of LUVs a lipid mixture consisting of 10 mol % sphingomyelin, 50 mol % phosphatidylcholine, 20 mol % cholesterol and 20 mol % BMP dissolved in organic solvents, was dried under a stream of argon and rehydrated in Tris/HCl buffer (pH 7.4) (Kolzer et al., 2004). The mixture was freeze-thawed nine times in liquid nitrogen and then in an incubator at 37° C. After ultrasound bath for 15 min the mixture was passed 21 times through a polycarbonate membrane with a pore diameter of 100 nm. Surface plasmon resonance measurements were performed using a BIAcore 2000 system at 25° C. LUVs (total lipid concentration 0.1 mM) were immobilized on the surface of a L1 sensor chip (BIAcore) in PBS (loading buffer). The running buffer used was sodium acetate buffer (50 mM, pH 4.5). As a control, acid sphingomyelinase (0.2 µM, 60 µl in running buffer) was injected directly on the liposome surface. Response units between 4100 RU-5250RU were obtained. The protein of interest was injected in running buffer at a flow rate of 20 µl/min at the concentrations indicated. After injection a dissociation phase of 10 min was appended.

Molecular Modeling

Primary structure analysis as well as molecular modeling were done with software available from the Expert Protein Analysis System (EXPaSy) proteomics server of the Swiss Institute of Bioinformatics (http://expasy.org/). Molecular modeling was done on basis of the crystal structure of the human Hsp70-ATPase domain (pdb code: 1S3X) and the human Hsc70 substrate binding domain (pdb code: 7HSC) with DeepView-Swiss PDB Viewer. Surface models were based on coulomb interaction at pH 7.0 using a solvent dielectric constant of 80 ($H_2O$).

Statistical Analysis

Statistical analysis was performed using a two-tailed, paired Student's T-test in order to evaluate the null-hypothesis. The cut-off level for statistical significance was set to 5% and all groups of data tested for the comparability of their variances using an F-test. All statistics were done on a minimum of n=3 independent experiments.

Discussion

The literature has provided evidence that Hsp70 could be present on plasma membranes of tumor cells, as well as in the endolysosomal system. It was furthermore known that Hsp70 could be released to the bloodstream during different stress-inducing events, the most typical being fever, trauma and strenuous exercise, the most intriguing probably being from psychological stress, although this work was mainly done in the field of immunology. The presence of Hsp70-species inside the endolysosomal compartment had also been described for another member of the Hsp70 family; the constitutively expressed Hsc70. The function of Hsc70 at this location had indeed given name to the process known as chaperone-mediated autophagy.

However, from the literature nothing was known about the molecular basis for the association of Hsp70 with plasma- and endolysosomal membranes, which lead the inventors to the formulation of this project.

The data presented in Example 1 show that Hsp70 is capable of interacting with negatively charged membrane lipids such as phospatidylserine (PS), cardiolipin and bis (monoacylglycero)phosphate (BMP) at neutral pH. Upon mimicking the acidity which can be expected in the early endolysosomal system (pH 6.0), however, the interaction profile dramatically changes, and the affinity of Hsp70 for BMP becomes 20-fold higher than at neutral pH and almost 9-fold greater than for PS. This Hsp70-BMP interaction was verified in a more elaborate BIAcore system, in which the pH was now set to that expected in late endosomes and lysosomes (pH 4.5), the main sites for the majority of cellular BMP. Interestingly, the known BMP-interacting protein; acid sphingomyelinase (aSMase), which rely on BMP as a cofactor, only shows half the affinity for BMP compared to that of Hsp70, illustrating the high relative affinity of Hsp70 to BMP.

The interaction of Hsp70 with PS has also been reported by others, as has an interaction between mouse Hsp70 and acidic glycoceramides, in which the interaction depended on the N-terminal ATPase domain and in some cases also on the peptide binding domain (PBD). However, contrary to the systems employed herein, these findings were done in systems consisting of basically only one lipid (90-100% and 100% pure lipid, respectively), not likely to resemble any marginally complex lipid environment, which one will expect in the eukaryotic cell. However, the importance of the N-terminal region of Hsp70 for acidic lipid association as shown by Harada et al. is in accordance with the inventors finding, that the interaction of Hsp70 with BMP depends on its N-terminal ATPase domain. The inventors further show that tryptophan 90 (W90) of Hsp70 is a critical amino acid as its mutation significantly reduces the Hsp70-BMP interaction. A hypothetical model argues that Hsp70 contain specific binding sites for the hydrophilic and -phobic parts of acidic glycolipids both in the ATPase as well as in the peptide-binding domain (PBD).

Although this model might be applicable for Hsp70 binding to acidic glycolipids, the inventors would rather suggest another model for the Hsp70-BMP interaction. Based upon the data presented herein that; I) the PBD is only capable of much weaker interactions with BMP; II) the importance of W90; III) the binding properties of the ATPase domain; and IV) the molecular modeling of surface electrostatic potential of Hsp70, the inventors suggest that Hsp70 interacts with BMP via an electrostatically positively charged, wedge-like, sub-domain at the bottom of the ATPase cleft. As conservative mutation of W90 to phenylalanine significantly reduces the Hsp70-BMP interaction without affecting the refolding- or ATPase activities of Hsp70, and since this single amino acid mutation does not change the electrostatic profile, it is possible, however, that an intermediate of the two models is more appropriate in explaining the interaction of Hsp70 with a more common anionic lipid motif. In such a model, the positive surface charge could facilitate electrostatic interactions and particular residues such as W90 might be involved in determining specificity of binding of anionic lipid binding partners—in this case, BMP. Interestingly, this could potentially implicate Hsp70 as a more general regulator of lipid homeostasis in the cell. Supporting this are data demonstrating that the lipid membranes of cells might serve as the primary sensors of stress such as fever and oxidative stress and hence as the initial inducers of the stress response. In face of stress, one could argue that the lipid membranes of the cell would be crucial compartments to keep in homeostasis or indeed modify in order to trigger specific signaling events as a response to the cellular challenge. The binding of Hsp70 to lipids such as BMP and the following increased stability of lysosomal membranes and perhaps other cellular lipid events could thus represent a part of a general cellular stress response. In the case of cancer such a response might have been hi-jacked to serve the cancer's own end, but also from a broader evolutionary perspective, a coordinated protein-lipid response in the face of cellular stress would make good sense.

The data presented herein showing that only Hsp70, not Hsc70 and Hsp70-2, are capable of directly protecting lysosomal membranes argue that a potential lipid stress response might be specifically regulated by the major stress-induced Hsp70 itself and not other Hsp70-species. However, as is also shown, depletion of Hsp70-2 also leads to lysosomal membrane permeabilization and cell death, although in this case the pathway is indirect as it depends on LEDGF. The mechanism for how LEDGF affects the lysosomal membranes remains unresolved, however.

In order to validate the in vivo relevance of the Hsp70-BMP interaction, the inventors targeted BMP by endocytosed antibodies and lysosomal Hsp70 by endocytosis of the otherwise cell-impermeable AIF-derived polypeptide ADD70. This verified that the interaction between Hsp70 and BMP serves to stabilize lysosomal membranes as cells subsequently where significantly sensitized to the effects of direct lysosomal membrane disruptive stimuli as well as the LMP-inducing chemotherapeutic agent cisplatin, the programmed cell death-profile of which was characterized as part of this project. Expression of ADD70 has formerly been shown to sensitize cancer cells to a variety of death stimuli and decrease the tumorigenicity of rat colon carcinoma and mouse melanoma cells in syngeneic animals. The major difference between this approach and the approach presented herein is that the present inventors sought to specifically target the lysosomal Hsp70 through endocytosis of ADD70, whereas the former studies utilized cytosolic expression of ADD70 in order to target the more abundant cytoplasmic Hsp70. The success in targeting the endolysosomal Hsp70-BMP interaction also provided a certain proof-of-concept of the idea of targeting lysosomal components through endocytosis for therapeutic means, a concept which could have broad therapeutic implications, as one could imagine sensitizing e.g. cancer cells to agents that induce lysosomal cell death pathways via specific inhibition of the lysosome stabilizing function of Hsp70. Vice versa, the interaction between Hsp70 and BMP might provide new treatment strategies relying on the cytoprotection offered by the lysosome-stabilizing function of exogenously administered Hsp70 for insults as diverse as pancreatitis, motor and sensory nerve lesions and light-induced retinal damage. Indeed, the concept of utilizing the endocytic machinery for introduction of specific cytotoxic compounds have already been explored, as endocytic delivery of a hydrocarbon-stapled BH3 helix based on the pro-apoptotic BH3 interacting domain death agonist, Bid, was shown to induce apoptosis in leukemia cells. This process depended on the BH3 helix leaving the endocytic compartment intact and activating Bax and Bak in order to induce cytochrome c release and activate a mitochondrial program of apoptosis. However, the mechanism of escape from the endocytic system was unfortunately not addressed in this paper.

As shown herein, the interaction between Hsp70 and BMP depends on the ATPase domain of Hsp70. Interestingly, recent reports on the Hsp70 cochaperone, Hsp70 binding protein 1 (HspBP1), might emphasize the importance of this positively charged area of Hsp70. A study of the crystal structure of HspBP1 complexed with part of the ATPase domain of Hsp70 has revealed that the interaction between these two was mediated by a curved, all α-helical fold in HspBP1 containing four armadillo-like repeats. The concave face of this curved fold embraces lobe II of the ATPase domain, the same lobe which forms the major part of the electrostaticaly positively charged volume of Hsp70s ATPase domain, which the inventors argue mediate the interaction between Hsp70 an BMP. A further perspective on this is provided by a another study, in which 14 cancer cell lines were characterized with regard to their relative Hsp70/HspBP1 levels. This other study found that cell lines with a high HspBP1/Hsp70 molar ratio were more susceptible to anticancer drugs than those with low ratio and that overexpression of HspBP1 promoted lysosomal membrane permeabilization. Based on these reports, and the data presented in this Example, one could argue for a model in which HspBP1 by binding to the positively charged area of the ATPase domain of Hsp70, disrupts its interaction with BMP and hence its stabilizing effect on endo-lysosomal membranes, resulting in increased sensitivity to LMP-inducing stimuli. As such, the armadillo-repeat domain of HspBP1 could potentially form the basis of an intelligent drug design, much as the case for ADD70. The efficacy of such HspBP1-derived molecules would be easy to test in the systems described herein and presents an interesting path towards further applications of the molecular mechanism described herein.

As the inventors show herein, Hsp70 binds with high affinity to BMP at acidic pH 4.5, even almost 2-fold higher than what is the case for the "classical" BMP binding partner acid sphingomyelinase (aSMase). Interestingly, BMP serve as a stimulatory cofactor for enzymatic hydrolysis of not only sphingomyelin via aSMase, but of most membrane-bound sphingolipids as it also functions as a cofactor for sphingolipid activator proteins (SAPs/Saposins) A-D. An obvious question would thus be, whether Hsp70 by its binding to BMP somehow alters the binding properties of aSMase and the Saposins, hereby modifying the catabolism of membrane sphingolipids and glycosphingolipids and the generation of downstream effector molecules such as ceramide and its metabolites, Ceramide-1-phosphate, sphingosine and sphingosine-1-phosphate, all of which have been implicated in both cell survival and death. Indeed, the inventors have found that Hsp70 is capable of modulating the binding of aSMase to BMP-containing liposomes at pH 4.5, depending on the concentration of Hsp70. As can be seen, low concentrations (3-150 nM) of Hsp70 facilitate the interaction of aSMase with BMP-Hsp70 liposomes, whereas higher concentrations of Hsp70 (300-1500 nM) has the opposite effect. Although our working concentration in the medium when Hsp70 is added for endocytosis is 300 nM, it would be hard to estimate a given intralysosomal concentration on this basis and any conclusions as to what effect Hsp70 might have on aSMase activity in vivo would remain speculative. However, staining of the Hsp70-transgenic (Hsp70-TG) and wildtype (WT) iMEFs with a monoclonal antibody against ceramide revealed that the Hsp70-transgenic mice show a clear upregulation of ceramide, which is present in a characteristic beads-on-a-string pattern in the peripheri of the cells as well as near the nucleus. Further analysis of the ceramide-profile of the iMEFs via lipid extraction and subsequent lipid mass spectroscopy has confirmed these findings, as the cumulative levels of ceramide were increased from an average 10.2 ng ceramide/mg protein for the iMEF-WT to 14.9 ng/mg for the Hsp70 transgenic iMEFs. The inventors have further substantiated that this effect can be ascribed to the action of Hsp70, as the inventors have also profiled our U-2-OS cells loaded with rHsp70 (i.e. 300 nM rHsp70 in full media for 24 h, analogous to all other Hsp70-endocytosis experiments presented herein). The quantification of ceramide in Hsp70-loaded U-2-OS cells showed an increase in cumulative levels of ceramide from 2.99 ng ceramide/mg protein for the control cells to 5.10 ng/mg for the Hsp70-loaded cells (the experiment has only been done once at the time of writing). However, taken together they all support a role for Hsp70 in modulating ceramide levels in cells, although further validation of course is needed. Yet, if these data can be verified, a series of questions present themselves, such as the compartmentalization of the ceramide species, quantification of specific ceramide-species (of which there is at least 50 distinct molecular species), profiling of ceramide levels in the face of various stresses, transformation status of cells etc.

Interestingly, a previous study has addressed one of these questions, which show that heat shock (42.5° C. for 2 h) causes the accumulation of ceramide in Molt-4 acute leukemic lymphocytes. This accumulation could be blocked by the pharmacological inibitors Fumonisin B1 and myriocin, the latter of which is regarded as a specific inhibitor of the de novo pathway of ceramide synthesis as it blocks the action of serine palmitoyltransferase, the enzyme which initiates the de novo synthesis of new sphingolipids from serine and palmitoyl-CoA. A partial mechanism for this increase in de novo synthesis of ceramide has been described in yeast, in which heat stress induces an acute influx of serine into the ER that drives de novo synthesis. It will be interesting to test if the increase in ceramide levels observed upon endocytosis of rHsp70 can be modulated by these pharmacological inhibitors or whether the observed increases stem from the catabolic pathways of sphingolipid degradation and the stimulation of these by Hsp70 binding to BMP. Of course, a compound model could also be hypothesized. In this model, an initial heat stress could lead to membrane fluidization, serine influx and rapid initiation of de novo sphingolipid synthesis. Subsequently, the induction of Hsp70, as a consequence of the heat stress, would lead to increased Hsp70 levels in the cell, Hsp70-interaction with BMP, increase in aSMase-activity—and possibly also SAP activity—resulting in the generation of ceramide by the catabolic pathways. This secondary response could either complement the initial de novo induction or maybe take over for it as the continuous de novo response would rely on a continuous supply of serine and palmitioyl-CoA. It remains however, to be tested if the cellular protection is a consequence of the increase in ceramide itself or maybe should be contributed to altered levels of its upstream and downstream metabolites.

At this point, some major questions remain to be answered—How does Hsp70 end up in the extracellular milieu and inside the endolysosomal compartment? Is Hsp70 secreted and then taken up by endocytosis?—or is it present inside lysosomes or more specialized secretory lysosomes, waiting for a release signal in the form of stress? And perhaps more importantly—what is the biological significance of the presence of Hsp70 in the extracellular environment?

Although the work presented in this work is not capable of answering these complex questions, some deductions can however be made. First, Hsp70 could be endocytosed in all cell lines tested in this project, arguing for a common way of recognizing extracellular Hsp70 (eHsp70). This is in accordance with data showing that eHsp70 can bind to a number of receptors on different leucocyte sub-populations. The receptors involved in extracellular Hsp70 (eHsp70) recognition mainly include pattern recognition receptors (PRRs) and consist of a variety of receptors from different receptor families such as the toll like receptors (TLR), scavenger receptors and c-type lectins. As the work in this project has not addressed by which initial mechanism Hsp70 is endocytosed (receptor-mediated, raft-dependent, clathrin-dependent etc.) it cannot be said whether PRRs are responsible for the endocytosis of eHsp70 seen in our systems. However, 10-fold excess of un-labelled Hsp70 could not compete with AF488-labelled Hsp70 uptake in neither U-2-OS cells nor iMEFs—on the contrary, endocytosis was significantly enhanced in the presence of excess un-labelled Hsp70, which to some extent argues against a saturable mechanism of uptake.

The focus of the immunological field has mainly been on the cytokine response and activation of the innate immune defence elicited by eHsp70 binding to the PRRs and hence not much regard has been given to the effect of eHsp70 after receptor binding and initiation of signaling.

The release mechanisms of Hsp70 into the extracellular milieu and the effects of Hsp70 once herein have to some extent been addressed, although a satisfying molecular insight into these exciting mechanisms is still lacking. Nevertheless, plenty of evidence exists for the presence of Hsp70 in the circulatory system after stress and accumulating data support a role for eHsp70, whether stress-induced or exogenously delivered, in neuroprotection as well as in priming the primary immune defence system.

With regard to release of Hsp70, the first evidence for the transfer of Hsp70 from one cell to another came from studies in the squid giant axon, and during the reproduction of these results in cultured rat embryo cells, evidence was presented that a non-classical pathway of exocytosis could be responsible for the release of Hsp70.

It has been suggested that Hsp70 along with other heat shock proteins are only released under pathological circumstances resulting in necrotic death and not during programmed cell death. Recent studies however, have shown that Hsp70 can be released from intact cells by active mechanisms and that the degree of stimulus determines the mode of release. Importantly, no known studies have reported a direct correlation between eHsp70 and markers of muscle damage although major increases of eHsp70 can be detected in the peripheral bloodstream upon physical exercise. Most convincing, and perhaps also most intriguing, are the discoveries showing that psychological stress such as predatory fear and electric shock can evoke a stress induced eHsp70 release, a process which was suggested to be dependent on cathecholamine signaling. This is particularly interesting as catecholamines via the ai-adrenergic receptor can lead to intracellular calcium-fluxes, and calcium-fluxes can cause exocytosis of exosomes, multivesicular bodies and lysosomes. As such, during times of stress, increases in noradrenaline acting upon ai-adrenergic receptors could result in a calcium flux within the cell with the subsequent release of Hsp70 within exosomes. Evidence for this hypothesis comes from demonstrations that eHsp70 can be released in vesicles characterized as exosomes, but evidence has also been presented that eHsp70 can be released as free eHsp70, both in cellular systems as well as in vivo. It has also been suggested that lipid rafts are needed for eHsp70 release although this has also been disputed. Moreover, it has been shown that a functional lysosomal compartment is necessary for release of eHsp70 and that this release is accompanied by the presence of lysosomal marker proteins on the surface of the cells, suggesting a secretion dependent on plasma- and lysosomal membrane fusion.

Regardless of whether the released Hsp70 is present in exosomes or as free eHsp70, it is interesting to note that some sort of secretory MVB/late endosomal/lysosomal compartment is apparently involved in all modes of release.

Based upon these data, and the results obtained herein, a more complex hypothesis for how Hsp70 escapes from the cytosol to the extracellular environment can be formulated. The release of Hsp70 would still depend on increases in intracellular calcium, as this would serve as the signal for exocytosis of endo-lysosomes. The presence of Hsp70 within this compartment would however be dependent on the interaction of Hsp70 and BMP as described herein, as Hsp70 would be effectively aggregated on BMP-containing inner membranes in late endosomes/MVBs/lysosomes. Hsp70 could either arrive in late endosomes and lysosomes from extracellular uptake such as endocytosis as also described herein, or through invaginations of the perimeter membranes of early and late endosomes as well as lysosomes, which would bring intracellular Hsp70 and BMP in proximity. The acidity of the compartment would maintain a strong preference for Hsp70s localization to BMP-containing membranes. Upon exocytosis, some Hsp70 would still be bound to BMP-containing exosomes, but the neutral pH encountered in the extracellular environment would now favour an Hsp70-BMP equilibrium shifted significantly towards more unbound Hsp70, resulting in both free as well as exosome-bound Hsp70, which could then exert their extracellular functions.

In summary, the data presented herein show that Hsp70 interacts directly and pH-dependently with the endo-lysosomal anionic phospholipid BMP. The inventors demonstrate that the binding of Hsp70 to BMP is mediated via Hsp70s ATPase domain, involving tryptophan 90, and that this interaction results in the stabilization of endo-lysosomal membranes, possibly by influencing the activity of other BMP-binding proteins. The inventors also show that the elucidation of this molecular mechanism opens new exiting possibilities for sensitization of cancer cells to agents that induce lysosomal cell death pathways via specific inhibition of the lysosome stabilizing function of Hsp70. Vice versa, the interaction between Hsp70 and BMP might provide new treatment strategies relying on the cytoprotection offered by the lysosome-stabilizing function of exogenously administered Hsp70.

Example 2

Interaction Between Hsp70 and Bis(Monoacylglycero)Phosphate Activates Acid Sphingomyelinase, Stabilizes Lysosomal Membranes and Promotes Cell Survival Heat shock protein 70 (Hsp70) is an evolutionarily highly conserved molecular chaperone that promotes the survival of stressed cells by inhibiting lysosomal membrane permeabilization, a hallmark of stress-induced cell death. Clues to its molecular mechanism of action may lay in the recently reported stress- and cancer-associated translocation of a small portion of Hsp70 to the lysosomal compartment. Here, we show that Hsp70 stabilizes lysosomes by enhancing the activity of acid sphingomyelinase (ASM), a lysosomal lipase that hydrolyzes sphingomyelin to ceramide and phosphorylcholine. In acidic environment Hsp70 binds with high affinity and specificity to an endo-lysosomal anionic phospholipid bis(monoacylglycero)phosphate (BMP), an essential co-factor for ASM, thereby facilitating the binding of ASM to BMP and stimulating ASM activity. The inhibition of the Hsp70-BMP interaction by BMP antibodies or a point mutation (W90A) in Hsp70 as well as the inhibition of ASM activity by desipramine effectively revert the Hsp70-mediated stabilization of lysosomes. Notably, the reduced ASM activity in cells from patients with Niemann-Pick disease A (NPDA), a severe lysosomal storage disorder caused by mutations in the ASM gene, is also associated with a dramatic decrease in lysosomal stability, and this phenotype can be effectively corrected by restoring the lysosomal ASM activity by treatment with recombinant Hsp70 or ASM. Taken together, these data open exciting possibilities for the treatment of lysosomal storage disorders and cancer with non cell permeable compounds that enter the lysosomal lumen via the endocytic delivery pathway.

Figure 5:
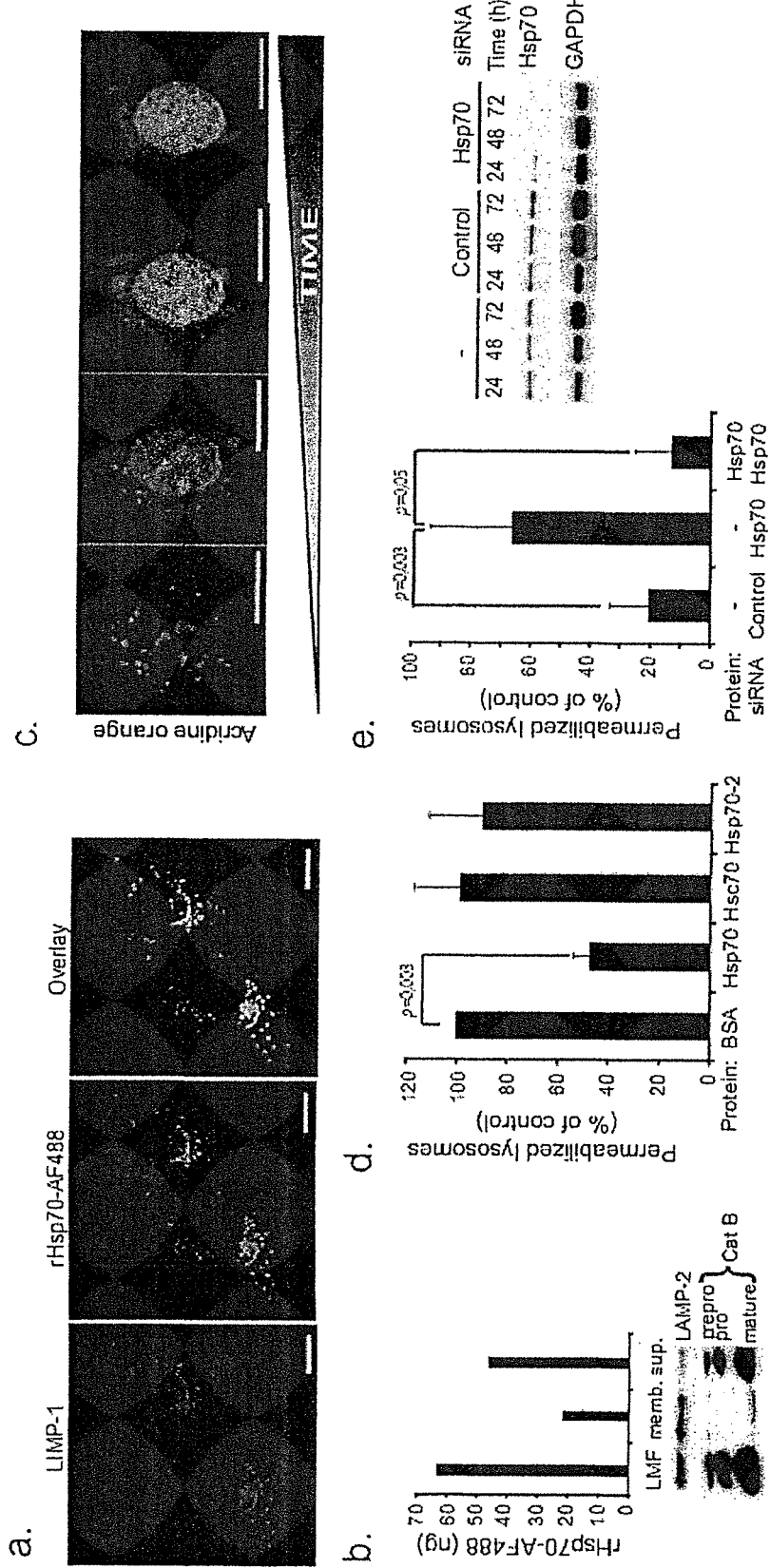
FIG. 5
Lysosomal Hsp70 stabilizes lysosomal membranes. (a) Representative confocal images of U-2-OS cells incubated with 300 nM rHsp70-AF488 (green) for 24 h, fixed and stained for lysosomal integral membrane protein-1 (LIMP-1; red). For co-localization with other organelle markers see FIG. 9. (b) U-2-OS cells were incubated with 300 nM rHsp70-AF488 for 24 h before quantification of rHsp70-AF488 in membranes (memb.) and supernatant (sup.) obtained by repeated freeze/thaw cycles and centrifugation the light membrane fraction (LMF). The immunoblot analyses of lysosome-associated membrane protein 2 (LAMP-2) and cathepsin B (Cat B) demonstrate the validity of the fractionation procedure. (c) Representative still images of U-2-OS cells exposed to photo-oxidation (acridine orange and blue light). The loss of lysosomal integrity is visualized by the loss of red and increase in green staining. (d and e) U-2-OS cells were incubated with indicated recombinant proteins (300 nM) for 24 h, and analyzed for lysosomal integrity upon photo-oxidation. When indicated, cells were treated with indicated siRNAs for 48 h prior to the addition of recombinant proteins (e). The values represent means±SD for three (d) or five (e) independent experiments. Representative immunoblots of indicated proteins from U-2-OS cells left untreated or treated with control or Hsp70 siRNAs are shown on the right. Scale bars: 20 μm (a and c).
Figure 9:
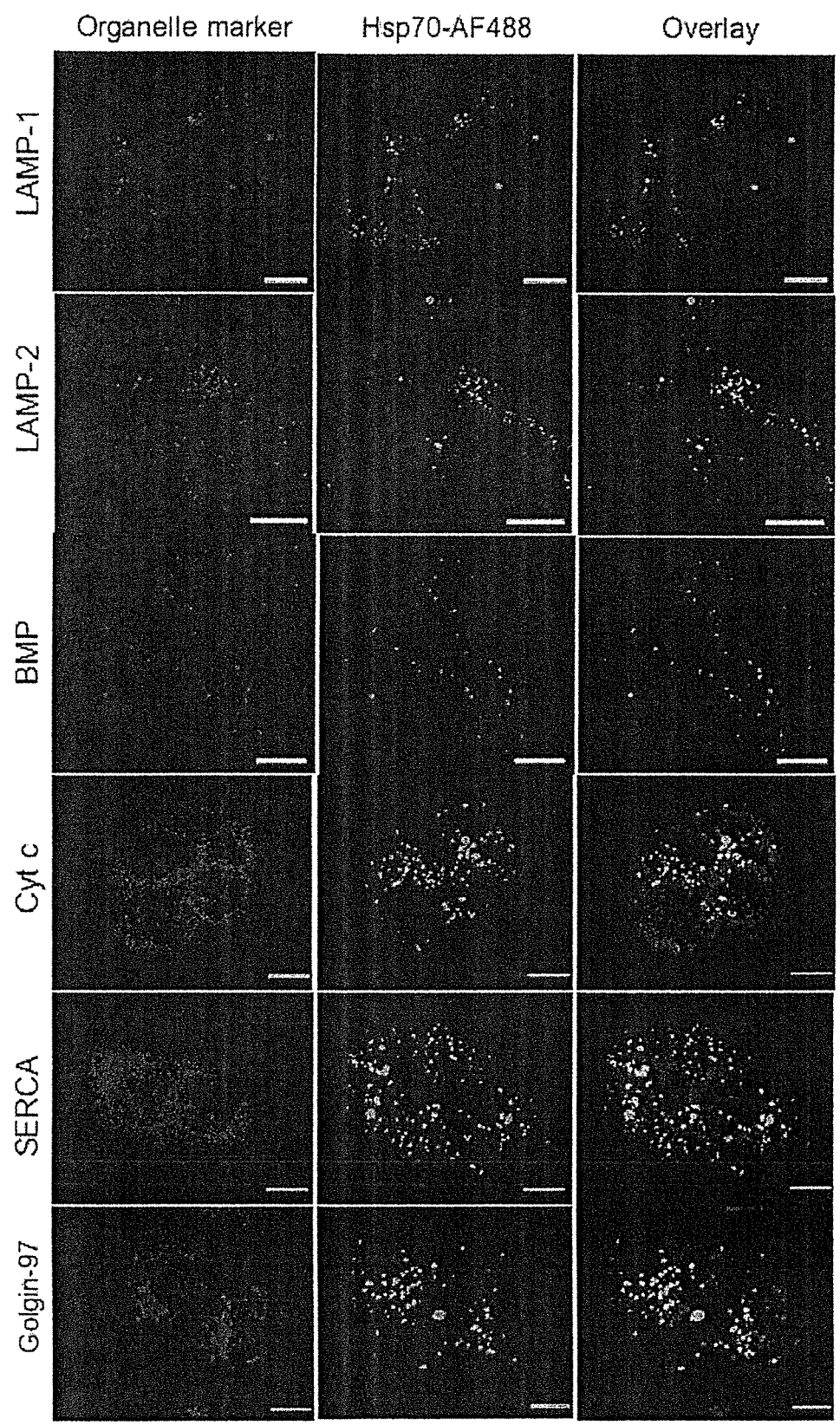

Lysosomal proteases, cathepsins, are important effectors in evolutionarily conserved cell death programs induced by a wide variety of stresses. Cathepsin-dependent cell death is characterized by an early lysosomal membrane permeabilization and subsequent translocation of cathepsins into the cytosol, where they can initiate caspase-dependent and -independent cell death pathways. In order to test whether the lysosomal localization is crucial for the reported ability of Hsp70 to stabilize lysosomal membranes and protect cells against stress-induced cell death, we took advantage of the endocytic machinery of cells to target recombinant Hsp70 (rHsp70) into the lysosomes. Immunocytochemical and biochemical analysis of U-2-OS osteosarcoma cells incubated with fluorochrome-labeled rHsp70 revealed effective uptake of rHsp70, its specific co-localization with late endosomal and lysosomal markers and binding to lysosomal membranes (FIG. 5a,b and FIG. 9). Using a real time imaging to monitor lysosomal membrane integrity (FIG. 5c), we showed that the endocytosed rHsp70 protected lysosomes against photo-oxidation (FIG. 5d). Furthermore, a short interfering RNA (siRNA) specific for Hsp70 sensitized the lysosomes to photo-oxidation, and this effect was fully reverted by endocytosed rHsp70 aptly demonstrating that the protective effect of endogenous Hsp70 is mediated by the small fraction of the protein in the lysosomal lumen (FIG. 5e). In spite of similar uptake (data not shown), no lysosomal stabilization was observed with recombinant Hsc70 and Hsp70-2, which share 86% and 84% amino acid sequence homology with Hsp70, respectively (FIG. 5d).

Figure 6:
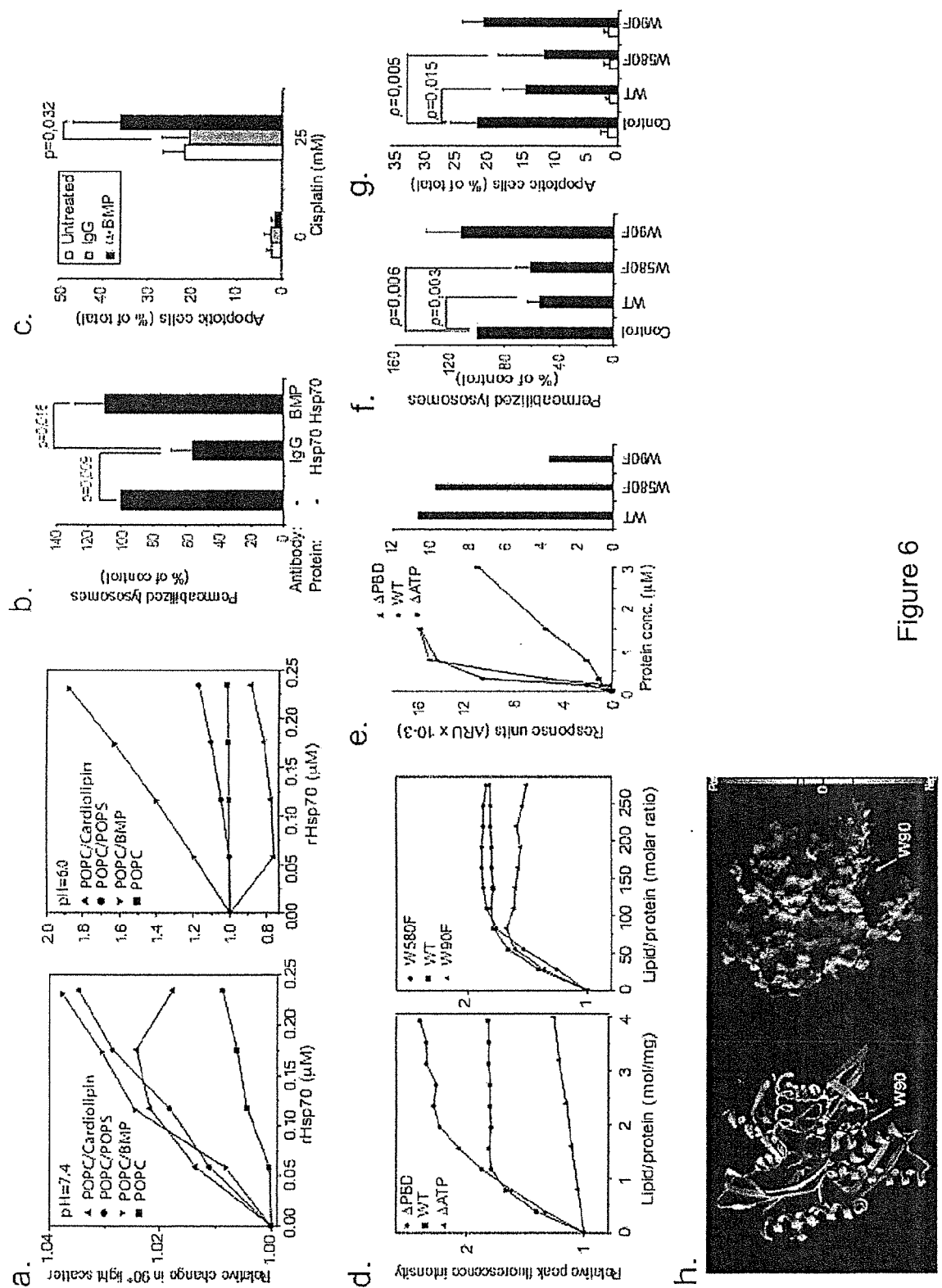
FIG. 6
A pH-dependent interaction between Hsp70 and BMP stabilizes lysosomal membranes. (a) Relative changes in liposome 90° light scattering upon addition of rHsp70 (in 0.12 nmol aliquots) to liposomes containing indicated lipids ($\chi$=0.2) at pH 7.4 (left) and pH 6.0 (right). (b) U-2-OS cells were left untreated (−) or incubated with 50 μg/ml anti-BMP or control IgG for 7 h before addition of vehicle (−) or 300 nM rHsp70 for 24 h, and analyzed for lysosomal integrity upon photo-oxidation. (c) U-2-OS cells were left untreated or incubated with 50 μg/ml anti-BMP or control IgG for 7 h before addition of vehicle (−) or 25 μM cisplatin for 24 h and analyzed for apoptotic cell morphology following Hoechst 33342 staining. (d) Interaction of rHsp70 and its mutants with POPC/BMP ($\chi$BMP=0.2) liposomes at pH 6.0 as measured by changes in relative peak fluorescence intensity. Protein concentrations were 0.36 μM (rHsp70), 0.5 μM (ΔATP) and 0.35 μM (ΔPBD) (left) or 0.43 μM (right), and liposomes were added in 10 μM aliquots. (e) BIAcore analysis of interactions between wild type rHsp70 (WT) and its deletion (ΔATP and ΔPBD) and point (W90F and W580F) mutants with immobilized LUVs at pH 4.5 (average diameter: 100 nm; total lipid concentration: 0.1 mM; composition: sphingomyelin ($\chi$=0.1), phosphatidylcholine ($\chi$=0.5), cholesterol ($\chi$=0.2) and BMP ($\chi$=0.2)). Liposomes were injected until equilibrium (100 s), and indicated concentrations (left) or 300 nM (right) of recombinant proteins in sodium acetate buffer (50 mM, pH 4.5) were injected for 200 s at a flow rate of 20 μl/min followed by a dissociation phase for 10 min. ΔRU is defined as the difference between the response signal measured after liposome equilibrium and protein-liposome equilibrium. (f and g) U-2-OS cells were left untreated (Control) or incubated with indicated recombinant Hsp70 proteins (300 nM) for 24 h, and analyzed for lysosomal integrity upon photo-oxidation (f), or treated with vehicle (white bars) or 25 μM cisplatin (Black bars) for 24 h and analyzed for the apoptosis like morphology (g). (h)
Figure 7:
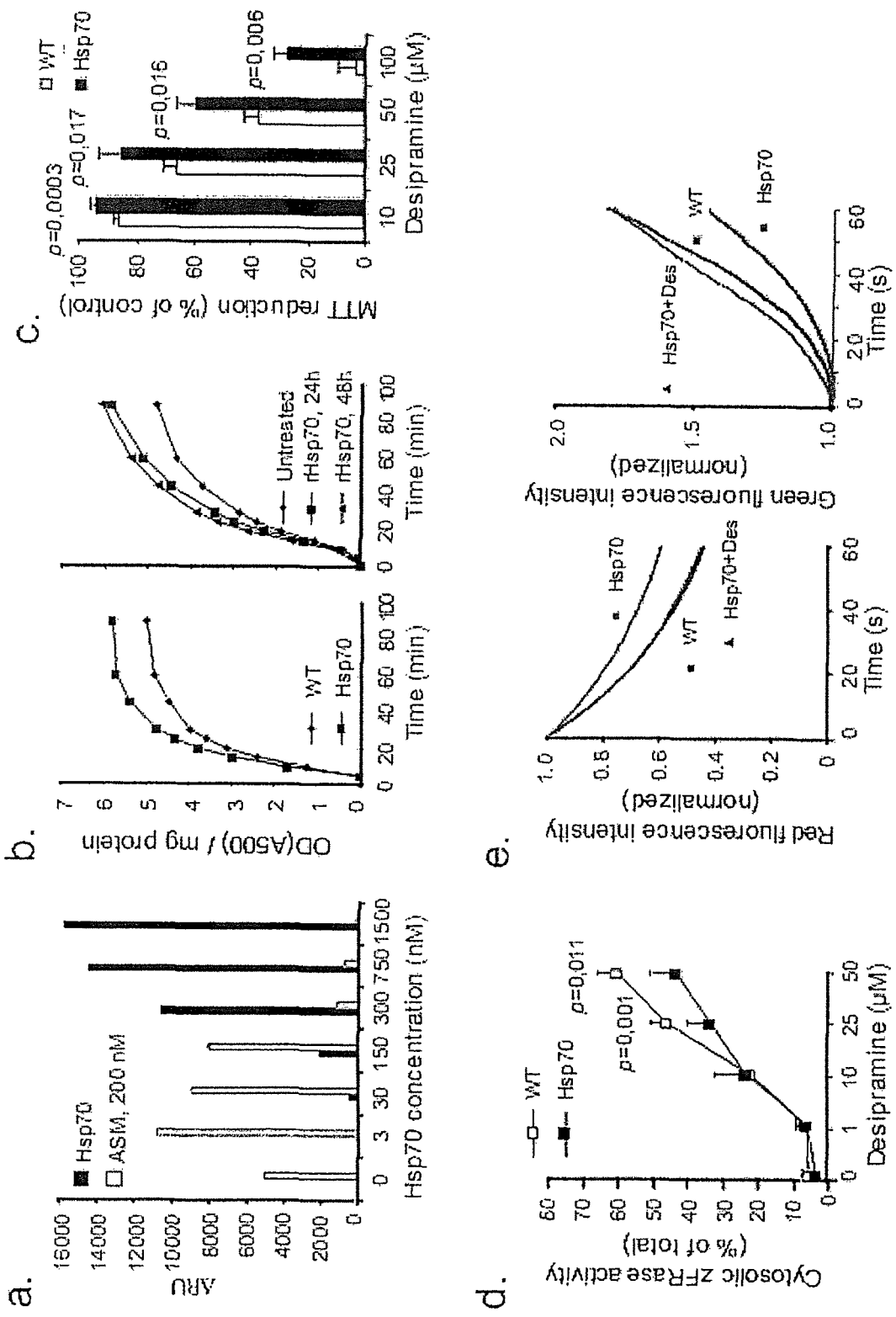

The presence of Hsp70 in the lysosomal membranes and its ability to survive the hydrolytic lysosomal environment suggest that it binds to the lysosomal membrane lipids. Thus, we investigated the interaction of Hsp70 with palmitoyl-oleoyl-phosphatidylcholine (POPC) large unilamellar vesicles (LUVs) containing various membrane-associated anionic lipids, i.e. palmitoyl-oleoyl-phosphatidylserine (POPS; primarily in plasma membrane), cardiolipin (primarily mitochondrial) and BMP (primarily in late endo-somes/lysosomes). Taking into account the increasingly acidic milieu of the endo-lysosomal compartment upon maturation to lysosomes, we compared the protein-lipid interactions in neutral (pH 7.4) and acidic (pH 6.0) conditions (FIG. 6a). At pH 7.4, rHsp70 caused a little relative change in the 90° light scattering in POPC liposomes indicating a very weak binding. As reported earlier for POPS, all negatively charged lipids enhanced the binding of rHsp70 to the liposomes at neutral pH approximately 4-fold irrespective of the charge density on the liposome surface (ranging from −1 to −2) (FIG. 6a). Remarkably, the binding to BMP was almost 20 times stronger at the acidic pH as compared to the neutral pH, whereas the binding to POPS was only slightly increased upon acidification (FIG. 6a). The high affinity binding of Hsp70 to BMP in acidic pH was confirmed in an independent set of BIAcore experiments (FIGS. 6e and 7a). Importantly, BMP antibodies delivered to the endo-lysosomal compartment by endocytosis effectively inhibited the ability of rHsp70 to stabilize the lysosomes in living cells (FIG. 6b), and sensitized the cells to cisplatin (FIG. 6c), an anti-cancer drug that induces lysosomal leakage.

In order to investigate which part of the Hsp70 protein is responsible for the BMP binding, we measured the fluorescence shift of the tryptophans upon docking of rHsp70 and its mutants into BMP-containing liposomes. The loss of signal in relative peak fluorescence intensity for the Hsp70 mutant lacking amino acids 119-426 in the amino-terminal ATPase domain (rHsp70-ΔATP), but not for that lacking amino acids 437-617 in the carboxy-terminal peptide-binding domain (rHsp70-ΔPBD), indicated that the ATPase domain was required for the high affinity binding of Hsp70 to BMP (FIG. 6d). Next, we substituted the two tryptophans in Hsp70 with phenylalanines (W90F and W580F) and studied which tryptophan is responsible for the fluorescence shift induced by lipid binding. The reduction of the signal only with rHsp70-W90F indicated that the NH2-terminus of the protein docked into the lipid layer (FIG. 6d). A more quantitative BIAcore analysis of the BMP—rHsp70 interaction confirmed that Hsp70 interacted with BMP mainly through its ATPase domain (FIG. 6e). Surprisingly, the W90F mutation specifically abolished the interaction between rHsp70 and BMP whilst retaining the structural (folding as analyzed by far- and near-UV circular dichroism) and functional (luciferace folding and ATP hydrolysis) aspects of the Hsp70 chaperone (FIG. 6e and data not shown). Thus, the rHsp70-W90F mutant provided us with an invaluable tool to further test whether the direct interaction between Hsp70 and BMP endows Hsp70 with its lysosome protective attributes. Indeed, the rHsp70-W90F mutant had completely lost its ability to protect the lysosomal membranes against photo-oxidation and cells against cisplatin-induced lysosomal cell death, whereas the rHsp70-W580F mutant showed the same protective effect as the wild-type protein (FIGS. 6f and g). Importantly, mutant Hsp70 proteins were endocytosed essentially as effectively as the wild type Hsp70 (data not shown). Thus, we conclude that the binding of Hsp70 to BMP is essential for the lysosome stabilizing effect of Hsp70.

Because the concentration of BMP increases in endocytic vesicles as the endosomes mature to form lysosomes, the pH-regulation might be the way by which Hsp70 is targeted to lysosomes. Calculations (PROTPARAM, EXPaSy proteomics server, Swiss Institute of Bioinformatics) revealed that the ATPase domain of Hsp70 has 1.72 units higher theoretical pI than the peptide-binding domain (6.62 vs. 4.9). This characteristic suggests that at acidic pH, the ATPase domain is preferentially positively charged, which could facilitate its interaction with anionic lipids. Our data demonstrating the dependence of Hsp70-BMP interaction on acidic pH and the ATPase domain support this theory. Furthermore, molecular modeling of the electrostatic surface of the ATPase domain of Hsp70 revealed that it forms an almost wedge-like structure with a predominantly positive charge at the bottom of the wedge containing W90 possibly explaining the profound impact of W90F mutation on the ability of Hsp70 to interact with BMP and stabilize lysosomes (FIG. 6h).

Figure 8:
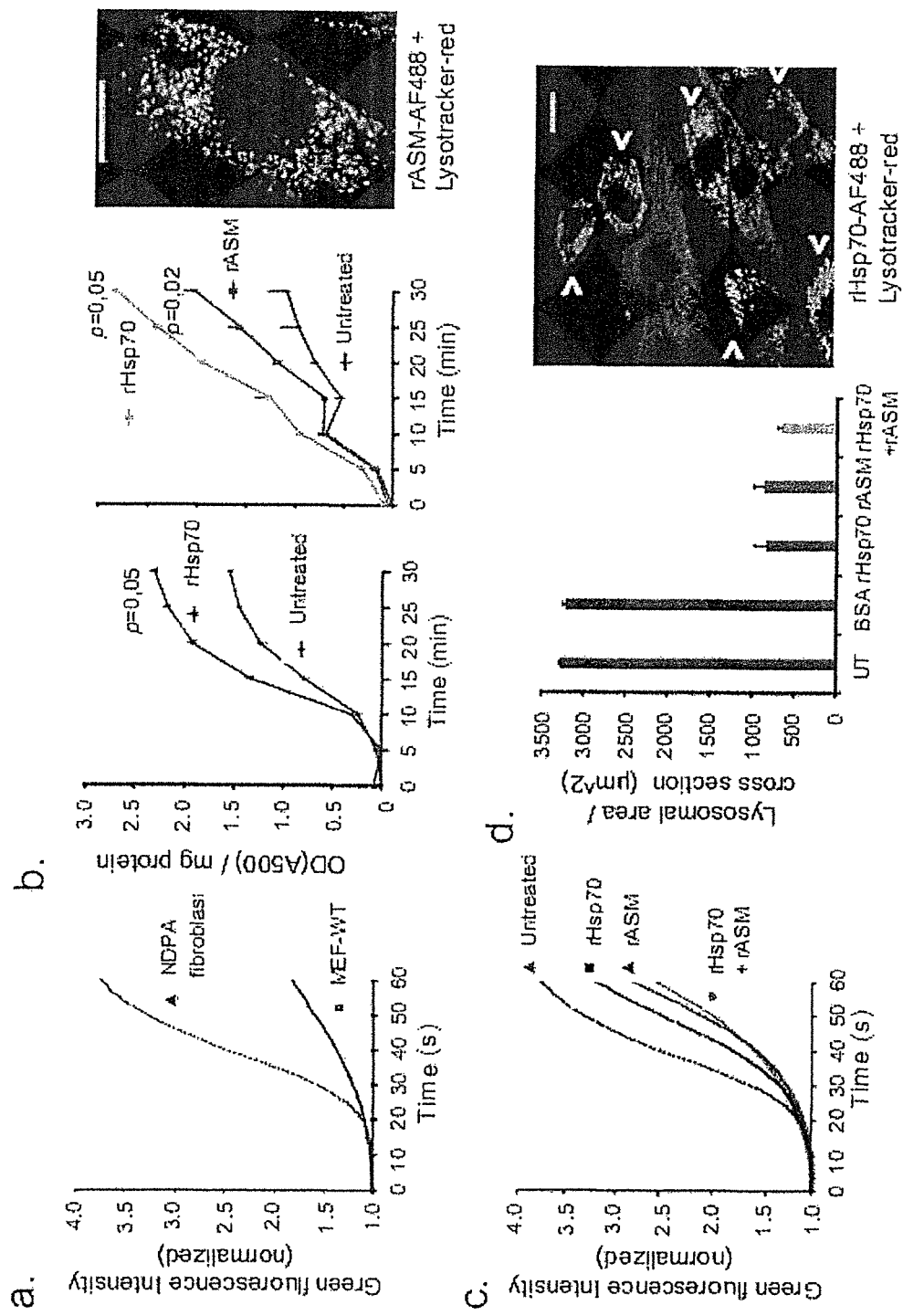
Figure 10:
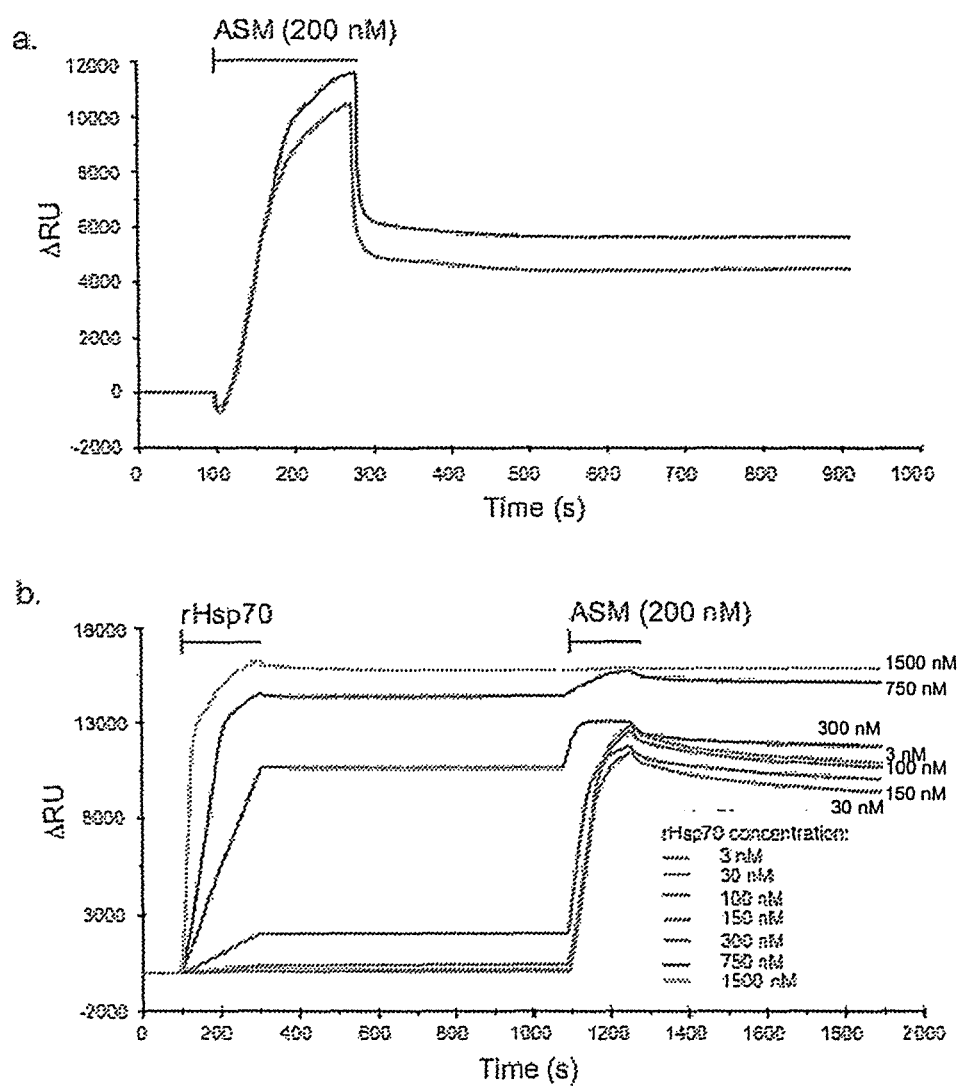

BMP binds ASM with high affinity and stimulates its ability to hydrolyze sphingomyelin to ceramide and phosphorylcholine. The BIAcore analysis revealed that pretreatment of the BMP-containing LUVs with rHsp70 at sub-equimolar concentrations facilitated the subsequent binding of ASM, whereas higher rHsp70 concentrations showed an inhibitory effect (FIGS. 7a and 10). Remarkably, Hsp70 transgenic murine embryonic fibroblasts (Hsp70-MEFs), which are protected against stress-induced lysosomal damage (FIG. 7e), displayed significantly higher ASM activity than wild type MEFs (WT-MEFs), and the treatment of WT-MEFs with rHsp70 at a cytoprotective concentration (300 nM) increased the ASM activity to the level comparable to that in Hsp70-MEFs (FIG. 7b). In order to test whether ASM is responsible for the lysosome stabilizing effect we treated the cells with desipramine, a well characterized pharmacological ASM inhibitor. Desipramine reduced the viability of MEFs in a dose-dependent manner and the cell death was associated with a massive permeabilization of lysosomes as demonstrated by the leakage of lysosomal cathepsins into the cytosol (FIGS. 7c and d). Notably, desipramine-induced cell death and lysosomal leakage were significantly reduced in Hsp70-MEFs as compared to WT-MEFs. Furthermore, inhibition of ASM with subtoxic concentration of desipramine reverted the lysosomal stress resistance of Hsp70-MEFs to the level of WT-MEFs as evidenced by accelerated loss of lysosomal membrane integrity upon photo-oxidation (FIG. 7e). The lysosome protective role of ASM was further supported by data showing that lysosomes in fibroblasts from patients with NPDA, a fatal lysosomal storage disorder caused by mutations in the ASM gene, displayed extreme sensitivity to photo-oxidation-induced damage (FIG. 8a). Remarkably, rHsp70 was also capable of enhancing the enzymatic activity of the endogenous mutated ASM as well as the simultaneously loaded rASM in the patient cells (FIG. 8b). The increased ASM activity obtained by loading the lysosomes with rHsp70, rASM or the combination of the two correlated with their ability to stabilize the lysosomes and to normalize the volume of the dramatically enlarged lysosomal compartment in NPDA cells (FIG. 8b-d). It should be noted that akin to rHsp70, also rASM localized to the lysosomes (FIG. 8b).

Taken together our data indicate that Hsp70-BMP interaction stabilizes lysosomes via a mechanism involving the regulation of sphingomyelin metabolism rather than direct physical stabilization of the membrane. Such an indirect effect is supported by the fact that BMP is localized exclusively in the inner membranes of the endo-lysosomal compartment, where its major function is to support the disintegration and lipid extraction from lipid vesicles by ASM and sphingolipid activator proteins. Interestingly, ASM-mediated increase in lysosomal ceramide concentration modifies the steric conformation of lysosomal membranes and thereby facilitates their fusion with other intracellular vesicles and plasma membrane. Thus, the changes in the lysosomal membrane composition and volume as a result of the ceramide-induced enhanced fusion capacity may contribute to the Hsp70-mediated increase in lysosomal stability. On the other hand, various apoptotic stimuli induce the translocation of ASM to the outer leaflet of plasma membrane, where ceramide can form lipid microdomains that function as sites for activation of membrane-associated signaling molecules involved in apoptotic signaling. Thus, ceramide may have opposing effects on cell survival depending on whether it is produced inside the lysosome or on the plasma membrane.

The above-described molecular mechanism underlying the cytoprotective effect of Hsp70 opens new exiting possibilities for sensitization of cancer cells to agents that induce lysosomal cell death pathways via specific inhibition of the lysosome stabilizing function of Hsp70. Vice versa, the ability of exogenously administered rHsp70 alone or in combination with rASM can be directly challenged as a novel treatment for NPD patients, whose therapeutic options are currently limited to gene and stem cell therapies.

Methods Summary

WT- and Hsp70-MEFs were generated, immortalized and maintained as described in the art. Human NPDA fibroblasts (83/24) originate from a skin biopsy of a 5 month old patient with hepatosplenomegaly. Recombinant proteins were generated using the pET-16b vector system and $Ni^{2+}$-affinity-purification (Novagen), and labeled with Alexa Fluor 488 according to manufacturers protocol (Molecular Probes). To analyze the lysosomal integrity, we developed a real time imaging method of cells stained with acridine orange, a metachromatic weak base that accumulates in the acidic compartment of the cells staining them red and sensitizing them to photo-oxidation. The photo-oxidation-induced loss of the lysosomal pH-gradient and leakage of acridine orange to the cytosol from individual lysosomes was quantified visually as "loss of red dots" in U2-O-S cells and as a decrease in red and an increase in green fluorescence by Zeiss LSM DUO Software in fibroblasts. The total and cytoplasmic (digitonin-extracted) cathepsin activities were measured in digitonin-treated samples using zFR-AFC (Enzyme System Products) probe as described in the art. The tryptophan fluorescence spectra and liposome 90° light scattering were analyzed in a HEPES buffer (20 mM HEPES, 0.1 mM EDTA, pH as indicated) essentially as described in the art. Surface plasmon resonance measurements were performed with immobilized LUVs using a BIAcore 2000 system as described in the art. Hsp70 siRNA (5'-GCCAUGACGAAAGACAACAAUCUGU-3') and a control Hsp70 siRNA were transfected with Oligofectamine (Invitrogen). Immunodetection was performed with standard protocols. Apoptosis-like cell death and lysosomal membrane permeabilization were analyzed essentially as described in the art. ASM activity was analyzed by Amplex Red Sphingomyelinase Assay Kit (A12220) from Molecular Probes with modifications described in the art. Statistical analysis was performed using a two-tailed, paired Student's T-test and all groups of data were tested for the comparability of their variances using an F-test.

Methods

Cell Culture and Reagents.

Human U-2-OS osteosarcoma cells were cultivated in RPMI 1640 (Invitrogen) supplemented with 6% heat-inactivated calf serum and penicillin-streptomycin. Hsp70 transgenic and appropriate control MEFs were generated and maintained as described in the art. Human primary NPDA fibroblasts where grown in MEF media further supplemented with 1% Na-Pyruvate, 1% HEPES, 1% L-Glutamine. All cells were grown at 37° C. in a humidified air atmosphere with 5% $CO_2$ and repeatedly tested and found negative for mycoplasma. Unless otherwise stated, all chemicals were purchased from Sigma-Aldrich (Sigma-Aldrich Denmark A/S).

Assays for Lysosomal Integrity.

Sub-confluent cells incubated with 2 µg/ml acridine orange for 15 min at 37° C. were washed, irradiated and analyzed in Hanks balanced salt solution complemented with 3% fetal calf serum. Cells for single cell imaging were selected from 8 pre-defined areas of each well in transmitted light-mode after which the same cells were immediately visualized and exposed to blue light from USH102 100W mercury arc burner (Ushio electric) installed in a U-ULS100HG housing (Olympus) for 20 sec. Fluorescence microscopy was performed on Olympus IX-70 inverted microscope with a LCPIanF1 x20 objective with NA=0.40. Loss of lysosomal pH gradient was quantified by counting the loss of intense red staining. A more elaborate method for assaying lysosomal integrity was developed to handle the larger lysosomal compartment of the various fibroblasts used in this study. Cells for single cell imaging were selected from 8 pre-defined areas of each well in transmitted light-mode after which the same cells were immediately and continuously exposed to 489 nm light from a 100 mW diode laser while laser scanning micrographs where captured every 330 ms on a Zeiss LSM LIVE DUO confocal system in two channels defined by bandpass filters for 495-555 nm (green) and LP650 nm (Red) light. The resulting timelapse movies where subsequently analysed by the integrated Zeiss LSM DUO software.

The total and cytoplasmic (digitonin-extracted) cathepsin activities were measured in digitonin-treated samples using zFR-AFC (Enzyme System Products) probe as described in the art.

Assays for Cell Viability.

Cell density was assessed by the 3-(4,5-dimethylthiazole-2-y)-2,5-diphenyltetrasodiumbromide (MTT, SIGMA-Aldrich) reduction assay essentially as described in the art. Apoptosis-like cell death was assessed by staining the cells with 0.05 µg/ml Hoechst 33342 (Molecular Probes) and counting cells with condensed nuclei in an inverted Olympus IX-70 fluorescent Microscope (Filter U-MWU 330-385 nm). For each experiment a minimum of eight randomly chosen areas were counted.

Immunodetection and Microscopy.

Primary antibodies used included mouse monoclonal antibodies against Hsp70 (2H9; kindly provided by Boris Margulis, Russian Academy of Sciences, St. Petersburg, Russia), glyceraldehyde-3-phosphate dehydrogenase (GAPDH; Biogenesis), BMP (6C4), lysosomal integral membrane protein-1 (H5C6; developed by J. Thomas August and James E. K. Hildreth and obtained from the Developmental Studies Hybridoma Bank developed under the auspices of the NICHD and maintained by The University of Iowa, Department of Biological Sciences, Iowa City, USA). Proteins separated by 10% SDS-PAGE and transferred to a nitrocellulose membrane were detected by using indicated primary antibodies, appropriate peroxidase-conjugated secondary antibodies from Dako, ECL Western blotting reagents (Amersham), and Luminescent Image Reader (LAS-1000Plus, Fujifilm). For immunocytochemistry Alexa Fluor®-576- or Alexa Fluor®-488-conjugated secondary antibodies were used. Lysotracker Red® was used for live visualization of the lysosomal compartment. Fluorescence images were taken using a Zeiss Axiovert 100M laser scanning microscope. Lysotracker quantification and timelapse movies for lysosomal integrity were done on a Zeiss LSM LIVE DUO system.

Tryptophan Fluorescence Spectra and Liposome 90° Light Scattering.

The tryptophan fluorescence spectra (RFI) and liposome 90° light scattering (RSI) were analyzed in a HEPES buffer (20 mM HEPES, 0.1 mM EDTA, pH 7.4 or 6.0 as indicated) employing LUVs consisting of indicated lipids essentially as described in the art. For the RFI, LUVs were added in 10 µM aliquots and spectra recorded after a 20 min stabilization period. For the RSI, recombinant proteins were added in 0.12 nmol aliquots.

Surface Plasmon Resonance (BIAcore).

For preparation of LUVs a lipid mixture consisting of 10 mol % sphingomyelin, 50 mol % phosphatidylcholine, 20 mol % cholesterol and 20 mol % BMP dissolved in organic solvents, was dried under a stream of argon and rehydrated in Tris/HCl buffer (pH 7.4). The mixture was freeze-thawed nine times in liquid nitrogen and then in an incubator at 37° C. After ultrasound bath for 15 min the mixture was passed 21 times through a polycarbonate membrane with a pore diameter of 100 nm. Surface plasmon resonance measurements were performed using a BIAcore 2000 system at 25° C. LUVs (total lipid concentration 0.1 mM) were immobilized on the surface of a L1 sensor chip (BIAcore) in PBS (loading buffer). The running buffer used was sodium acetate buffer (50 mM, pH 4.5). As a control, acid sphingomyelinase (0.2 µM, 60 µl in running buffer) was injected directly on the liposome surface. Response units between 4100 RU-5250RU were obtained. The protein of interest was injected in running buffer at a flow rate of 20 µl/min at the concentrations indicated. After injection a dissociation phase of 10 min was appended. In the case where rASM followed rHsp70, rASM was added for 180 sec after the 10 min rHsp70-dissociation phase followed by yet a 10 min dissociation phase.

Molecular Modeling.

Primary structure analysis as well as molecular modeling were done with software availablefrom the Expert Protein Analysis System (EXPaSy) proteomics server of the Swiss Instituteof Bioinformatics (http://expasy.org/). Molecular modeling was done on basis of the crystalstructure of the human Hsp70-ATPase domain (pdb code: 1S3X) and the human Hsc70 substrate binding domain (pdb code: 7HSC) with DeepView-Swiss PDB Viewer. Surface models were based on coulomb interaction at pH 7.0 using a solvent dielectric constant of 80 ($H_2O$).

Statistical Analysis.

Statistical analysis was performed using a two-tailed, paired Student's T-test in order to evaluate the null-hypothesis. The cut-off level for statistical significance was set to 5% and all groups of data tested for the comparability of their variances using an F-test. All statistics were done on a minimum of n=3 independent experiments.

Example 3

Effect of Benzyl Alcohol on Lysosomal Storage Disease

Figure 11:
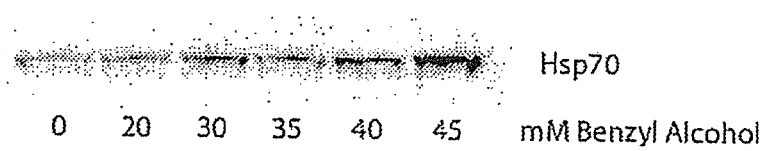
Figure 11:
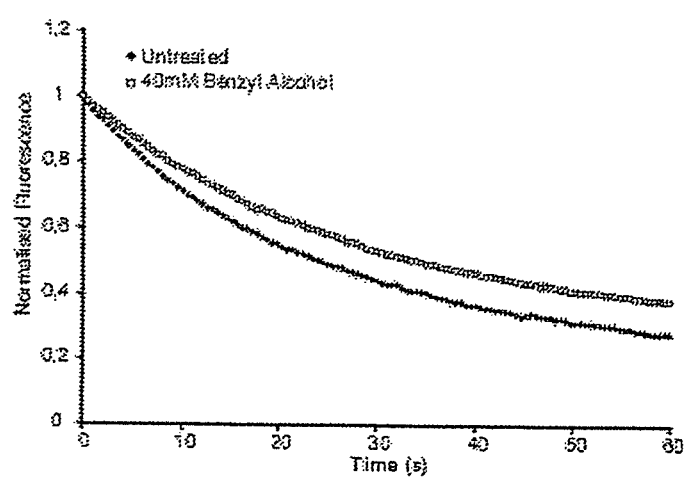
Figure 11:
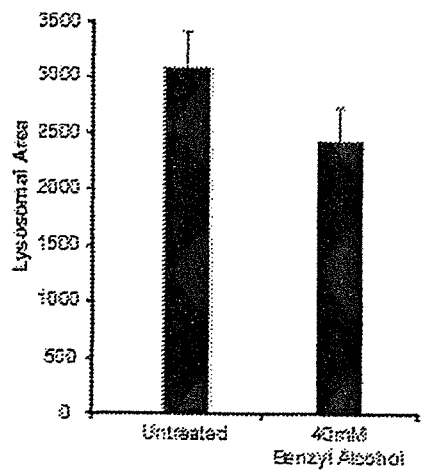
Figure 12:
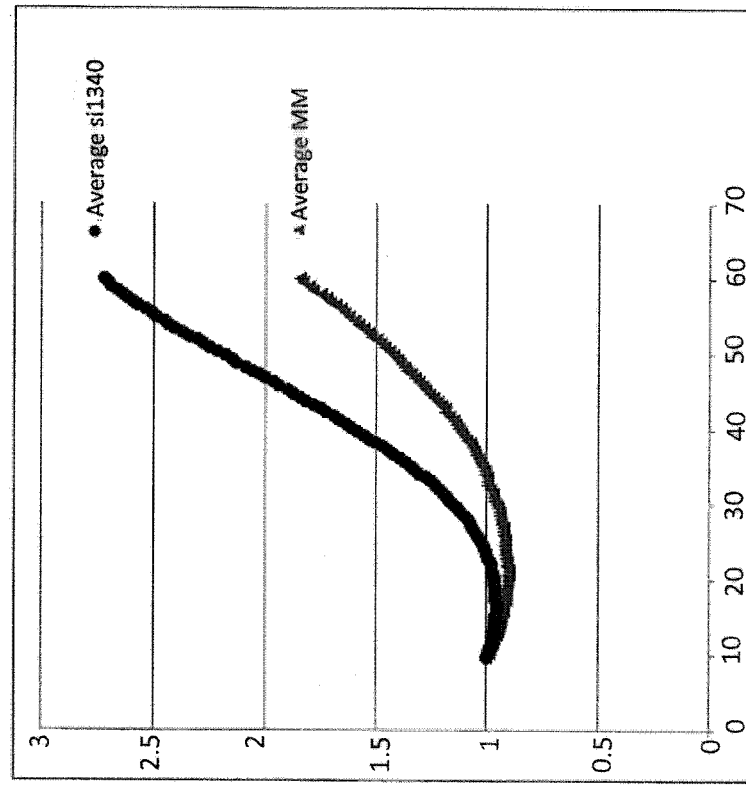
Figure 12:
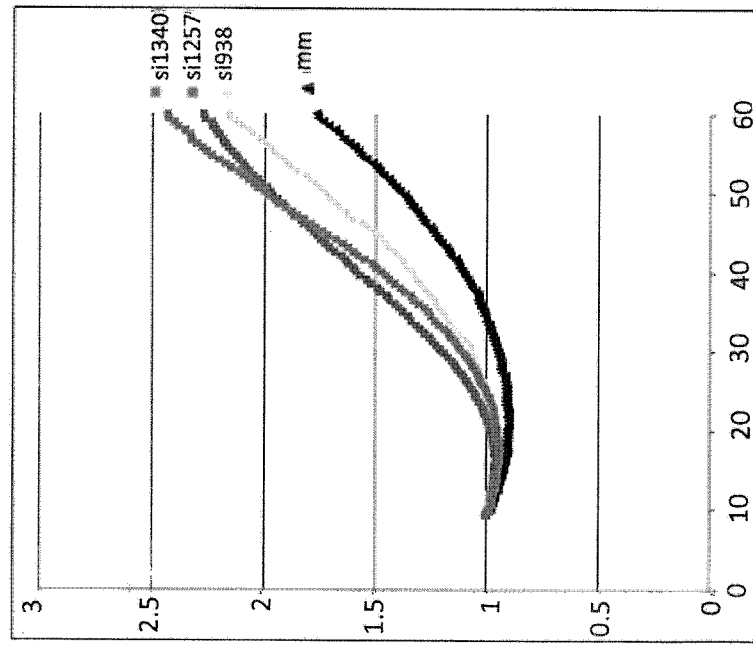
Figure 13:
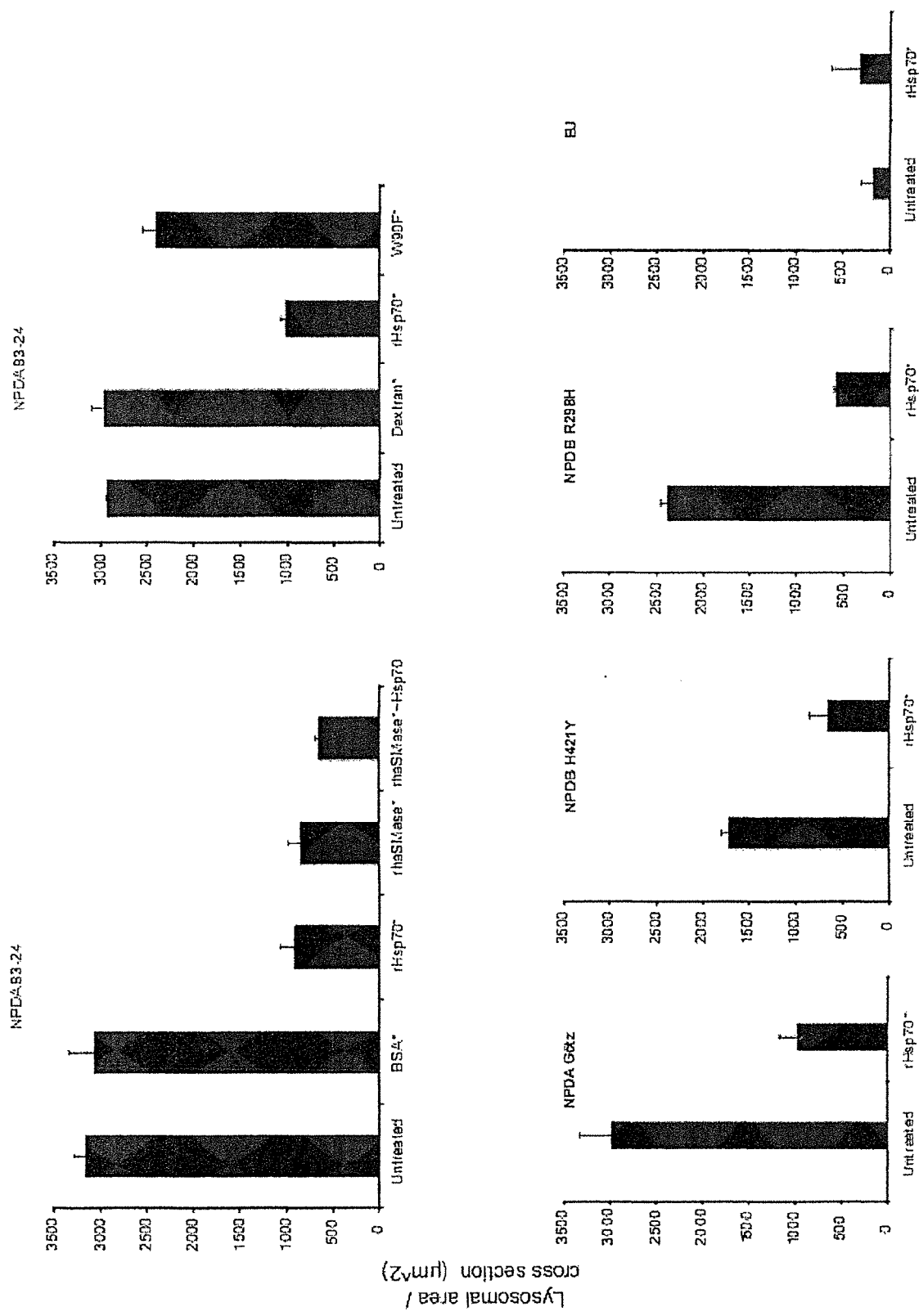
Figure 14:
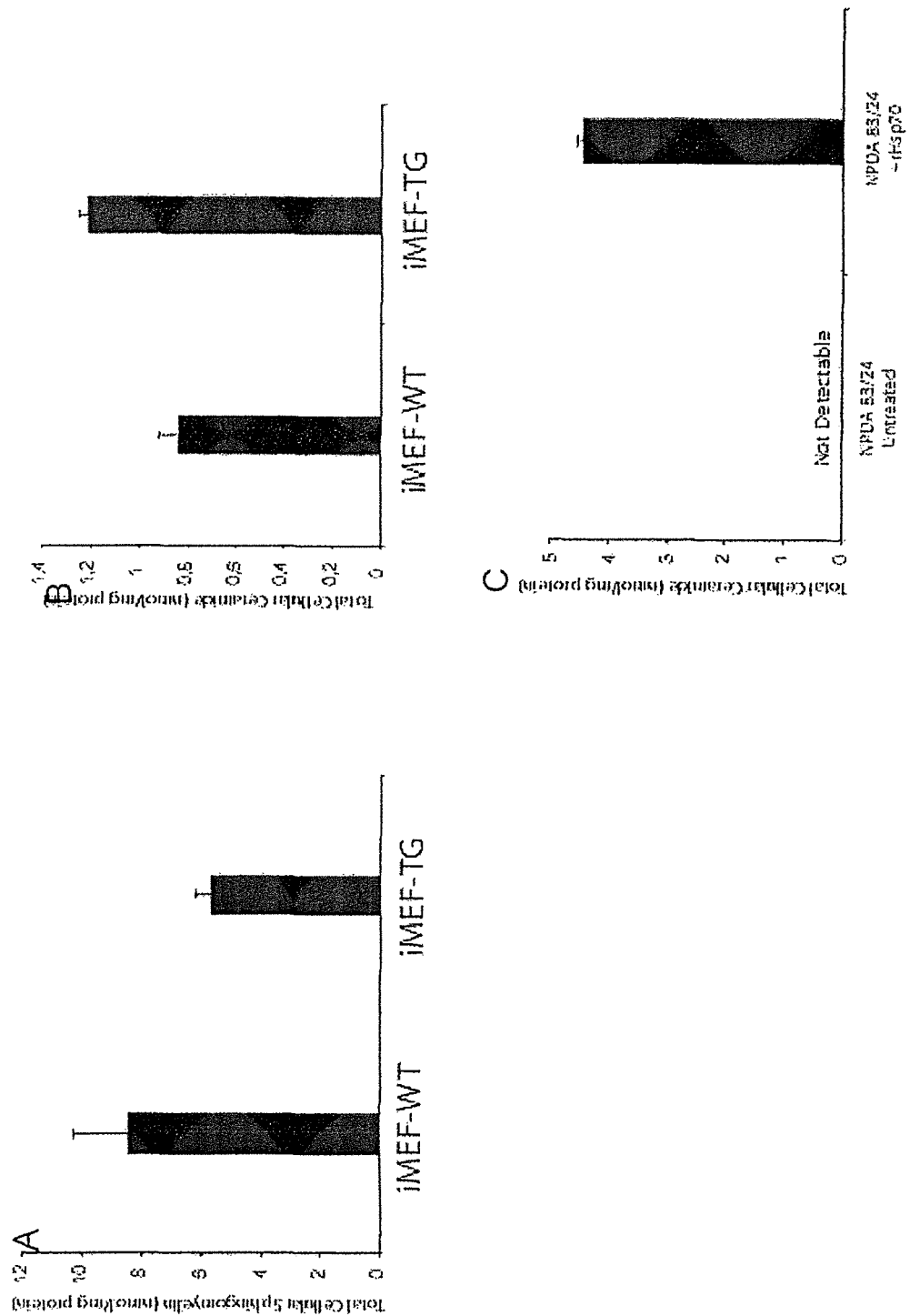
Figure 15:
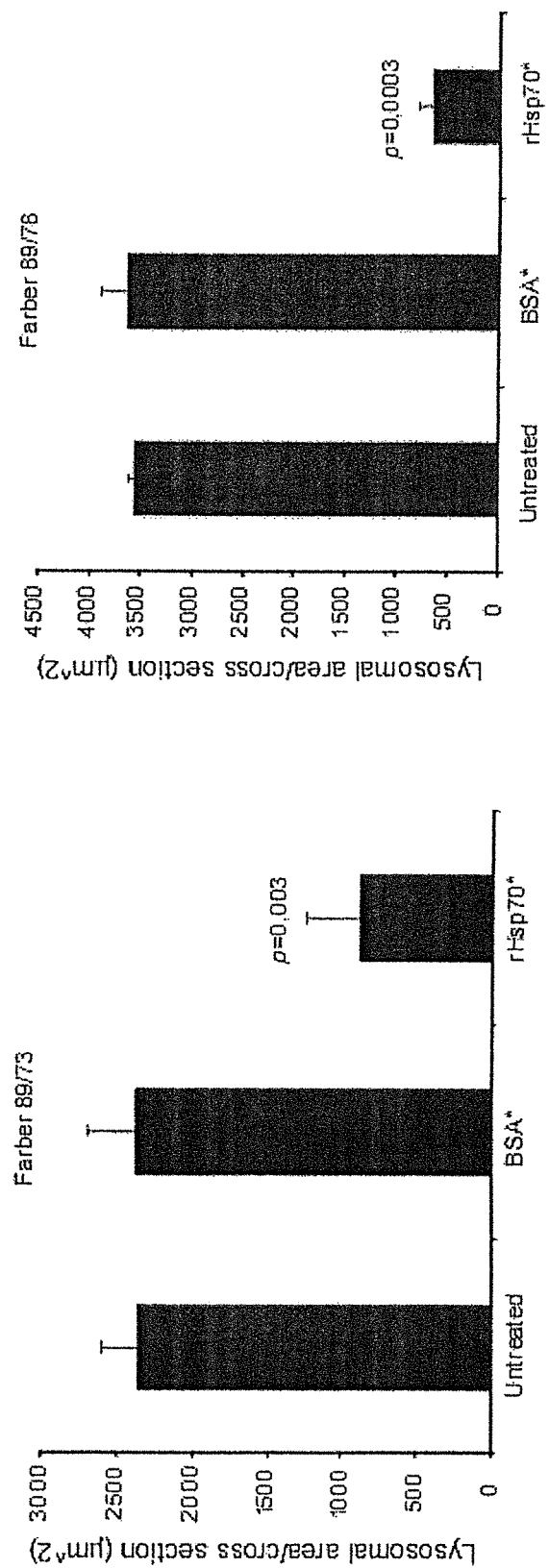

It is shown in Examples 2 and 3 that Hsp70 has a lysosome stabilizing effect via an interaction with BMP. In order to evaluate if this effect is also observed when exposing cells to a chemical Hsp70 inducer, Niemann-Pick Type A (NPDA) patient fibroblasts were treated with the small molecule Hsp70 inducer; Benzyl Alcohol (BA). Results are shown in FIG. 11. First, NPDA cells were treated with increasing doses of BA (0, 20, 30, 35, 40, 45 mM), lysed, and analysed by western blotting. The same amount of protein was loaded in each well. Hsp70 protein expression was evaluated for each condition, and shows that BA induced Hsp70 expression in a dose-dependent manner (primary antibody: Stressgen SPA-810, specific for Hsp70). Next, the stability of NPDA Götz lysosomes after treatment with 40 mM BA was evaluated, using the same methods as described in Example 2. An increased lysosomal stability was observed in response to BA. Finally, the lysosomal cross-sectional area in NPDA Götz cells after treatment with 40 mM BA was evaluated, using the same methods as described in Example 2. A decreased pathology is observed.

Items

1. Method for modulating the enzymatic activity of an enzyme, wherein said enzyme interacts with BMP, said method comprising the step of administering Hsp70, or a functional fragment thereof, in a form suitable for allowing interaction between BMP and Hsp70, or said functional fragment thereof, and thereby modulating the enzymatic activity of an enzyme interacting with BMP.
2. Method of item 1, wherein Hsp70 or said functional fragment thereof forms a covalent or non-covalent complex with BMP.
3. Method of any one of the preceding items, wherein BMP interacts with a saposin.
4. Method of item 3, wherein said saposin is selected from the group consisting of saposin A, saposin B, saposin C, and saposin D.
5. Method of any one of the preceding items, wherein said enzyme is selected from the group consisting of sphingomyelinase, acidic sphingomyelinase, sialidase, alpha-galactosidase, beta-galactosidase, beta-galactosylceremidase, glucosylceremidase, and acid ceremidase.
6. Hsp70, or a functional fragment thereof, for use as a medicament.
7. Hsp70, or a functional fragment thereof, for use in the treatment, alleviation, or prophylaxis of a lysosomal storage disorder.
8. Use of item 7, wherein said lysosomal storage disorder is selected from the group consisting of the disorders Niemann-Pick, Gaucher, Farber, Krabbe, Fabry, and Sialidosis.
9. A method for increasing the uptake of a compound, said method comprising the step of administering said compound together with Hsp70 or a functional fragment thereof.
10. Method of item 9, wherein said Hsp70 or a functional fragment thereof is covalently bound to said compound.

The invention claimed is:

1. A method for treatment of a lipid storage disorder (lipidosis) comprising administering to an individual in need thereof a bioactive agent capable of increasing the intracellular concentration of Hsp70 by amplifying Hsp70 gene expression, wherein said bioactive agent is a hydroxylamine derivative.

2. The method according to claim 1, wherein said treatment is curative or ameliorating.

3. The method according to claim 1, wherein said hydroxylamine derivative is bimoclomol, or a structural analogue thereof.

4. The method according to claim 1, wherein said hydroxylamine derivative is selected from the group consisting of bimoclomol, arimoclomol, BRX-220, BRX-345 and BGP-15.

5. The method according to claim 1, wherein said hydroxylamine derivative is arimoclomol.

6. The method according to claim 1, wherein said hydroxylamine derivative is BRX-345.

7. The method according to claim 1, wherein said lipid storage disorder is a sphingolipidosis.

8. The method according to claim 1, wherein said bioactive agent is administered in combination with at least one other treatment modality.

9. The method according to claim 8, wherein said at least one other treatment modality is individually selected from the group consisting of enzyme replacement therapy (ERT), pain relievers, corticosteroids, a transplantation, substrate reduction therapy, Hsp70 protein, a functional fragment of Hsp70 having at least 95% sequence identity to Hsp70, and a functional variant of Hsp70 having at least 95% sequence identity to Hsp70.

10. The method according to claim 1, wherein said bioactive agent is administered in combination with enzyme replacement therapy (ERT).

11. The method according to claim 10, wherein said enzyme replacement therapy is selected from the group consisting of imiglucerase, Miglustat, agalsidase beta and agalsidase alpha.

12. The method according to claim 9, wherein said functional fragment or variant of Hsp70 comprises all or part of the ATPase domain of Hsp70.

13. The method according to claim 9, wherein said Hsp70, or a functional fragment or variant thereof, is recombinant Hsp70 (rHsp70).

\* \* \* \* \*

SEQUENCE LISTING

```
<160> NUMBER OF SEQ ID NOS: 4

<210> SEQ ID NO 1
<211> LENGTH: 641
<212> TYPE: PRT
<213> ORGANISM: Homo sapiens

<400> SEQUENCE: 1

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30
```

```
Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
        130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
        290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
```

```
                450            455            460
Pro Pro Ala Pro Arg Gly Val Pro Gln Ile Glu Val Thr Phe Asp Ile
465            470            475            480

Asp Ala Asn Gly Ile Leu Asn Val Thr Ala Thr Asp Lys Ser Thr Gly
                485            490            495

Lys Ala Asn Lys Ile Thr Ile Thr Asn Asp Lys Gly Arg Leu Ser Lys
            500            505            510

Glu Glu Ile Glu Arg Met Val Gln Glu Ala Lys Tyr Lys Ala Glu
        515            520            525

Asp Glu Val Gln Arg Glu Arg Val Ser Ala Lys Asn Ala Leu Glu Ser
            530            535            540

Tyr Ala Phe Asn Met Lys Ser Ala Val Glu Asp Gly Leu Lys Gly
545            550            555            560

Lys Ile Ser Glu Ala Asp Lys Lys Val Leu Asp Lys Cys Gln Glu
                565            570            575

Val Ile Ser Trp Leu Asp Ala Asn Thr Leu Ala Glu Lys Asp Glu Phe
            580            585            590

Glu His Lys Arg Lys Glu Leu Glu Gln Val Cys Asn Pro Ile Ile Ser
        595            600            605

Gly Leu Tyr Gln Gly Ala Gly Gly Pro Gly Pro Gly Gly Phe Gly Ala
        610            615            620

Gln Gly Pro Lys Gly Gly Ser Gly Ser Gly Pro Thr Ile Glu Glu Val
625            630            635            640

Asp

<210> SEQ ID NO 2
<211> LENGTH: 2445
<212> TYPE: DNA
<213> ORGANISM: Homo sapiens

<400> SEQUENCE: 2
ataaaagccc aggggcaagc ggtccggata acggctagcc tgaggagctg ctgcgacagt      60
ccactacctt tttcgagagt gactcccgtt gtcccaaggc ttcccagagc gaacctgtgc     120
ggctgcaggc accggcgcgt cgagtttccg gcgtccggaa ggaccgagct cttctcgcgg     180
atccagtgtt ccgtttccag cccccaatct cagagcggag ccgacagaga gcagggaacc     240
ggcatggcca agccgcggc gatcggcatc gacctgggca ccacctactc ctgcgtgggg     300
gtgttccaac acggcaaggt ggagatcatc gccaacgacc agggcaaccg caccaccccc     360
agctacgtgg ccttcacgga caccgagcgg ctcatcgggg atgcggccaa gaaccaggtg     420
gcgctgaacc cgcagaacac cgtgtttgac gcgaagcggc tgattggccg caagttcggc     480
gacccggtgt gcagtcgga catgaagcac tggccttttcc aggtgatcaa cgacggagac     540
aagcccaagg tgcaggtgag ctacaagggg gagaccaagg cattctaccc cgaggagatc     600
tcgtccatgt gctgaccaa gatgaaggag atcgccgagg cgtacctggg ctacccggtg     660
accaacgcgg tgatcaccgt gccggcctac ttcaacgact cgcagcgcca ggccaccaag     720
gatgcgggtg tgatcgcggg gctcaacgtg ctgcggatca tcaacgagcc cacggccgcc     780
gccatcgcct acggcctgga cagaacgggc aaggggagc gcaacgtgct catctttgac     840
ctgggcgggg gcaccttcga cgtgtccatc ctgacgatcg acgacggcat cttcgaggtg     900
aaggccacgg ccggggacac ccacctgggt ggggaggact tgacaacag gctggtgaac     960 cacttcgtgg aggagttcaa gagaaaacac aagaaggaca tcagccagaa caagcgagcc    1020
```

```
gtgaggcggc tgcgcaccgc ctgcgagagg gccaagagga ccctgtcgtc cagcacccag   1080
gccagcctgg agatcgactc cctgtttgag ggcatcgact tctacacgtc catcaccagg   1140
gcgaggttcg aggagctgtg ctccgacctg ttccgaagca ccctggagcc cgtggagaag   1200
gctctgcgcg acgccaagct ggacaaggcc cagattcacg acctggtcct ggtcgggggc   1260
tccacccgca tccccaaggt gcagaagctg ctgcaggact tcttcaacgg gcgcgacctg   1320
aacaagagca tcaaccccga cgaggctgtg gcctacgggg cggcggtgca ggcggccatc   1380
ctgatggggg acaagtccga gaacgtgcag gacctgctgc tgctggacgt ggctcccctg   1440
tcgctggggc tggagacggc cggaggcgtg atgactgccc tgatcaagcg caactccacc   1500
atccccacca agcagacgca gatcttcacc acctactccg acaaccaacc cggggtgctg   1560
atccaggtgt acgagggcga gagggccatg acgaaagaca caatctgtt ggggcgcttc   1620 gagctgagcg gcatccctcc ggcccccagg ggcgtgcccc agatcgaggt gaccttcgac   1680
atcgatgcca acggcatcct gaacgtcacg gccacggaca agagcaccgg caaggccaac   1740
aagatcacca tcaccaacga caagggccgc ctgagcaagg aggagatcga gcgcatggtg   1800
caggaggcgg agaagtacaa agcggaggac gaggtgcagc gcgagagggt gtcagccaag   1860
aacgccctgg agtcctacgc cttcaacatg aagagcgccg tggaggatga ggggctcaag   1920
ggcaagatca gcgaggcgga caagaagaag gtgctggaca agtgtcaaga ggtcatctcg   1980
tggctggacg ccaacaccct tggccgagaag gacgagtttg agcacaagag gaaggagctg   2040
gagcaggtgt gtaaccccat catcagcgga ctgtaccagg gtgccggtgg tcccgggcct   2100
gggggcttcg gggctcaggg tcccaaggga gggtctgggt caggccccac cattgaggag   2160
gtagattagg ggccttttcca agattgctgt ttttgttttg gagcttcaag actttgcatt   2220
tcctagtatt tctgtttgtc agttctcaat ttcctgtgtt tgcaatgttg aaatttttttg   2280 gtgaagtact gaacttgctt ttttttccggt ttctacatgc agagatgaat ttatactgcc   2340
atcttacgac tatttcttct ttttaataca cttaactcag gccatttttt aagttggtta   2400
cttcaaagta aataaacttt aaaattcaaa aaaaaaaaaa aaaaa                   2445
```

<210> SEQ ID NO 3
<211> LENGTH: 641
<212> TYPE: PRT
<213> ORGANISM: Homo sapiens

<400> SEQUENCE: 3

```
Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125
```

-continued

```
Glu Ile Ala Glu Ala Tyr Leu Gly Tyr Pro Val Thr Asn Ala Val Ile
    130                 135                 140
Thr Val Pro Ala Tyr Phe Asn Asp Ser Gln Arg Gln Ala Thr Lys Asp
145                 150                 155                 160
Ala Gly Val Ile Ala Gly Leu Asn Val Leu Arg Ile Ile Asn Glu Pro
                165                 170                 175
Thr Ala Ala Ala Ile Ala Tyr Gly Leu Asp Arg Thr Gly Lys Gly Glu
            180                 185                 190
Arg Asn Val Leu Ile Phe Asp Leu Gly Gly Gly Thr Phe Asp Val Ser
        195                 200                 205
Ile Leu Thr Ile Asp Asp Gly Ile Phe Glu Val Lys Ala Thr Ala Gly
    210                 215                 220
Asp Thr His Leu Gly Gly Glu Asp Phe Asp Asn Arg Leu Val Asn His
225                 230                 235                 240
Phe Val Glu Glu Phe Lys Arg Lys His Lys Lys Asp Ile Ser Gln Asn
                245                 250                 255
Lys Arg Ala Val Arg Arg Leu Arg Thr Ala Cys Glu Arg Ala Lys Arg
            260                 265                 270
Thr Leu Ser Ser Ser Thr Gln Ala Ser Leu Glu Ile Asp Ser Leu Phe
        275                 280                 285
Glu Gly Ile Asp Phe Tyr Thr Ser Ile Thr Arg Ala Arg Phe Glu Glu
    290                 295                 300
Leu Cys Ser Asp Leu Phe Arg Ser Thr Leu Glu Pro Val Glu Lys Ala
305                 310                 315                 320
Leu Arg Asp Ala Lys Leu Asp Lys Ala Gln Ile His Asp Leu Val Leu
                325                 330                 335
Val Gly Gly Ser Thr Arg Ile Pro Lys Val Gln Lys Leu Leu Gln Asp
            340                 345                 350
Phe Phe Asn Gly Arg Asp Leu Asn Lys Ser Ile Asn Pro Asp Glu Ala
        355                 360                 365
Val Ala Tyr Gly Ala Ala Val Gln Ala Ala Ile Leu Met Gly Asp Lys
    370                 375                 380
Ser Glu Asn Val Gln Asp Leu Leu Leu Leu Asp Val Ala Pro Leu Ser
385                 390                 395                 400
Leu Gly Leu Glu Thr Ala Gly Gly Val Met Thr Ala Leu Ile Lys Arg
                405                 410                 415
Asn Ser Thr Ile Pro Thr Lys Gln Thr Gln Ile Phe Thr Thr Tyr Ser
            420                 425                 430
Asp Asn Gln Pro Gly Val Leu Ile Gln Val Tyr Glu Gly Glu Arg Ala
        435                 440                 445
Met Thr Lys Asp Asn Asn Leu Leu Gly Arg Phe Glu Leu Ser Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                485                 490                 495
Lys Ala Asn Lys Ile Thr Ile Thr Asn Asp Lys Gly Arg Leu Ser Lys
            500                 505                 510
Glu Glu Ile Glu Arg Met Val Gln Glu Ala Lys Tyr Lys Ala Glu
        515                 520                 525
Asp Glu Val Gln Arg Glu Arg Val Ser Ala Lys Asn Ala Leu Glu Ser
530                 535                 540
```

```
Tyr Ala Phe Asn Met Lys Ser Ala Val Glu Asp Glu Gly Leu Lys Gly
545                 550                 555                 560
Lys Ile Ser Glu Ala Asp Lys Lys Val Leu Asp Lys Cys Gln Glu
                565                 570                 575
Val Ile Ser Trp Leu Asp Ala Asn Thr Leu Ala Glu Lys Asp Glu Phe
                580                 585                 590
Glu His Lys Arg Lys Glu Leu Glu Gln Val Cys Asn Pro Ile Ile Ser
            595                 600                 605
Gly Leu Tyr Gln Gly Ala Gly Gly Pro Gly Pro Gly Phe Gly Ala
        610                 615                 620
Gln Gly Pro Lys Gly Gly Ser Gly Ser Gly Pro Thr Ile Glu Glu Val
625                 630                 635                 640
Asp

<210> SEQ ID NO 4
<211> LENGTH: 2551
<212> TYPE: DNA
<213> ORGANISM: Homo sapiens

<400> SEQUENCE: 4
```

| | | | | |
|---|---|---|---|---|
| ggaaaacggc | cagcctgagg | agctgctgcg | agggtccgct | tcgtctttcg agagtgactc | 60 |
| ccgcggtccc | aaggctttcc | agagcgaacc | tgtgcggctg | caggcaccgg cgtgttgagt | 120 |
| ttccggcgtt | ccgaaggact | gagctcttgt | cgcggatccc | gtccgccgtt tccagccccc | 180 |
| agtctcagag | cggagcccac | agagcagggc | accggcatgg | ccaaagccgc ggcgatcggc | 240 |
| atcgacctgg | gcaccaccta | ctcctgcgtg | ggggtgttcc | aacacggcaa ggtggagatc | 300 |
| atcgccaacg | accagggcaa | ccgcaccacc | ccagctacg | tggccttcac ggacaccgag | 360 |
| cggctcatcg | gggatgcggc | caagaaccag | gtggcgctga | acccgcagaa caccgtgttt | 420 |
| gacgcgaagc | ggctgatcgg | ccgcaagttc | ggcgacccgg | tggtgcagtc ggacatgaag | 480 |
| cactggcctt | tccaggtgat | caacgacgga | gacaagccca | aggtgcaggt gagctacaag | 540 |
| ggggagacca | aggcattcta | ccccgaggag | atctcgtcca | tggtgctgac aagatgaag | 600 |
| gagatcgccg | aggcgtacct | gggctacccg | gtgaccaacg | cggtgatcac cgtgccggcc | 660 |
| tacttcaacg | actcgcagcg | ccaggccacc | aaggatgcgg | gtgtgatcgc ggggctcaac | 720 |
| gtgctgcgga | tcatcaacga | gcccacggcc | gccgccatcg | cctacggcct ggacagaacg | 780 |
| ggcaaggggg | agcgcaacgt | gctcatcttt | gacctgggcg | ggggcacctt cgacgtgtcc | 840 |
| atcctgacga | tcgacgacgg | catcttcgag | gtgaaggcca | cggccgggga caccccacctg | 900 |
| ggtggggagg | actttgacaa | caggctggtg | aaccacttcg | tggaggagtt caagagaaaa | 960 |
| cacaagaagg | acatcagcca | gaacaagcga | gccgtgaggc | ggctgcgcac cgcctgcgag | 1020 |
| agggccaaga | ggaccctgtc | gtccagcacc | caggccagcc | tggagatcga ctccctgttt | 1080 |
| gagggcatcg | acttctacac | gtccatcacc | agggcgaggt | tcgaggagct gtgctccgac | 1140 |
| ctgttccgaa | gcaccctgga | gcccgtggag | aaggctctgc | gcgacgccaa gctggacaag | 1200 |
| gcccagattc | acgacctggt | cctggtcggg | ggctccaccc | gcatccccaa ggtgcagaag | 1260 |
| ctgctgcagg | acttcttcaa | cgggcgcgac | ctgaacaaga | gcatcaaccc cgacgaggct | 1320 |
| gtggcctacg | ggcggcggt | gcaggcggcc | atcctgatgg | gggacaagtc cgagaacgtg | 1380 |
| caggacctgc | tgctgctgga | cgtggctccc | ctgtcgctgg | ggctggagac ggccggaggc | 1440 |
| gtgatgactg | ccctgatcaa | gcgcaactcc | accatcccca | ccaagcagac gcagatcttc | 1500 |
| accacctact | ccgacaacca | accggggtg | ctgatccagg | tgtacgaggg cgagagggcc | 1560 |

```
atgacgaaag acaacaatct gttggggcgc ttcgagctga gcggcatccc tccggccccc    1620
aggggcgtgc cccagatcga ggtgaccttc gacatcgatg ccaacggcat cctgaacgtc    1680
acggccacgg acaagagcac cggcaaggcc aacaagatca ccatcaccaa cgacaagggc    1740
cgcctgagca aggaggagat cgagcgcatg gtgcaggagg cggagaagta caaagcggag    1800
gacgaggtgc agcgcgagag ggtgtcagcc aagaacgccc tggagtccta cgccttcaac    1860
atgaagagcg ccgtggagga tgagggctc aagggcaaga tcagcgaggc ggacaagaag    1920
aaggttctgg acaagtgtca agaggtcatc tcgtggctgg acgccaacac cttggccgag    1980
aaggacgagt tgagcacaa gaggaaggag ctggagcagg tgtgtaaccc catcatcagc    2040
ggactgtacc agggtgccgg tggtcccggg cctggcggct tcggggctca gggtcccaag    2100
ggagggtctg ggtcaggccc taccattgag gaggtggatt aggggccttt gttctttagt    2160
atgtttgtct ttgaggtgga ctgttgggac tcaaggactt tgctgctgtt ttcctatgtc    2220
atttctgctt cagctctttg ctgcttcact tctttgtaaa gttgtaacct gatggtaatt    2280
agctggcttc attattttg tagtacaacc gatatgttca ttagaattct ttgcatttaa    2340
tgttgatact gtaagggtgt ttcgttccct ttaaatgaat caacactgcc accttctgta    2400
cgagtttgtt tgttttttt tttttttttt tttttgctt ggcgaaaaca ctacaaaggc    2460
tgggaatgta tgtttttata atttgtttat ttaaatatga aaataaaat gttaaactt    2520 aaaaaaaaaa aaaaaaaaaa aaaaaaaaaa a                                  2551
```